(12) United States Patent
Handique

(10) Patent No.: US 11,724,256 B2
(45) Date of Patent: Aug. 15, 2023

(54) SYSTEM AND METHOD FOR AUTOMATED SINGLE CELL PROCESSING AND ANALYSES

(71) Applicant: Bio-Rad Laboratories, Inc, Hercules, CA (US)

(72) Inventor: Kalyan Handique, Ann Arbor, MI (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 443 days.

(21) Appl. No.: 16/890,417

(22) Filed: Jun. 2, 2020

(65) Prior Publication Data

US 2020/0391210 A1    Dec. 17, 2020

Related U.S. Application Data

(60) Provisional application No. 62/907,791, filed on Sep. 30, 2019, provisional application No. 62/861,826, filed on Jun. 14, 2019.

(51) Int. Cl.
*B01L 3/00* (2006.01)
*G01N 15/14* (2006.01)
(Continued)

(52) U.S. Cl.
CPC ... *B01L 3/502715* (2013.01); *B01L 3/502746* (2013.01); *B01L 3/502761* (2013.01); (Continued)

(58) Field of Classification Search
CPC ......... B01L 3/502715; B01L 3/502746; B01L 3/502761; B01L 2200/0652;
(Continued)

(56) References Cited

U.S. PATENT DOCUMENTS 4,475,411 A   10/1984   Wellerfors
4,551,435 A   11/1985   Liberti et al.
(Continued)

FOREIGN PATENT DOCUMENTS

CA    2994321 A1   11/2005
CN   103894248 A    7/2014
(Continued)

OTHER PUBLICATIONS

Dura, Burak, et al., "scFTD-seq: freeze-thaw lysis based, portable approach toward highly distributed single-cell 3' mRNA profiling", Nucleic Acids Research, 2019, vol. 47, No. 3, published online Nov. 20, 2018.
(Continued)

*Primary Examiner* — Jennifer Wecker
*Assistant Examiner* — Michael Paul Shimek
(74) *Attorney, Agent, or Firm* — Jeffrey Schox

(57) ABSTRACT

A system and method for automated single cell capture and processing is described, where the system includes a deck supporting and positioning a set of sample processing elements (including an integrated imaging subsystem); a gantry for actuating tools for interactions with the set of sample processing elements supported by the deck; and a base supporting various processing subsystems and a control subsystems in communication with the processing subsystems. The system can automatically execute workflows associated with single cell processing, including antibody detection, other protein detection, mRNA detection, and/or other applications associated with spatial transcriptomics.

16 Claims, 27 Drawing Sheets

(51) Int. Cl.
*G01N 1/40* (2006.01)
*C12M 1/00* (2006.01)
*C12Q 1/6888* (2018.01)
*C12Q 1/6813* (2018.01)
*G01N 15/10* (2006.01)

(52) U.S. Cl.
CPC .......... *C12M 47/04* (2013.01); *C12Q 1/6813* (2013.01); *C12Q 1/6888* (2013.01); *G01N 1/405* (2013.01); *G01N 1/4077* (2013.01); *G01N 15/1484* (2013.01); *B01L 2200/0652* (2013.01); *B01L 2200/0668* (2013.01); *B01L 2300/0816* (2013.01); *B01L 2300/0829* (2013.01); *G01N 2015/1006* (2013.01); *G01N 2015/149* (2013.01)

(58) Field of Classification Search
CPC ..... B01L 2200/0668; B01L 2300/0816; B01L 2300/0829; B01L 2200/027; B01L 2300/046; B01L 2300/0822; B01L 2300/0893; B01L 2200/0663; C12M 47/04; C12M 23/12; C12M 41/46; C12M 41/48; C12Q 1/6813; C12Q 1/6888; G01N 1/405; G01N 1/4077; G01N 15/1484; G01N 2015/1006; G01N 2015/149; G01N 2458/10; G01N 2469/20; G01N 15/10; G01N 33/56983; G01N 35/00; G01N 2035/0436; G01N 35/04; G01N 2035/00346; G01N 35/00029; G01N 2035/00366; G01N 2333/165
See application file for complete search history.

(56) References Cited

U.S. PATENT DOCUMENTS

| | | |
|---|---|---|
| 4,710,635 A | 12/1987 | Chupp |
| 5,266,269 A | 11/1993 | Niiyama et al. |
| 5,281,540 A | 1/1994 | Merkh et al. |
| 5,491,343 A | 2/1996 | Brooker |
| 5,541,064 A | 7/1996 | Bacus et al. |
| 5,547,849 A | 8/1996 | Baer et al. |
| 5,851,488 A | 12/1998 | Saul et al. |
| 5,883,370 A | 3/1999 | Walker et al. |
| 5,888,370 A | 3/1999 | Becker et al. |
| 5,993,630 A | 11/1999 | Becker et al. |
| 5,993,632 A | 11/1999 | Becker et al. |
| 6,016,712 A | 1/2000 | Warden et al. |
| 6,127,177 A | 10/2000 | Toner et al. |
| 6,133,030 A | 10/2000 | Bhatia et al. |
| 6,150,180 A | 11/2000 | Parce et al. |
| 6,174,683 B1 | 1/2001 | Hahn |
| 6,221,663 B1 | 4/2001 | Bhatia et al. |
| 6,228,624 B1 | 5/2001 | Terstappen |
| 6,281,008 B1 | 8/2001 | Komai et al. |
| 6,287,832 B1 | 9/2001 | Becker et al. |
| 6,365,362 B1 | 4/2002 | Terstappen et al. |
| 6,410,724 B1 | 6/2002 | Dejean et al. |
| 6,433,134 B1 | 8/2002 | Patron et al. |
| 6,525,997 B1 | 2/2003 | Narayanaswami et al. |
| 6,563,634 B2 | 5/2003 | Shimada et al. |
| 6,613,525 B2 | 9/2003 | Nelson et al. |
| 6,623,983 B1 | 9/2003 | Terstappen et al. |
| 6,641,708 B1 | 11/2003 | Becker et al. |
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,821,484 B1 | 11/2004 | Gregersen |
| 6,861,259 B2 | 3/2005 | Columbus |
| 6,866,823 B2 | 3/2005 | Wardlaw |
| 6,960,449 B2 | 11/2005 | Wang et al. |
| 7,008,789 B2 | 3/2006 | Gambini et al. |
| 7,035,170 B2 | 4/2006 | Narayanaswami et al. |
| 7,046,357 B2 | 5/2006 | Weinberger et al. |
| 7,148,492 B2 | 12/2006 | Loney et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,248,352 B2 | 7/2007 | Hamamatsu et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte et al. |
| 7,332,288 B2 | 2/2008 | Terstappen et al. |
| 7,338,760 B2 | 3/2008 | Gong et al. |
| 7,354,389 B2 | 4/2008 | Kureshy et al. |
| 7,439,062 B2 | 10/2008 | Bhatt et al. |
| 7,449,558 B2 | 11/2008 | Yao et al. |
| 7,449,778 B2 | 11/2008 | Sander |
| 7,507,528 B2 | 3/2009 | Albert et al. |
| 7,588,672 B2 | 9/2009 | Unger et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,704,322 B2 | 4/2010 | Hansen et al. |
| 7,710,563 B2 | 5/2010 | Betzig et al. |
| 7,738,320 B2 | 6/2010 | Taha |
| 7,763,704 B2 | 7/2010 | Ding et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,174,698 B2 | 5/2012 | Peter et al. |
| 8,175,371 B2 | 5/2012 | George et al. |
| 8,186,913 B2 | 5/2012 | Toner et al. |
| 8,211,301 B2 | 7/2012 | Safar et al. |
| 8,232,112 B2 | 7/2012 | Willson et al. |
| 8,252,517 B2 | 8/2012 | Thomas et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 8,628,923 B2 | 1/2014 | Hamilton et al. |
| 8,658,418 B2 | 2/2014 | Daridon |
| 8,680,025 B2 | 3/2014 | Cooney |
| 8,730,479 B2 | 5/2014 | Ness et al. |
| 8,765,454 B2 | 7/2014 | Zhou et al. |
| 8,771,609 B2 | 7/2014 | Ehben et al. |
| 8,802,367 B2 | 8/2014 | Taniguchi et al. |
| 8,936,945 B2 | 1/2015 | Handique et al. |
| 8,986,988 B2 | 3/2015 | Karnik et al. |
| 9,103,754 B2 | 8/2015 | Handique et al. |
| 9,110,026 B2 | 8/2015 | Collins |
| 9,133,499 B2 | 9/2015 | Di Carlo et al. |
| 9,145,540 B1 | 9/2015 | Deutsch et al. |
| 9,174,216 B2 | 11/2015 | Handique et al. |
| 9,188,586 B2 | 11/2015 | Fan et al. |
| 9,194,001 B2 | 11/2015 | Brenner |
| 9,200,245 B2 | 12/2015 | Deutsch et al. |
| 9,201,060 B2 | 12/2015 | Voldman et al. |
| 9,249,459 B2 | 2/2016 | Hamilton et al. |
| 9,260,753 B2 | 2/2016 | Xie et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,768 B2 | 4/2016 | Vrouwe et al. |

(56) References Cited

U.S. PATENT DOCUMENTS

| | | |
|---|---|---|
| 9,315,857 B2 | 4/2016 | Fu et al. |
| 9,329,170 B2 | 5/2016 | Clarke et al. |
| 9,364,829 B2 | 6/2016 | Heid et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,507,609 B2 | 11/2016 | Glazer et al. |
| 9,513,195 B2 | 12/2016 | Handique et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,610,581 B2 | 4/2017 | Handique et al. |
| 9,637,799 B2 | 5/2017 | Fan et al. |
| 9,701,998 B2 | 7/2017 | Hindson et al. |
| 9,707,562 B2 | 7/2017 | Handique et al. |
| 9,708,659 B2 | 7/2017 | Fodor et al. |
| 9,757,707 B2 | 9/2017 | Husain et al. |
| 9,802,193 B2 | 10/2017 | Handique et al. |
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 10,376,889 B1 | 8/2019 | Masquelier et al. |
| 10,391,492 B2 | 8/2019 | Handique et al. |
| 10,391,493 B2 | 8/2019 | Handique et al. |
| 10,401,373 B1 | 9/2019 | Holmes et al. |
| 10,533,152 B1 | 1/2020 | Belgrader et al. |
| 10,633,693 B1 | 4/2020 | Handique et al. |
| 10,947,581 B2 | 3/2021 | Handique et al. |
| 2002/0009759 A1 | 1/2002 | Terstappen et al. |
| 2002/0028431 A1 | 3/2002 | Julien |
| 2002/0036142 A1 | 3/2002 | Gascoyne et al. |
| 2002/0036823 A1 | 3/2002 | Shimada et al. |
| 2002/0098535 A1 | 7/2002 | Wang et al. |
| 2002/0109838 A1 | 8/2002 | Columbus |
| 2002/0119482 A1 | 8/2002 | Nelson et al. |
| 2002/0192808 A1 | 12/2002 | Gambini et al. |
| 2003/0129676 A1 | 7/2003 | Terstappen et al. |
| 2003/0138941 A1 | 7/2003 | Gong et al. |
| 2004/0029241 A1 | 2/2004 | Hahn et al. |
| 2004/0106130 A1 | 6/2004 | Besemer et al. |
| 2004/0160599 A1 | 8/2004 | Hamamatsu et al. |
| 2004/0191891 A1 | 9/2004 | Tsinberg et al. |
| 2004/0218472 A1 | 11/2004 | Narayanaswami et al. |
| 2004/0229349 A1 | 11/2004 | Daridon |
| 2004/0248318 A1 | 12/2004 | Weinberger et al. |
| 2005/0001176 A1 | 1/2005 | Loney et al. |
| 2005/0014201 A1 | 1/2005 | Deuthsch |
| 2005/0037343 A1 | 2/2005 | Fagnani et al. |
| 2005/0042685 A1 | 2/2005 | Albert et al. |
| 2005/0063863 A1 | 3/2005 | Columbus |
| 2005/0095582 A1 | 5/2005 | Gillim-Ross et al. |
| 2005/0112589 A1 | 5/2005 | Hahn et al. |
| 2005/0118640 A1 | 6/2005 | Kureshy et al. |
| 2005/0158804 A1 | 7/2005 | Yao et al. |
| 2005/0164236 A1 | 7/2005 | Su et al. |
| 2005/0181463 A1 | 8/2005 | Rao et al. |
| 2005/0265815 A1 | 12/2005 | Rodi |
| 2006/0040274 A1 | 2/2006 | Tsinberg |
| 2006/0040407 A1 | 2/2006 | Falcovitz-Gerassi et al. |
| 2006/0050142 A1 | 3/2006 | Scott et al. |
| 2006/0115380 A1 | 6/2006 | Kagan et al. |
| 2006/0128006 A1 | 6/2006 | Gerhardt et al. |
| 2006/0141045 A1 | 6/2006 | Bhatt et al. |
| 2006/0147959 A1 | 7/2006 | Bell et al. |
| 2006/0160243 A1 | 7/2006 | Tang et al. |
| 2006/0257992 A1 | 11/2006 | McDevitt et al. |
| 2006/0263250 A1 | 11/2006 | Blouin et al. |
| 2007/0026381 A1 | 2/2007 | Huang et al. |
| 2007/0053800 A1 | 3/2007 | Lehto |
| 2007/0111302 A1 | 5/2007 | Handique et al. |
| 2007/0154960 A1 | 7/2007 | Connelly et al. |
| 2007/0161051 A1 | 7/2007 | Tsinberg et al. |
| 2007/0172903 A1 | 7/2007 | Toner et al. |
| 2007/0243523 A1 | 10/2007 | Ionescu-Zanetti et al. |
| 2007/0252265 A1 | 11/2007 | Sander |
| 2007/0264675 A1 | 11/2007 | Toner et al. |
| 2007/0275418 A1 | 11/2007 | Hollmann et al. |
| 2008/0003224 A1 | 1/2008 | Fong et al. |
| 2008/0014589 A1 | 1/2008 | Link et al. |
| 2008/0068588 A1 | 3/2008 | Hess et al. |
| 2008/0090239 A1 | 4/2008 | Shoemaker et al. |
| 2008/0096212 A1 | 4/2008 | Bell et al. |
| 2008/0113906 A1 | 5/2008 | Ding et al. |
| 2008/0124726 A1 | 5/2008 | Monforte |
| 2008/0182273 A1 | 7/2008 | Hansen et al. |
| 2008/0206751 A1 | 8/2008 | Squirrell et al. |
| 2008/0207615 A1 | 8/2008 | Bell et al. |
| 2008/0220422 A1 | 9/2008 | Shoemaker et al. |
| 2008/0234264 A1 | 9/2008 | Bell et al. |
| 2008/0240539 A1 | 10/2008 | George et al. |
| 2008/0248043 A1 | 10/2008 | Babcook et al. |
| 2008/0317325 A1 | 12/2008 | Ortyn et al. |
| 2009/0014360 A1 | 1/2009 | Toner et al. |
| 2009/0061450 A1 | 3/2009 | Hunter |
| 2009/0081773 A1 | 3/2009 | Kaufman |
| 2009/0141593 A1 | 6/2009 | Taha |
| 2009/0153844 A1 | 6/2009 | Peter et al. |
| 2009/0162853 A1 | 6/2009 | Clark et al. |
| 2009/0215088 A1 | 8/2009 | Forsyth et al. |
| 2009/0220979 A1 | 9/2009 | Davis et al. |
| 2009/0221059 A1 | 9/2009 | Williams et al. |
| 2009/0258383 A1 | 10/2009 | Kovac et al. |
| 2009/0317836 A1 | 12/2009 | Kuhn et al. |
| 2010/0087325 A1 | 4/2010 | Buermann |
| 2010/0120077 A1 | 5/2010 | Daridon |
| 2010/0127168 A1 | 5/2010 | Khursheed |
| 2010/0210009 A1 | 8/2010 | Willson et al. |
| 2010/0232675 A1 | 9/2010 | Ortyn et al. |
| 2010/0233693 A1 | 9/2010 | Kopf-Sill et al. |
| 2010/0261179 A1 | 10/2010 | Betley et al. |
| 2010/0291584 A1 | 11/2010 | Tseng et al. |
| 2010/0304485 A1 | 12/2010 | Karnik et al. |
| 2010/0304978 A1 | 12/2010 | Robbins et al. |
| 2011/0003380 A1 | 1/2011 | Miltenyi et al. |
| 2011/0005932 A1 | 1/2011 | Jovanovich et al. |
| 2011/0045994 A1 | 2/2011 | Voldman et al. |
| 2011/0053151 A1 | 3/2011 | Hansen et al. |
| 2011/0104718 A1 | 5/2011 | Rao et al. |
| 2011/0117634 A1 | 5/2011 | Halamish et al. |
| 2011/0143964 A1 | 6/2011 | Zhou et al. |
| 2011/0227558 A1 | 9/2011 | Mannion et al. |
| 2011/0236904 A1 | 9/2011 | Hauch et al. |
| 2011/0280467 A1 | 11/2011 | George et al. |
| 2012/0021456 A1 | 1/2012 | Levine et al. |
| 2012/0071355 A9 | 3/2012 | Cooney |
| 2012/0129190 A1 | 5/2012 | Chiu et al. |
| 2012/0156675 A1 | 6/2012 | Lueerssen et al. |
| 2012/0164679 A1 | 6/2012 | Vrouwe et al. |
| 2012/0194805 A1 | 8/2012 | Ness et al. |
| 2012/0316074 A1 | 12/2012 | Saxonov |
| 2013/0011832 A1 | 1/2013 | Moreno et al. |
| 2013/0116102 A1 | 5/2013 | Hansen |
| 2013/0171628 A1 | 7/2013 | Di et al. |
| 2013/0230860 A1 | 9/2013 | Park et al. |
| 2013/0244906 A1 | 9/2013 | Collins |
| 2013/0259635 A1 | 10/2013 | Maslana et al. |
| 2013/0309778 A1 | 11/2013 | Lowe et al. |
| 2014/0051595 A1 | 2/2014 | So |
| 2014/0155295 A1 | 6/2014 | Hindson et al. |
| 2014/0173443 A1 | 6/2014 | Hawkins et al. |
| 2014/0212881 A1 | 7/2014 | Handique et al. |
| 2014/0213487 A1 | 7/2014 | Freudenthal et al. |
| 2014/0272965 A1 | 9/2014 | Handique et al. |
| 2014/0315237 A1 | 10/2014 | Masujima et al. |
| 2014/0329301 A1 | 11/2014 | Handique |
| 2014/0357511 A1 | 12/2014 | Handique et al. |
| 2014/0370612 A1 | 12/2014 | Bassler et al. |
| 2015/0011432 A1 | 1/2015 | Saxonov |
| 2015/0089359 A1 | 3/2015 | Brisebois |
| 2015/0093306 A1 | 4/2015 | Thorne et al. |
| 2015/0133319 A1 | 5/2015 | Fu et al. |
| 2015/0160135 A1 | 6/2015 | Tibbe et al. |

(56) References Cited

U.S. PATENT DOCUMENTS

| | | |
|---|---|---|
| 2015/0160931 A1 | 6/2015 | Glazer et al. |
| 2015/0204864 A1 | 7/2015 | Fan et al. |
| 2015/0299784 A1 | 10/2015 | Fan et al. |
| 2015/0376609 A1 | 12/2015 | Hindson et al. |
| 2016/0008814 A1 | 1/2016 | Handique et al. |
| 2016/0024572 A1 | 1/2016 | Shishkin et al. |
| 2016/0024761 A1 | 1/2016 | Korb |
| 2016/0053253 A1 | 2/2016 | Salathia et al. |
| 2016/0060621 A1 | 3/2016 | Agresti et al. |
| 2016/0130649 A1 | 5/2016 | Xie et al. |
| 2016/0199838 A1 | 7/2016 | Handique et al. |
| 2016/0209319 A1 | 7/2016 | Adalsteinsson et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2016/0367991 A1 | 12/2016 | Petersen et al. |
| 2017/0044525 A1 | 2/2017 | Kaper et al. |
| 2017/0153219 A1 | 6/2017 | Handique et al. |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2017/0370951 A1 | 12/2017 | Buffiere et al. |
| 2018/0030515 A1 | 2/2018 | Regev et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0274027 A1 | 9/2018 | Hindson et al. |
| 2018/0282804 A1 | 10/2018 | Hindson et al. |
| 2019/0002814 A1 | 1/2019 | Masquelier et al. |
| 2019/0060902 A1 | 2/2019 | Handique et al. |

FOREIGN PATENT DOCUMENTS

| | | |
|---|---|---|
| CN | 103998394 A | 8/2014 |
| CN | 104789468 A | 7/2015 |
| EP | 2414548 A2 | 2/2012 |
| EP | 2414548 B1 | 10/2015 |
| JP | 2006098696 A | 4/2006 |
| JP | 2009195160 A | 9/2009 |
| JP | 2013500496 A | 1/2013 |
| JP | 2013541959 A | 11/2013 |
| JP | 2015527588 A | 9/2015 |
| JP | 2017063716 A | 4/2017 |
| WO | 2003035909 A2 | 5/2003 |
| WO | 2006098696 A1 | 9/2006 |
| WO | 2010120818 A2 | 10/2010 |
| WO | 2010142954 A1 | 12/2010 |
| WO | 2011017094 A2 | 2/2011 |
| WO | 2012057548 A2 | 5/2012 |
| WO | 2013176767 A1 | 11/2013 |
| WO | 2016149639 A1 | 9/2016 |
| WO | 2016151719 A1 | 9/2016 |
| WO | 2016162997 A1 | 10/2016 |
| WO | 2016191533 A1 | 12/2016 |
| WO | 2018013723 A1 | 1/2018 |
| WO | 2018058073 A2 | 3/2018 |
| WO | 2019006436 A1 | 1/2019 |

OTHER PUBLICATIONS

"High-throughput imaging of a unique continuous flow microfluidics plate", Scikon Innovation, Application Note, May 2016, https://www.moleculardevices.com/en/assets/app-note/dd/img/high-throughput-imaging-of-a-unique-continuous-flow-microfluidics-plate#gref.

Chen, H., et al., "High-throughput, deterministic single cell trapping and long-term clonal cell culture in microfluidic devices", Lab Chip. Feb. 21, 2015;15(4):1072-83. doi: 10.1039/c4lc01176g. PMID: 25519528.

Sarkar, S., et al., "Phenotypic drug profiling in droplet microfluidics for better targeting of drug-resistant tumors", Lab on a chip., vol. 15, 23 (2015): 4441-50. doi:10.1039/c5lc00923e.

Yeh, EC, et al., "Self-powered integrated microfluidic point-of-care low-cost enabling (SIMPLE) chip", Sci Adv. Mar. 22, 2017;3(3):e1501645. doi:10.1126/sciadv.1501645. PMID: 28345028; PMCID: PM 5362183.

Yuan, J., et al., "An Automated Microwell Platform for Large-Scale Single Cell RNA-Seq.", Sci Rep. Sep. 27, 2016;6:33883. doi: 10.1038/srep33883. PMID: 27670648; PMCID: PMC5037380.

International Search Report and Written Opinion for application No. PCT/US20/035704 dated Sep. 9, 2020.

International Search Report and Written Opinion for application No. PCT/US20/31502 dated Sep. 16, 2020.

Murphy, Travis W., et al., "Recent advances in the use of microfluidic technologies for signs;e cell analysis", Analyst, Oct. 26, 2017, vol. 143, pp. 60-80.

Stahl, Patrik L., et al., "Visualization and analysis of gene expression in tissue sections by spatial transcriptomics", sciencemag.org, Jul. 2016, vol. 353, Issue 6294, pp. 78-82.

Australian Examination Report for Application No. 2018323449, dated Feb. 25, 2020.

Guo, P. et al. Microfluidic capture and release of bacteria in a conical nanopore array. Lab Chip. vol. 12, p. 558-561, 2012, published online Nov. 2011.

International Search Report and Written Opinion for PCT Application No. PCT/US17/62099 dated Feb. 12, 2018.

International Search Report and Written Opinion of the ISA for application No. PCT/US20/022902 dated Apr. 22, 2020.

International Search Report for PCT Application No. PCT/US2018/048353 dated Nov. 5, 2018.

Lindstrom, Sara (Royal Institute of Technology, Stockholm, Sweden, 2009, pp. 1-80).

International Preliminary Report on Patentability for PCT Application No. PCT/US17/62099 dated May 31, 2019.

Seale, K. T. et al. "Mirrored pyramidal wells for simultaneous multiple vantage point microscopy." Journal of Microscopy (2008) 232 1-6. (Year: 2008).

Sugio, Yoshihiro; et al., An agar-based on-chip neural-cell-cultivation system for stepwise control of network pattern generation during cultivation, Dept. of Life Sciences, Graduate School of Arts and Sciences, University of Tokyo, Jun. 24, 2003.

Supplemental information from Tan et al. PNAS (2007) 104. (Year: 2007).

Tan, Wei-Heang et al. "A trap-and-release integrated microfluidic system for dynamic microarray applications." PNAS (2007) 104 1146-1151. (Year: 2007).

(TOP VIEW) (BOTTOM VIEW)

SYSTEM AND METHOD FOR AUTOMATED SINGLE CELL PROCESSING AND ANALYSES

CROSS-REFERENCE TO RELATED APPLICATIONS

This application claims the benefit of U.S. Provisional Application No. 62/861,826 filed on 14 Jun. 2019 and U.S. Provisional Application 62/907,791 filed on 30 Sep. 2019, which are each incorporated in its entirety herein by this reference.

TECHNICAL FIELD

This invention relates generally to the sample processing field, and more specifically to a new and useful automated system and method for single cell processing and analyses in the sample processing field.

BACKGROUND

With an increased interest in cell-specific drug testing, diagnosis, and other assays, systems and methods that allow for individual cell isolation, identification, and retrieval are becoming highly desirable. Single cell capture systems and methods have been shown to be particularly advantageous for these applications. However, associated processes and protocols for single cell capture and subsequent analysis often must be performed in a particular order and with a high precision in order to properly maintain the cells. As such, these processes can be time consuming for the user, as well as result in damage to the cells or otherwise unfavorable results if they are not performed properly (e.g., through mistakes in pipetting, through a mix-up of reagents, etc.). In particular, these novel high throughput single cell cytometry assays have great utility in translational medicine, personalized therapy selections, clinical diagnostics, and/or other applications of use, but lack of automation prevents proper performance by novice users, thereby limiting throughput.

Furthermore, advancements in massively parallel single-cell analysis systems (e.g., with respect to systems for analyzing proteins or mRNA) are revolutionizing immunology research. High throughput single-cell gene expression profiling of patient immune cells now allows researchers to make a more accurate and granular assessments of the complex immune state of a subject. However, despite the continuous progress over the last decade in the development of multiplexed single-cell analysis technologies, there are still practical limitations that restrict the rapid adoption of these powerful tools. Workflows for obtaining biomarker results from cell samples are still very complicated, require expert user interventions, are subject to long processing times and have limited access (e.g., with respect to accessing multiple high-cost cutting edge instrument systems), thereby blocking access to such tools for many. Thus, there is a need for a more cost-effective, rapid, integrated, and automated system that can analyze large numbers of single cells with generation of quantitative measurements (e.g., of large numbers of proteins and/or other biomarkers per cell).

DESCRIPTION OF THE PREFERRED EMBODIMENTS

Figure 1A:
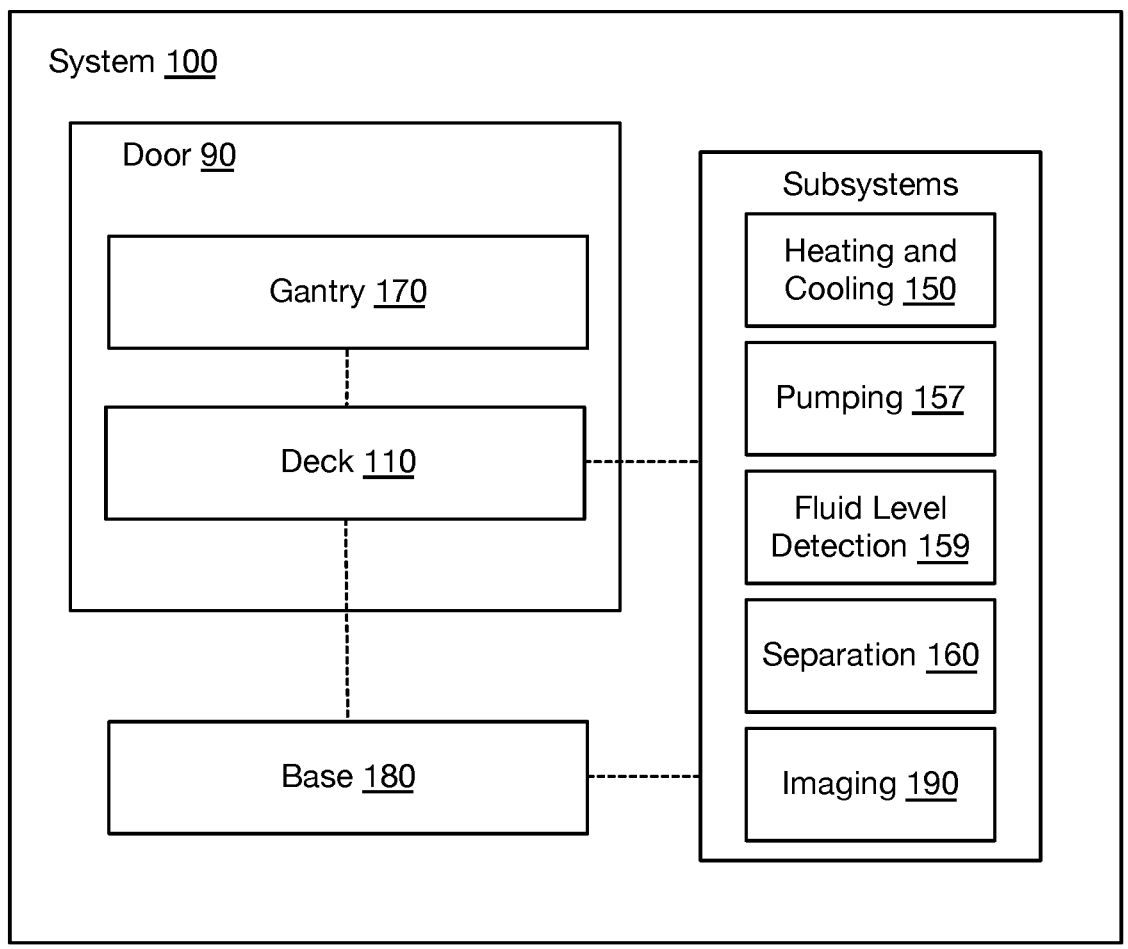
FIGS. 1A-1C depict schematic representations of an embodiment of a system for automated single cell sample processing.

The following description of the preferred embodiments of the invention is not intended to limit the invention to these preferred embodiments, but rather to enable any person skilled in the art to make and use this invention.

1. Benefits

The invention(s) can confer several benefits over conventional systems and methods.

In particular, the invention(s) confer(s) the benefit of providing cost-effective, rapid, integrated, and automated systems and methods for analyzing large numbers of single cells with generation of quantitative measurements (e.g., of large numbers of proteins and/or other biomarkers per cell), where the integrated systems further include integrated systems with real-time imaging (e.g., fluorescence imaging of sample capture substrates). Embodiments of the invention(s) can provide high performance solutions (e.g., in terms of high cell number, in terms of high multiplexing performance, in terms of full automation, etc.) for rapid dissemination of technologies across different users, in a very cost-effective manner.

Additionally, the invention(s) confer(s) the benefit of enabling single-cell proteogenomic applications. For instance, single-Cell Cytometry (SCC) involves novel methods for characterization of cell populations based on protein markers, far beyond the detection quantities of conventional flow and mass cytometry. Such characterization can include antibody-staining/tagging based analysis (e.g., antibody signal detection with separation of cell types and quantification of cell populations, analyses associated with protein quantification, etc.). While protein markers are described, the invention(s) also cover the use of markers and tagging with respect to mRNAs, DNA, glycans, and/or other biomaterials.

Additionally, the invention(s) confer(s) the benefit of providing an end-to-end solution that can decentralize cutting-edge high parameter single cell cytometry. In particular, such a solution allows a wider range of entities doing immunological studies, with discovery, translational, and/or clinical applications, to afford the use of a state-of-the-art single cell tool in their experiments.

Additionally, the invention(s) confer(s) the benefit of providing designs for sample processing disposables, where the disposables include regions for co-capturing cells, in single cell format, with functionalized particles. Such disposables can additionally or alternatively include regions designed for transmitting heat during sample processing.

Additionally, the invention(s) confer(s) the benefit of enabling at least partial automation of the protocols involved in single cell capture and subsequent processing, thereby optimizing run success and consistency. In more detail, the user can be removed from part or all of the method (e.g. loading samples, capping lids, on-instrument lysis, reverse transcription processes, cDNA amplification, bead or cDNA product retrieval, on-instrument library preparation and cleanup, etc.). Further, the system and/or method can enable better accuracy of a protocol over conventional systems and methods (e.g. better accuracy in the addition of the correct reagents, better temperature control of reagents, rapid processing of critical liquid handling steps, precise incubation times, optimal bead washing and separation, automated bar code reading, etc.). Further, the system and/or method can confer the benefit of preventing accidents (e.g. knocking the system, spills of reagents, contamination of sample or instrument, etc.), which can commonly occur during the manual performance of a protocol.

Additionally, through use of limited-use and/or pre-loaded and unitized reagent cartridges, the system and/or method can confer the benefit of providing a streamlined user experience with optimized quality control and design architecture to accommodate on-going development of assays and future applications. As such, the system confers the benefit of independent or nearly independent control of reagents or reagent groups. In a specific example of this variation, the system includes a reagent cartridge having any or all of the following dedicated regions: a room temperature region, a cooling region, a heating region, a magnetic region (e.g., overlapping with a heating region), waste capture region, intermediate reagent parking region or any other suitable region. In a related benefit, the system and/or method can confer the benefit of enabling the user to purchase smaller volumes of reagents, such as through the distribution of reagents in protocol-specific types and quantities to be used in accordance with specific automated protocols. This can function to save costs, reduce reagent waste, or have any other suitable outcome.

Additionally, through use of fluid handling and separation elements (e.g., magnetic separation components), the system and/or method can confer the benefit of providing automated sample and library cleanup steps. Relatedly, the system and/or method can confer the benefit of establishing better fluid flow throughout the system. In a first example, this is enabled through an automated pipetting system (e.g., pipettor, gantry, and assorted pipette tips), which can monitor and/or direct fluid flow (e.g., to maintain an optimal flow rate, to establish an optimal volume of reagents, etc.) without user intervention. The fluid handling system components for single cell preparation and/or other assays may involve use of both of (a) liquid pipettor coupled to a gantry for fluidic dispensing and pumping into a fluidic channel or fluidic reservoir (e.g., of a sample processing cartridge) and/or (b) a built-in on-chip pressurizable waste chamber connected and controlled through a valve integrated with the fluidic network, as described in more detail below. Such a combined dual liquid handling system gives unprecedented control of the flow (e.g., microliter per second to tens of milliliters per second), delivery (e.g., 1-100,000 microliters), and residence time (e.g., milliseconds to hours) of reagents through the fluidic system. Additionally or alternatively, the system can monitor and/or direct fluid flow with user intervention (e.g., with minimal user intervention, to encourage optimal user intervention, etc.).

Additionally, through software and workflow improvements, the system and/or method can minimize number of manual operations performed by a user, and provide relevant system status reports to ensure smooth operation and sample processing.

Additionally, the system confers the benefit of three-dimensional mobility of a component, such as a pipettor. In a specific example of this variation, the system includes a gantry providing X-Y-Z mobility for a pipettor, enabling the pipettor to perform a variety of tasks associated with fluid delivery (e.g., piercing foil coverings of reagent tubes, transferring materials among a set of wells, etc.) and/or other sample processing steps (e.g., separation of target material, heating, cooling, etc.) in an automated fashion.

Additionally or alternatively, the system and/or method can confer any other suitable benefit.

2. System

Figure 1B:
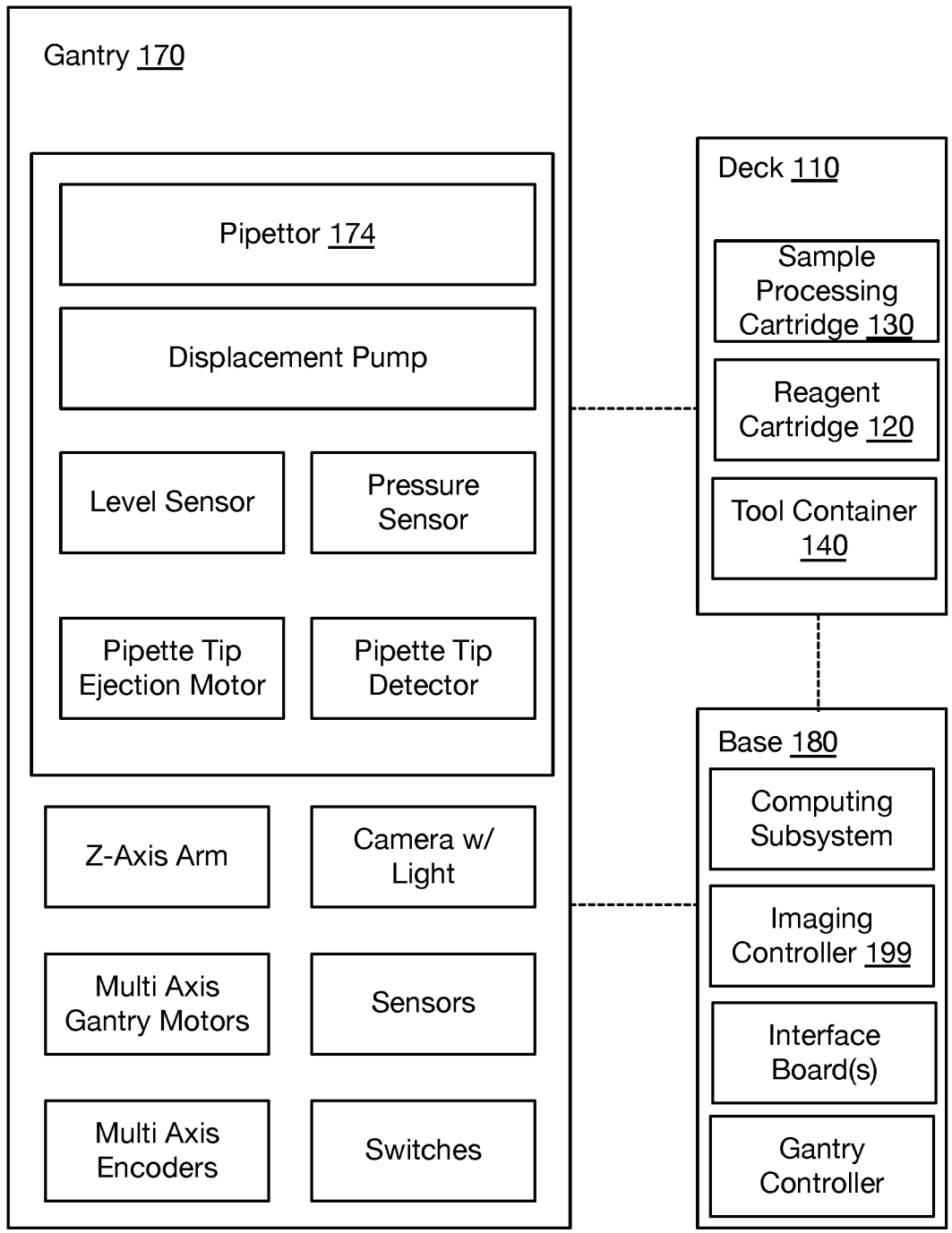
Figure 1C:
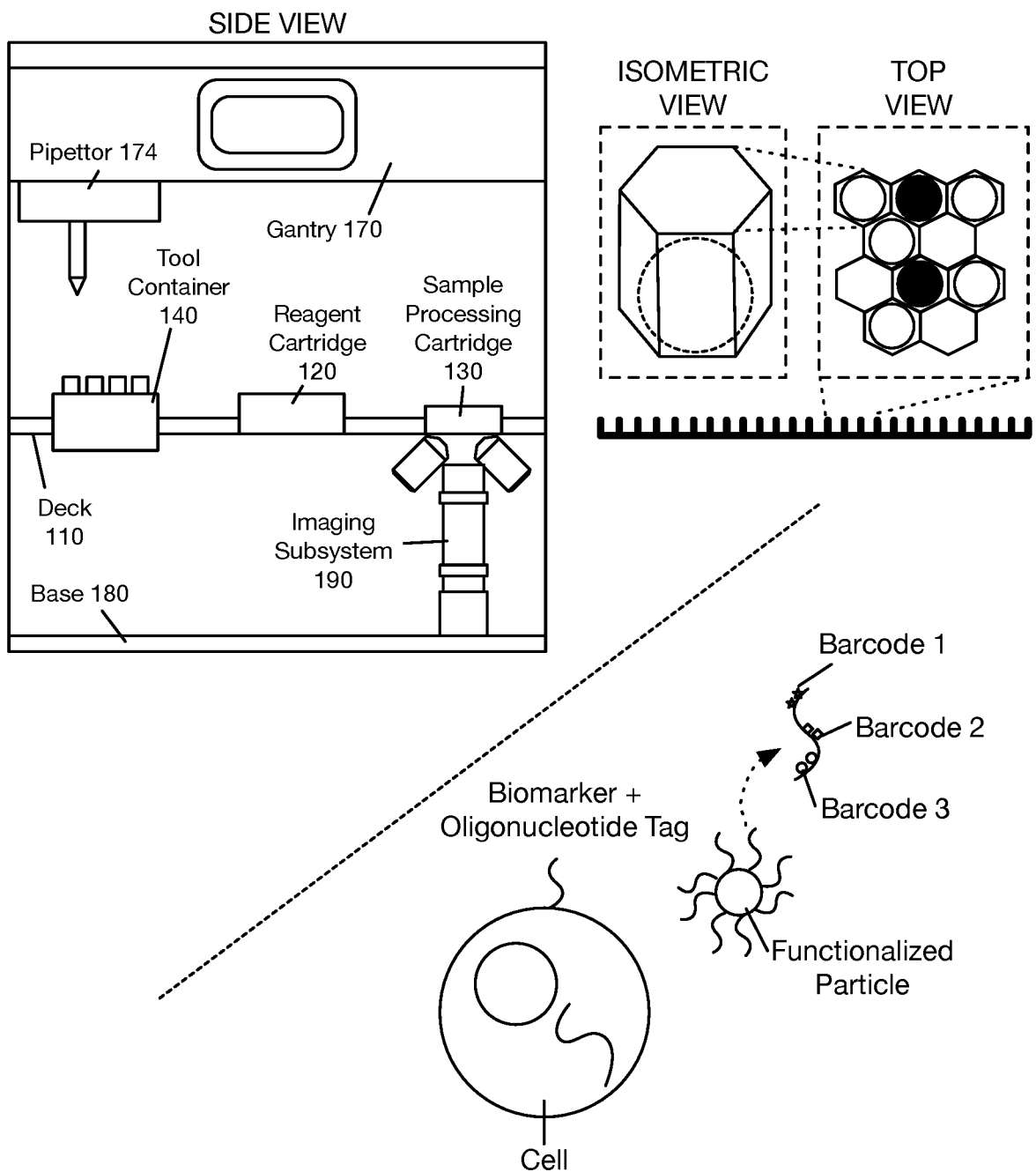

As shown in FIGS. 1A-1C, an embodiment of a system 100 for automated single cell capture and processing includes: a deck 110 supporting and positioning a set of sample processing elements; a gantry 170 for actuating tools for interactions with the set of sample processing elements supported by the deck 110; and a base 180 supporting various processing subsystems and a control subsystems in communication with the processing subsystems, wherein the control subsystems control states of the deck 110, the set of sample processing elements, and the gantry 170 in order to transition the system 100 between various operation modes. Embodiments, variations, and examples of operation modes, which provide various workflows, are described in further detail in Section 3 below.

Embodiments of the system 100 function to provide cost-effective, rapid, integrated, and automated systems and methods for analyzing mRNA aspects and/or protein aspects of large numbers of single cells, with generation of quantitative measurements (e.g., of large numbers of proteins and/or other biomarkers per cell), where the integrated systems further include integrated subsystems for real-time imaging applications (e.g., fluorescence imaging of sample capture substrates). Embodiments of the system 100 can also provide high performance solutions (e.g., in terms of high cell number, in terms of high multiplexing performance, in terms of full automation, etc.) for rapid dissemination of technologies across different users, in a very cost-effective manner.

In specific applications, embodiments of the system 100 can automatically enable single-cell proteogenomic applications. For instance, single-Cell Cytometry (SCC) involves novel methods for characterization of cell populations based on protein markers, far beyond the detection quantities of conventional flow and mass cytometry. Such characterization can include antibody-staining/tagging based analysis (e.g., antibody signal detection with separation of cell types and quantification of cell populations, analyses associated with protein quantification, etc.). While protein markers are described, the invention(s) also cover the use of markers and tagging with respect to mRNAs, DNA, glycans, and/or other biomaterials.

Additionally, embodiments of the system 100 can function to provide an end-to-end solution for performing high parameter single cell cytometry. In particular, such a solution allows a wider range of entities doing immunological studies, with discovery, translational, and/or clinical applications, to afford the use of a state-of-the-art single cell tool in their experiments. Additionally, embodiments of the system 100 can function to provide sample processing disposables, where the disposables include regions for co-capturing cells, in single cell format, with functionalized particles. Such disposables can additionally or alternatively include regions designed for transmitting heat during sample processing.

As described above, in relation to sample processing, embodiments of the system 100 can include or be configured to process cells, cell-derived material, and/or other biological material (e.g., cell-free nucleic acids). The cells can include any or all of mammalian cells (e.g., human cells, mouse cells, etc.), embryos, stem cells, plant cells, or any other suitable kind of cells. The cells can contain target material (e.g., target lysate, mRNA, RNA, DNA, etc.) which originates within the cells and is optionally captured by the cell capture system for processing. Additionally, the containers containing the cells can be prepared from multiple cell-containing samples (e.g., 12 samples, 24 samples, 48 samples, 96 samples, 384 samples, 1536 samples, other numbers of samples), wherein the various samples are hashed or barcoded prior to mixing them together into a single container (or reduced number of containers). This feature enables automated processing of multiple samples in the same automated run for their respective single cell preparation and library preparation operations. Additionally or alternatively, the system 100 can be configured to interact with particles (e.g., beads, probes, nucleotides, oligonucleotides, polynucleotides, etc.), droplets, encapsulated cells, encapsulated biomarkers, reagents, or any other suitable materials.

The system can further additionally or alternatively include any or all of the system components as described in U.S. application Ser. No. 16/867,235, filed 5 May 2020; U.S. application Ser. No. 16/867,256, filed 5 May 2020; U.S. application Ser. No. 16/564,375 filed 9 Sep. 2019; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, which are each incorporated in their entirety by this reference.

2.1 System: Deck

As shown in FIGS. 1A-1C and 2A-2D, the deck 110 functions as a platform to support and position one or more components of the system 100 (e.g., at a top broad surface, at a top and bottom broad surface, at a side surface, etc.) for automated sample processing. Furthermore, the deck 110 can function to position one or more components of the system 100 to align with or otherwise interact with fluid processing subsystems, imaging subsystems, heating subsystems, separation subsystems (e.g., magnetic separation subsystems), and/or other subsystems coupled to the gantry 170 and/or base 180, as described below. In this regard, the deck 110 can be stationary as a reference platform, while other components are actuated into position for interacting with elements of the deck 110. Alternatively, the deck 110 can be coupled to one or more actuators for positioning elements of the deck 110 for interactions with other subsystems.

In the embodiment shown in FIGS. 1A-1C, the deck 110 provides a platform supporting the set of sample processing elements, where the sample processing elements can include disposable and/or reusable components, where the components include containers for containing sample processing materials and/or tools for processing samples (e.g., in relation to fluid handling, in relation to material separation, in relation to heating and cooling, etc.). In embodiments, the deck 110 can support a set of sample processing elements including one or more units of: a reagent cartridge 120, a sample processing cartridge 130, a tool container 140, a heating and cooling subsystem 150, a pumping subsystem 157, a fluid level detection subsystem 159, and a separation subsystem 160. Additionally or alternatively, the deck 110 can include other suitable components associated with an imaging subsystem 190 (e.g., fluorescence detection subsystems, confocal microscope subsystems, spectroscopic detection subsystems, Total Internal Reflection Fluorescence (TIRF) subsystems, Nuclear Magnetic Resonance (NMR) subsystems, Raman Spectroscopy (RS) RS subsystems, etc.).

The sample processing elements can be supported in a co-planar manner by the deck 110, or alternatively at different planes. Preferably, discrete elements supported by the deck are non-overlapping, but alternative embodiments of the deck 110 can support the sample processing elements in an overlapping manner (e.g., for conservation of space, etc., for operational efficiency, etc.).

Details of embodiments, variations, and examples of elements supported by the deck 110 are further described in Sections 2.1.1 through 2.1.8 below.

2.1.1 Deck-Supported Element: Reagent Cartridge

As shown in FIGS. 2A-2D, The deck 110 includes at least one region for supporting a unit of the reagent cartridge 120, where the region functions to position the reagent cartridge 120 relative to portions of the heating and cooling subsystem 150, and separation subsystem 160 described in more detail below. In this regard, the region can include one or more openings, recesses, and/or protrusions for providing interfaces between complementary portions of the reagent cartridge 120 and associated portions of the heating and cooling subsystem 150 and separation subsystem 160, and additionally to promote and maintain alignment between such portions.

The reagent cartridge 120 functions to contain, in one or more compartments, materials for cell capture and/or processing of samples according to one or more workflows for various applications. As such, the reagent cartridge 120 can define a set of storage volumes distributed across a set of domains, where the set of domains can be configured for providing suitable environments for the material contents of each domain. The set of storage volumes can directly contain sample processing materials, and/or can alternatively be configured to receive and maintain positions of individual containers (e.g., tubes, etc.) that contain sample processing materials. The storage volumes of each domain can be distributed in arrays, or otherwise arranged. While the reagent cartridge 120 is described as being supported by the deck 110, variations of the reagent cartridge 120 can alternatively be configured to operate independently of the deck 110.

The reagent cartridge 120 can further additionally or alternatively include aspects described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by this reference.

2.1.2 Deck-Supported Element: Sample Cartridge

As shown in FIGS. 1C and 2A-2D, in embodiments, the deck 110 also includes at least one region for supporting a unit of the sample processing cartridge 130, where the region functions to position the sample processing cartridge 130 relative to portions of the heating and cooling subsystem 150, the pumping subsystem 157, the fluid level detection subsystem 159, and/or the imaging subsystem 190 described in more detail below. In this regard, the region can include one or more openings, recesses, and/or protrusions for providing interfaces between complementary portions of the sample processing cartridge 130 and associated portions of the heating and cooling subsystem 150, the pumping subsystem 157, the fluid level detection subsystem 159, and the imaging subsystem 190, and additionally to promote and maintain alignment between such portions.

The sample processing cartridge 130 functions to provide one or more sample processing regions in which cells are captured and optionally sorted, processed, or otherwise treated for downstream applications, where the downstream applications can be performed on the sample processing cartridge 130 (e.g., on-chip) and/or away from the sample processing cartridge 130 (e.g., off-chip). Portions of the sample processing cartridge 130 can be configured within a single substrate, but can additionally or alternatively include multiple portions (e.g. connected by fluidic pathways) across multiple substrates.

As shown in FIGS. 3A-3D, an example of the sample processing cartridge 130' can include a base substrate 131 to which other elements are coupled and/or in which other elements are defined. Furthermore, in relation to sample processing involving microfluidic elements, the base substrate 131 can function as a manifold for fluid transfer to microfluidic elements, accessing of sample processing volumes at various stages of processing, and transfer of waste materials produced during sample processing. In variations, the base substrate 131 supports one or more of: a sample processing chip 132, an inlet reservoir 133 for receiving sample material (e.g., containing cells, containing particles, etc.) and delivering it into the sample processing chip 132, an access region 134 for accessing one or more regions of the sample processing chip 132, a lid 135 covering the access region and including a gasket 136 providing sealing functions, and a waste containment region 137 for receiving waste material from the sample processing chip 132. Variations of the sample processing cartridge 130 can additionally or alternatively include a region (e.g., second substrate 80), described in more detail below, for retaining functionalized particles for processing target content derived from cells captured at the sample processing cartridge 130. The cartridge may have additional gasketed ports to also connect with off-cartridge pumping system present in the instrument. Variations of the base substrate 131 can, however, include other elements. For instance, as described in more detail below, the base substrate can include one or more openings, recesses, and/or protrusions that provide further coupling with the sample processing chip 132, in order to collectively define valve regions for opening and closing flow through the sample processing chip 132.

Figure 3A:
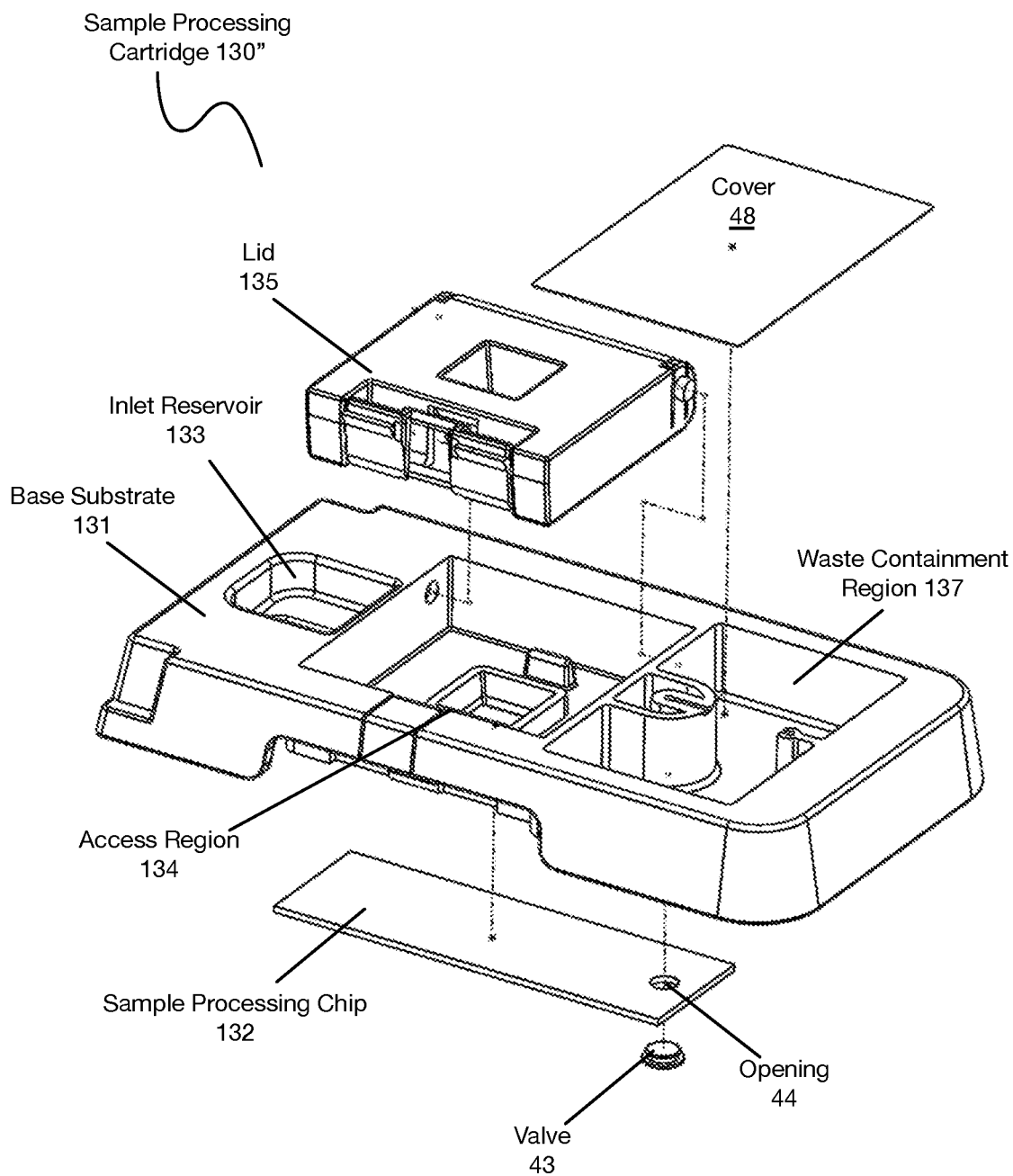
FIGS. 3A-3E depict views of a variation of a sample processing cartridge associated with a system for automated single cell sample processing.
Figure 3B:
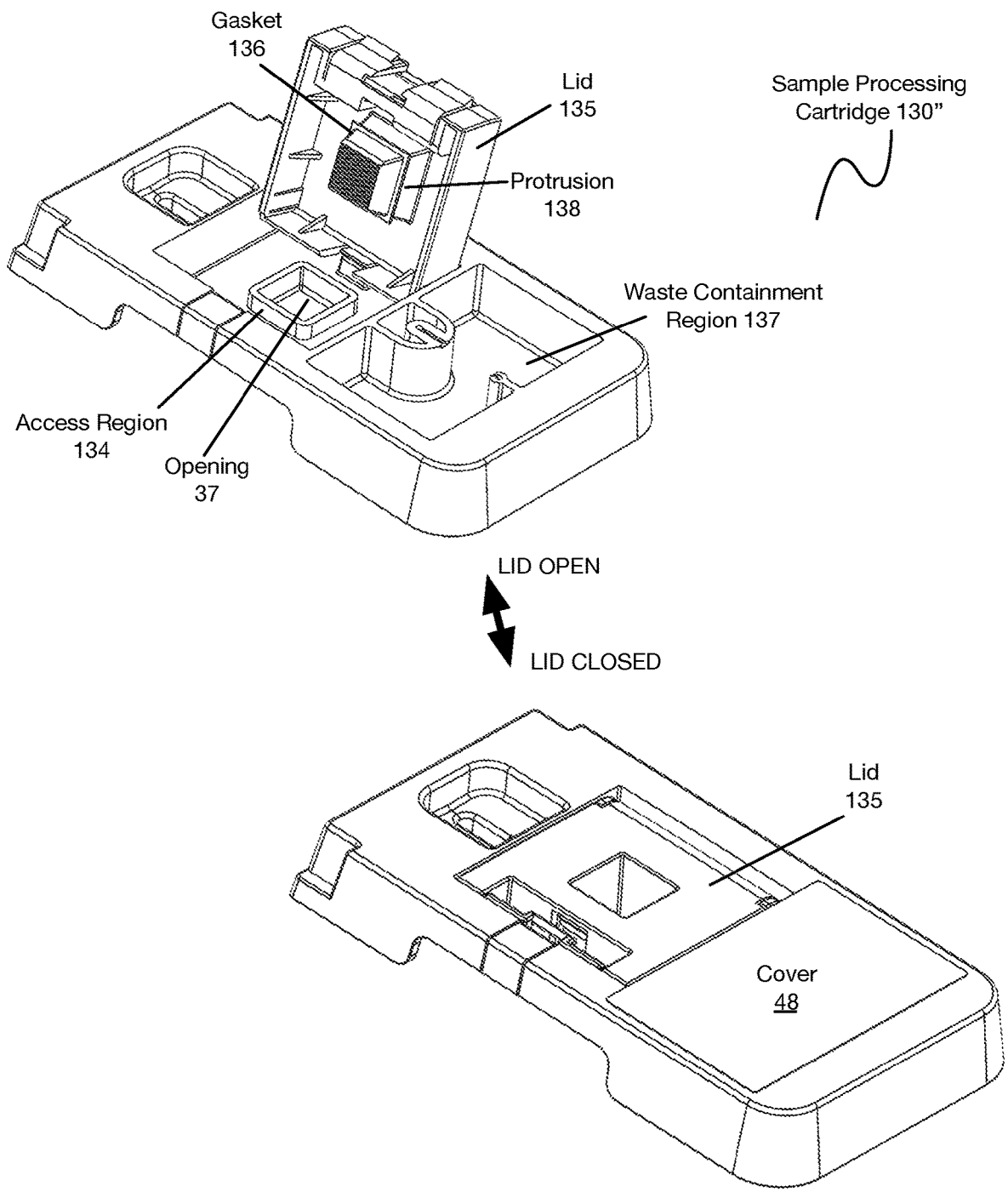
Figure 3C:
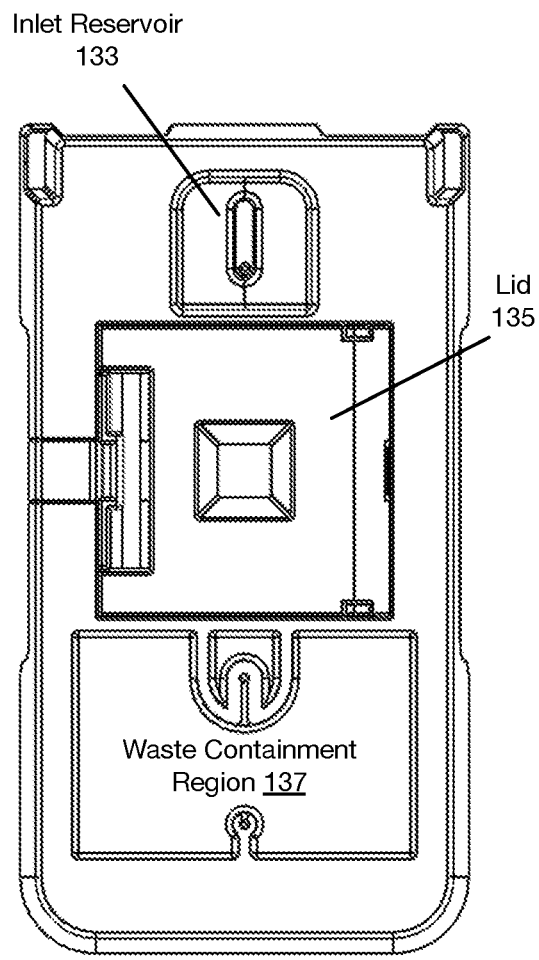
Figure 3C:
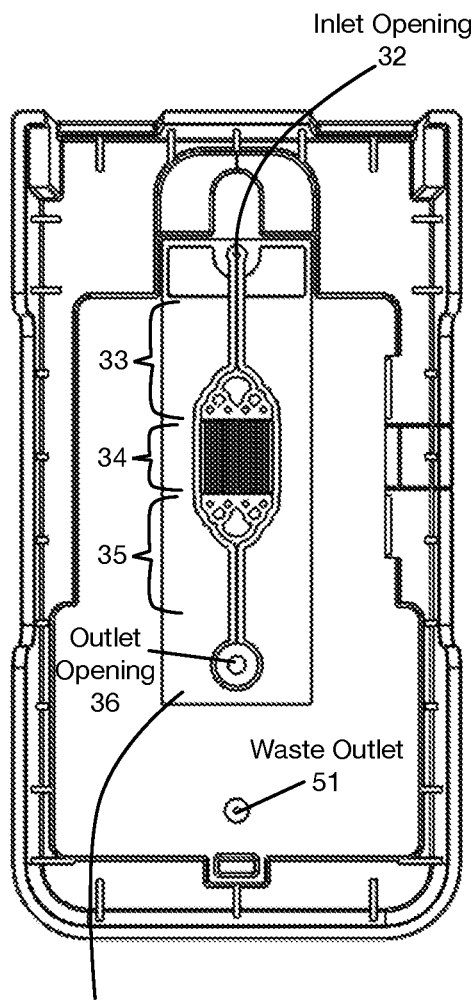

As shown in FIGS. 3A and 3C (bottom view), the sample processing chip 132, (equivalently referred to herein as a microwell device or a slide) defines a set of wells (e.g. microwells). Each of the set of wells can be configured to capture a single cell and/or one or more particles (e.g., probes, beads, etc.), any suitable reagents, multiple cells, or any other materials. In variations, microwells of the sample processing chip 132 can be configured for co-capture of a single cell with a single functional particle, in order to enable analyses of single cells and/or materials from single cells without contamination across wells. Embodiments, variations, and examples of the sample processing chip 132 are described in one or more of: U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference above.

In material composition, the sample processing chip 132 can be composed of microfabricated silicon or glass-fused silica materials, which function to enable higher resolution of the set of wells, enabled, for instance, by defining sharper edges (e.g., thinner well walls, well walls arranged at an angle approaching 90 degrees, etc.) in the set of wells. Material composition can further enable optical interrogation of contents of the sample processing chip 132 (e.g., through a bottom surface, through a top surface), in relation to the imaging subsystem 190 described in more detail below. Materials and fabrication processes described can further enable one or more smaller characteristic dimensions (e.g., length, width, overall footprint, etc.) of the microwell cartridge as compared to conventional chip designs. In specific examples, the sample processing chip 132 is fabricated using deep reactive ion etching (DRIE) techniques, according to specifications associated with one or more of: number of finished devices with acceptable level of defects (e.g., <5%); depth measured to within +/−1 micron of nominal depth (e.g., 25 microns); Rib measured to within +/−1 micron of nominal rib dimensions (e.g., 5 microns). To mitigate any issues during the fabrication, specific examples of the sample processing chip 132 were developed with: a)

determination of resist thickness and lithography required for etching glass substrates with nominal depth of 30 microns with nominal widths of 5 microns between microwells; b) lateral resist erosion and determination of mask bias; c) characterization of vertical taper of microwell side-wall after etching; and d) dicing process optimization to achieve good yield of final devices.

Additionally or alternatively, the sample processing chip 132 can include any other suitable material, such as—but not limited to—a polymer, metal, biological material, or any other material or combination of materials. The sample processing chip 132 may be fabricated by various processes such as precision injection molding, precision embossing, microlithographic etching, LIGA based etching, or by other suitable techniques.

In some variations, one or more surfaces of the set of wells (e.g., bottom surface, side surface, bottom and side surfaces, all surfaces, etc.) can be reacted with oligonucleotide molecules for capture of biomarkers from individual cells into individual microwells. The oligonucleotide molecules present on each and individual microwells may be barcoded to allow biomarkers processed in each microwell to be linked back to a particular well and hence a particular single cell. In one variation, the set of wells includes a set of microwells having hexagonal cross sections taken transverse to longitudinal axes of the wells, as described in one or more of the applications incorporated by reference above.

In one variation, as shown in FIG. 3C, the sample processing chip 132 can include an inlet opening 32, a first fluid distribution network 33 downstream of the inlet opening, for distribution of fluids to a set of microwells 34 (e.g., 1,000 to 10,000,000 wells), a second fluid distribution network 35 downstream of the set of microwells 34, and an outlet opening 36 coupled to a terminal portion of the second fluid distribution network 35, for transfer of waste fluids from the sample processing chip 132. In this variation, the sample processing chip 132 is coupled to a first side (e.g., under-side) of the base substrate 131 (e.g., by laser welding, glue bonding, solvent bonding, ultrasonic welding or another technique). Coupling of the sample processing chip 132 to the side of the base substrate 131 can enable transfer of heat from the heating and cooling subsystem 150 to the set of microwells 34 and/or other regions of the sample processing chip 132, where the heating and cooling subsystem 150 is described in more detail below.

The base substrate 131, as described above, can also include an inlet reservoir 133 (e.g., defined at a second side of the base substrate 131 opposing the first side to which the sample processing chip 132 is coupled). The inlet reservoir functions to receive sample material (e.g., samples containing cells, sample containing barcoded cells, sample containing encapsulated materials, samples containing particles, etc.) and/or sample processing materials from the reagent cartridge 120 described above, for delivery into the inlet opening 32 of the sample processing chip 132. In variations, the inlet reservoir 133 can be defined as a recessed region within a surface of the base substrate 131, wherein the recessed region includes an aperture that aligns with and/or seals with the inlet opening 32 of the sample processing chip 132. The inlet reservoir 133 of the base substrate 131 can interface with upstream fluid containing components and/or bubble mitigating components, as described in one or more of: U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference above.

The inlet reservoir 133 can also be configured to interface with a fluid level detection subsystem 159 supported by or otherwise interfacing with the deck 110, as described in more detail below. In particular, portions of the inlet reservoir 133 can be composed of materials that enable sensing of fluid levels within the inlet reservoir 133 (e.g., by optical interrogation, by pressure sensing, by weight sensing, etc.). For instance, the inlet reservoir 133 can be composed of an optically transparent or translucent material to visible spectrum electromagnetic radiation and/or non-visible spectrum electromagnetic radiation (e.g., by fabrication with different materials, by fabrication to produce thin regions of material at the inlet reservoir 133, etc.), where sensing elements of the fluid level detection subsystem 159 can be configured to interrogate a level of fluid within the inlet reservoir 133 accordingly.

In variations, one or more of the inlet reservoir 133 of the base substrate 131 and the inlet 32 of the sample processing chip 132 can include valve components that can be open or closed by one or more components of the system 100. In a first variation, the inlet reservoir 132 includes an aperture that can be accessed by a pipette tip or any other suitable attachment of a fluid handling subsystem coupled to the gantry 170 (described in more detail below). In some embodiments, the aperture can be closed and therefore prevent fluid from traveling from the inlet reservoir 132 to the sample processing chip 132. The inlet reservoir 132 can, however, be configured in another suitable manner. The opening associated with the inlet reservoir 133 may have a conical shape surface open towards the top allowing interfacing and sealing a pipette tip such that fluid (aqueous solutions or oil or air) may be pumped directly into the microchannel defined in 33 in FIG. 3C.

Figure 4A:
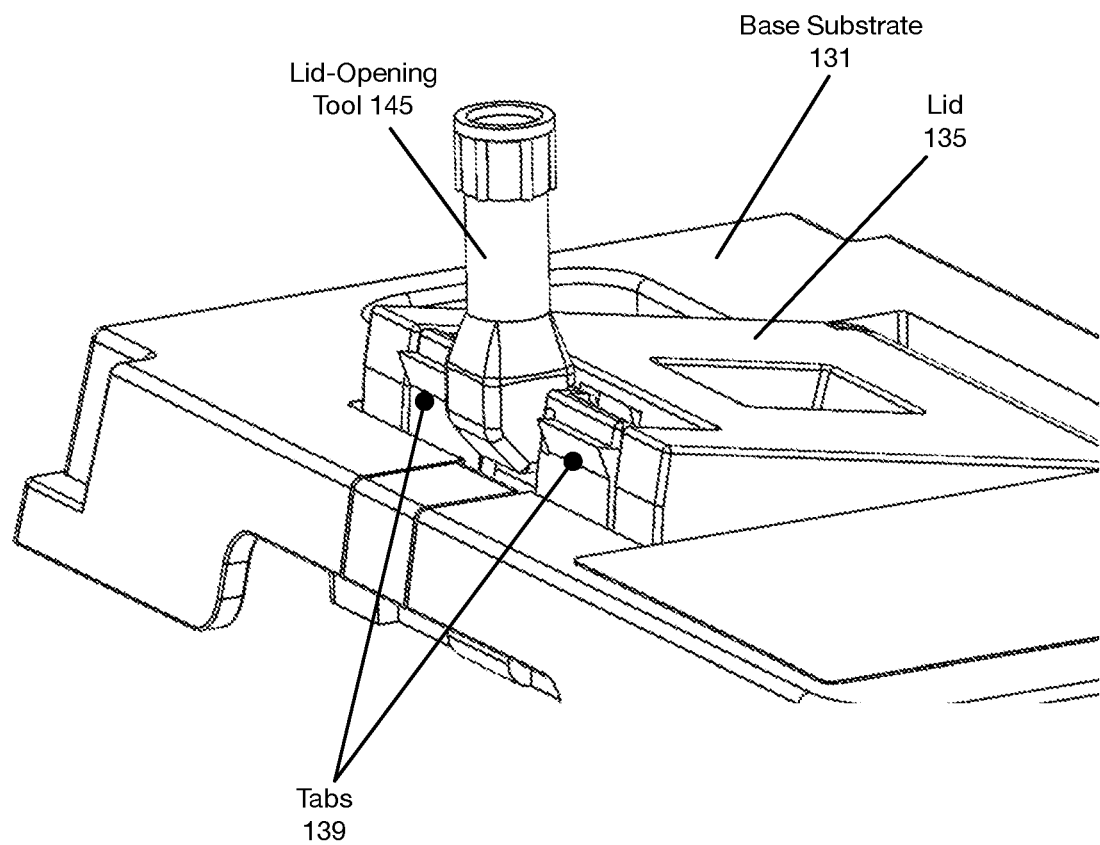
FIGS. 4A-4C depict operation modes of a lid-opening tool associated with the sample processing cartridge shown in FIGS. 3A-3E.
Figure 4B:
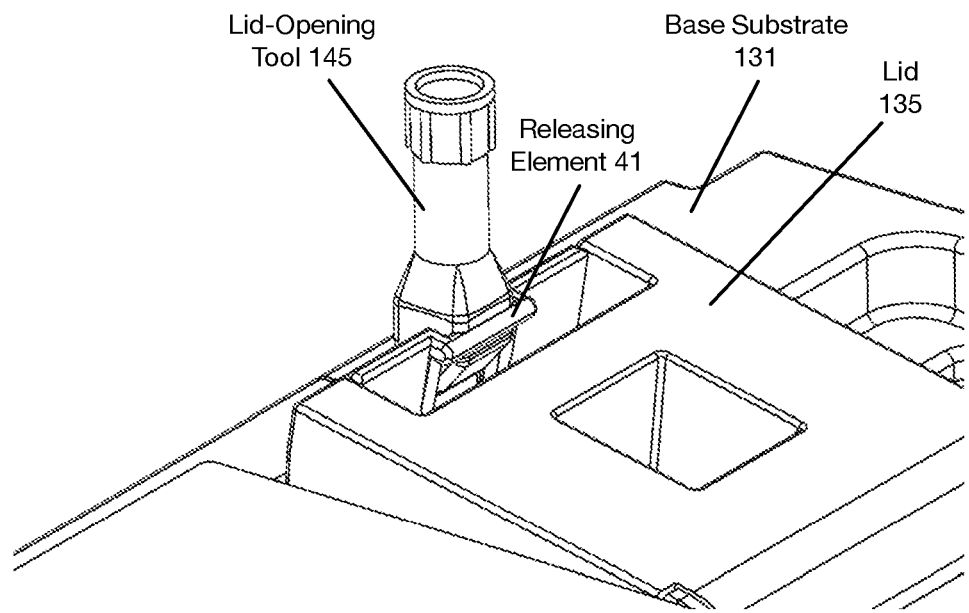

As shown in FIGS. 3A and 3B, the base substrate 131 can also define an access region 134 for accessing one or more regions of the sample processing chip 132, where the access region can allow regions of the sample processing chip 132 to be observed and/or extracted from the sample processing chip 132 at various phases of sample processing. As shown in FIGS. 3A and 3B, the access region 134 can be defined as a recessed region within the base substrate 131, and include an opening 37 aligned with the region of the sample processing chip 132 that includes the set of microwells. The sample processing chip 132 may have as few as 100 microwells to as many as 100 million microwells. As such, in variations wherein the microwell region is open to the environment (e.g., without a covering to seal the wells), the opening 37 of the access region 134 can function as a microwell to provide access to contents of the microwells for observation and/or material extraction (e.g., by magnetic separation, as described in further detail below). The opening 37 can match a morphology and footprint of the microwell region, and in a first variation, as shown in FIG. 4B, can be a square opening. However, in other variations, the opening 37 can have another suitable morphology.

Figure 3D:
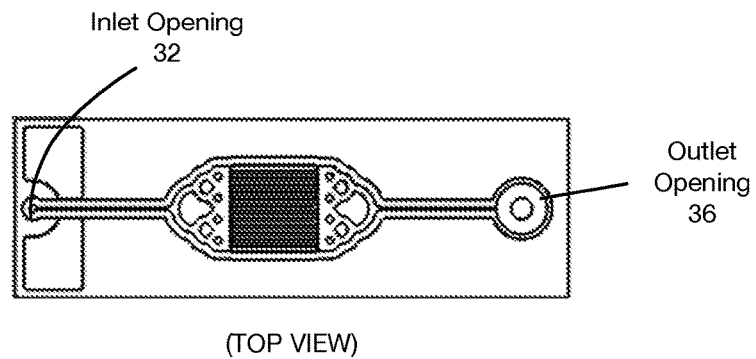
Figure 3D:
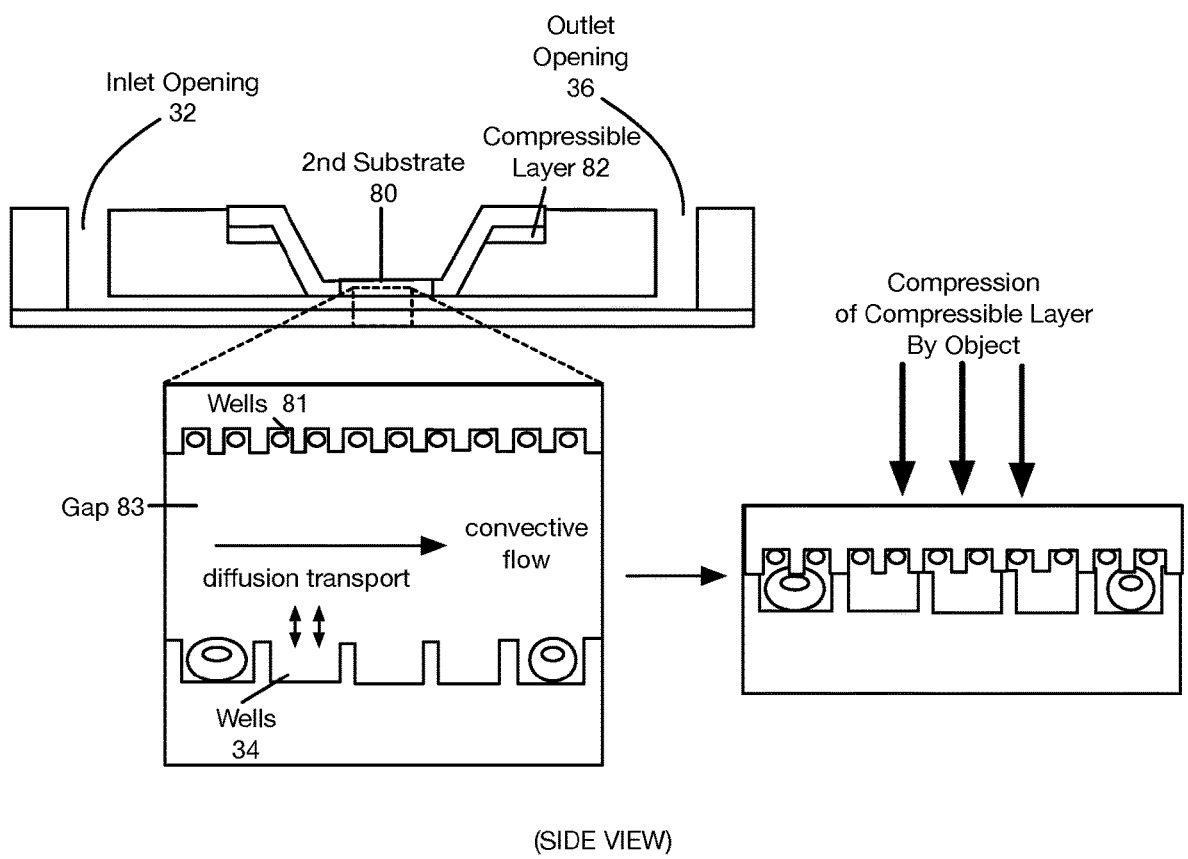

Variations of the sample processing cartridge 130 can additionally or alternatively include a body (e.g., second substrate 80), as shown in FIG. 3D, for positioning functionalized particles relative to cells captured in single-cell format at the sample processing chip 132. The body/second substrate 80 functions to retain or otherwise position functionalized particles for capturing target material released from cells captured at the set of microwells 34 of the sample processing chip 132 in a reliable manner. The body/second substrate 80 can also function to transition between a first mode that provides a gap for fluid flow between the set of wells 34 of the sample processing chip 132 and the second substrate 80 (e.g., during initial capture and/or sample processing steps), and a second mode that compresses the second substrate 80 against the sample processing chip 132 to promote partitioning of contents of the set of wells 34 of the sample processing chip 132 (e.g., after initial capture steps). Even further, the second substrate 80 can function to enable optical interrogation of contents of the set of wells 34 of the sample processing chip (e.g., through access region 134 (e.g., by being composed of materials, such as fused silica or glass that allow for optical interrogation).

The second substrate 80 can be composed of microfabricated silicon or glass-fused silica materials, which function to enable higher resolution of features (e.g., a set of wells of the second substrate 80), enabled, by defining, for instance, sharper edges (e.g., thinner well walls, well walls arranged at an angle approaching 90 degrees, etc.) in the features. In specific examples, the second substrate 80 is fabricated using deep reactive ion etching (DRIE) techniques or other etching techniques. Additionally or alternatively, the second substrate 80 can include any other suitable material, such as—but not limited to—a polymer, metal, biological material, or any other material or combination of materials. In other variations, the second substrate 80 may be fabricated by various processes such as precision injection molding, precision embossing, microlithographic etching, LIGA based etching, or by other suitable techniques.

In variations, the second substrate 80 can include a set of wells 81 configured to face the set of wells 34 of the sample processing chip 132 during operation. The set of wells 81 of the second substrate 80 can be configured to match the arrangement of wells of the sample processing chip 132, in order to appropriately partition the set of wells 34 of the sample processing chip 132 in the second mode of operation where the second substrate 80 is brought closer in contact with the sample processing chip. For retaining functionalized particles, the set of wells 81 of the second substrate 80 can be smaller and greater in number than those of the sample processing chip 132. However, the number and arrangement of wells of the second substrate 80 can be otherwise configured (e.g., the number and arrangement of wells can match between the second substrate 80 and the sample processing chip 132).

In variations, the set of wells 81 of the second substrate 80 can be configured to retain a set of functionalized particles for capturing target material derived from the set of cells captured at the set of wells 34 of the sample processing chip 132 (e.g., post-lysis of the set of cells). In a specific example, the set of functionalized particles are embedded within the set of wells 81 of the second substrate. In a variation of the specific example, the set of functionalized particles are retained within the set of wells 81 of the second substrate by way of a permeable isolation material (e.g., hydrogel) that allows material (e.g., mRNAs, etc.) from lysed cells of the sample processing chip 132 to diffuse past the isolation material and toward the functionalized particles of the second substrate. In variations, the set of functionalized particles can include silica beads processed with binding moieties (described in more detail in Section 3 below) for binding target material from the set of cells; however, in other variations, the set of functionalized particles can have another suitable composition and configuration.

In variations, the second substrate can be configured to be complementary with the access region 134 described above, thereby positioning the seconds substrate 80 into alignment with the microwell region of the sample processing chip 132. In supporting the operation modes, the second substrate 80 can be separated from the sample processing chip 132 and/or the base substrate 131 of the sample processing cartridge 130 by a compressible layer 82 (e.g., composed of elastomer), such that, in the first operation mode, the compressible layer 82 is uncompressed to produce a gap 83 that allows fluid to flow across the set of wells 34 of the sample processing chip 132, and between the sample processing chip 132 and the second substrate. Then, in the second operation mode, the compressible layer 82 is compressed against the sample processing chip 132 to partition contents of the set of wells 34 of the sample processing chip and/or allow specific capture of cell-derived content toward the functionalized particles of the second substrate 80.

In a specific example, as shown in FIG. 3D, the second substrate 80 is composed of silicon and contains tens of millions of silica beads embedded on the surface facing the sample processing chip 132, in hexagonal-packed microwells (e.g., 3 microns wide by 3 micron deep). However, the microwells of the second substrate 80 can have other suitable morphology (e.g., polygonal in cross section, non-polygonal in cross section, etc.). In the example, the second substrate 80 is positioned over (e.g., aligned with and facing) the set of wells 34 of the sample processing chip 132 by way of access region 134, and an elastomeric compressible layer 82 is used for coupling and positioning the second substrate 80 such that the gap between the second substrate 80 and the sample processing chip 132 can be adjusted (e.g., by the instrumentation of the gantry 170, by instrumentation of the base 180, etc.) to allow: a first operation mode with creation of a gap of approximately 250 microns between the second substrate 80 and the sample processing chip 132, such that cell suspensions or reagents can be flow across the set of wells of the sample processing chip 132; and a second operation mode in which the second substrate 80 is compressed against the sample processing chip 132 such the different cell containing microwells are partitioned and isolated from each other. In more detail, movement of the second substrate 80 relative to the sample processing chip 132 can be performed by an actuator-heater subsystem (described in more detail below) which can apply a desired force (e.g., less than 1 lb. of force, greater than or equal to 1 lb. of force, etc.) and also provide defined and control heating to the sample processing cartridge 130 for various reactions.

In the specific example, a dense solution of 2-micron diameter functionalized silica particles is dispersed in a hydrogel solution containing polymerization compounds (e.g., photo-initiators, chemical polymerizers, etc.), and delivered to the surface of the second substrate 80 defining the set of wells 81. During processing, excess silica particles are washed away and the process is repeated until the set of wells 81 are fully saturated with beads. Due to specific size and geometry, only one particle can be captured in each microwell of the second substrate 80 of the specific example. Excess liquid and particles are removed off by smearing a flat surface over the beads and the hydrogel is polymerized (e.g., by light, by chemical reaction, etc.), thereby retaining the silica particles in position at the second substrate 80. The composition of the hydrogel is optimized to facilitate diffusion of mRNA molecules, PCR reagents, and enzymes, and other material through the hydrogel and toward the functionalized particles.

In variations, however, wells of the sample processing chip 132 can serve as a region for positioning functionalized particles relative to cells captured in single-cell format at the sample processing chip 132, such that target cells are co-captured with functionalized particles within individual wells of the sample processing chip 132 (e.g., as in U.S. application Ser. No. 16/816,817, filed 12 Mar. 2020; as in U.S. application Ser. No. 16/564,375 filed 9 Sep. 2019; as in U.S. application Ser. No. 16/115,370, filed 28 Aug. 2018, as incorporated by reference above).

As shown in FIGS. 3A-3C, the base substrate 131 can include or otherwise couple to a lid 135 covering the access region 134, where the lid 135 can include a gasket 136 providing sealing functions, and where the lid 135 functions to transition the access region 134 between open and closed modes, thereby preventing evaporative sample loss and/or contamination of contents of the sample processing chip 132 during operation. The lid 135 can additionally or alternatively function to protect the contents of the microwells or other processing regions of the sample processing chip 132 from debris, enable a processing of the contents of the sample processing chip 132 (e.g. by isolating regions from the ambient environment), initiate the start of a protocol (e.g., by opening to accept reagents from a pipettor), prevent user manipulation of the sample processing chip 132 (e.g., by closing after all necessary reagents have been added), define (e.g., with the lid 135) part or all of a fluid pathway, cavity, or reservoir (e.g. serve as the top surface of a fluidic pathway between the inlet and the set of microwells, serve as a boundary of a fluid pathway adjacent the microwell region, serve as the top surface of a fluidic pathway between the set of wells and the waste chamber, etc.), or perform any other suitable function. The lid 135 can cover and retain the position of the second substrate 80 within the access region 134, in variations where the sample processing cartridge 130 includes a second substrate 80; however, the lid 135 can alternatively be omitted in variations of the sample processing cartridge 130 can include a second substrate 80.

As shown in FIG. 3B, in at least one variation, the lid 135 can be complementary in morphology to features of the access region 134, such that the lid 135 mates with the access region 134, while providing a gap with the sample processing chip 132. Additionally, in variations (shown in FIGS. 3B and 3C), the lid 135 can be substantially flush with the base substrate 131 at a top surface when the lid 135 is in the closed position. However, the lid 135 can be morphologically configured in another suitable manner.

In variations, a protrusion 38 of the lid 135 can interface with the opening 37 of the access region 134, thereby substantially preventing access to the opening 37 when the lid is in the closed position. As shown in FIG. 3B, in some variations, the protrusion 38 can have a base (or other region) surrounded by a gasket 136, which functions to seal the opening 37 of the access region 134 in the closed position of the lid 135. Variations of the lid 135 can, however, omit a gasket and promote sealing of the access region 134 in another suitable manner. In another embodiment, the entire bottom surface of the lid that comes closest to the microwells in the sample processing chip 132 can be an elastomeric substrate (e.g., flat elastomeric substrate) allowing the elastomeric lid to cover the microwells, thereby preventing any evaporative or diffusive loss of molecules during thermocycling in each of the microwells.

Figure 3E:
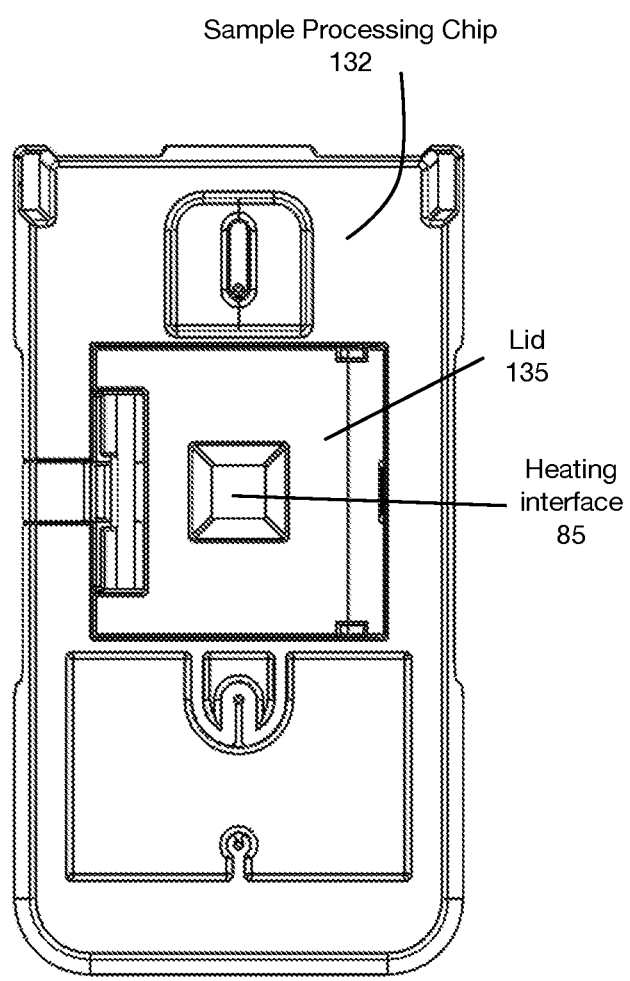

In some variations, as shown in FIG. 3E, the lid 135 can include a heating interface 85 (e.g., heating body that actively and/or passively transmits heat to the sample processing chip 132, with or without a temperature sensor), thereby allowing controlled heating of the sample processing chip 132 during processing).

Figure 4C:
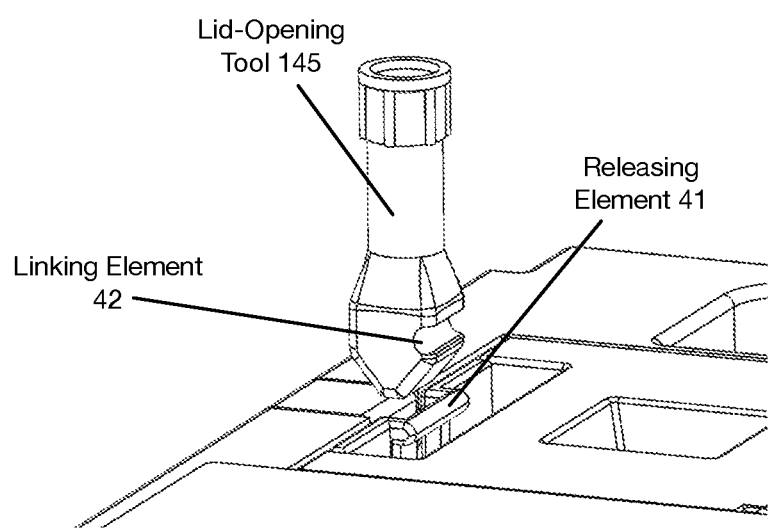

In some variations, the lid 135 can include a locking or latching mechanism that allows the lid 135 to be maintained in the closed position with the base substrate 131 until the locking/latching mechanism is released. In the variation shown in FIGS. 4A-4C, a peripheral portion of the lid 135 can include a one or more tabs 39 that interface with corresponding tab receiving portions of the base substrate 131, where, the tabs 39 are configured to flex when pushed into the base substrate 131 until they interface with the tab receiving portions of the base substrate 131 and return from a flexed configuration to a latched state. Additionally or alternatively, in the variation shown in FIGS. 4A-4C, the locking/latching mechanism can include a releasing body 41 (e.g., bar, recess, hook, etc.) that can be interfaced with in order to release the tab(s) 39 from the tab receiving portions, and transition the lid 135 from the closed mode to the open mode in relation to the base substrate 131. As such, the lid 135 provides the lid an open mode in which the access region 134 is uncovered and a closed mode in which the access region 134 is covered. In the variation shown in FIGS. 4A-4C, the releasing element 41 includes a bar that is recessed away from the access region 134 of the base substrate 131, where the bar can be reversibly coupled to a lid-opening tool 145. In variations, the lid-opening tool 145 can include a first region (e.g., first end) that interfaces with a an actuator (e.g., actuating tip, pipettor of a fluid handling subsystem coupled to the gantry 170 described below, etc.), and a second region (e.g., second end) including a linking element 42 configured to interface with the releasing element 41 of the lid 135. Then, with movement of the pipettor/pipette interface, the lid-opening tool 145 can be configured to pull on the releasing element 41 and/or push on the lid 135 in order to transition the lid between open and/or closed modes. As such, in relation to fluid handling elements coupled to the gantry 170 described below, the system 100 can provide operation modes for: coupling a lid-opening tool 145 to an actuator (e.g., coupled to a gantry 170), the lid-opening tool including a linking element 42; moving the lid-opening tool into alignment with a releasing element 41 of the lid 135, reversibly coupling the linking element 42 with the releasing element 41; and applying a force to the releasing element 41, thereby releasing the lid 135 from a latched state and transitioning the lid 135 from a closed mode to an open mode. In order to effectively apply an unlatching force (e.g., by the actuator (e.g., coupled to a gantry 170), the base substrate 131 can be retained in position (e.g., by retention elements described in Section 2.1.4, by retention elements of the heating and cooling subsystems, by retention elements of the fluid level detection subsystem, by retention elements of the deck, etc.) which passively or actively apply counteracting forces against the unlatching forces applied through the lid-opening tool 145.

In variations, however, the locking/latching mechanism can additionally or alternatively include or operate by way of: a lock-and-key mechanism, magnetic elements, or another suitable mechanism. Furthermore, in alternative variations, the lid 135 can include another lid actuator, for instance, including a motor that rotates the lid about an access parallel to a broad surface of the sample processing cartridge 130. The actuator can additionally or alternatively be configured to translate the lid 135 (e.g. slide the lid 135 parallel to a broad surface of the sample processing cartridge 130, translate the lid 135 perpendicular to the broad surface, etc.) or otherwise move the lid 135 to selectively cover and uncover one or more predetermined regions (e.g. the set of microwells). As such, the lid 135 can be configured to operate in an automated or semi-automated fashion, such that the lid 135 automatically closes upon one or more triggers (e.g., cell capture protocol is initiated by a user, cell processing protocol is initiated by a user, all reagents for a selected protocol have been added from the reagent cartridge 120, etc.) and opens upon one or more triggers (e.g., cell capture protocol has been completed, upon user request, it has been determined that the cells are viable, it has been determined that single cells have been captured, etc.). Additionally or alternatively, operation of the lid 135 can be initiated and/or completed by a user, operated according to a schedule or other temporal pattern, or otherwise operated.

As shown in FIGS. 3A-3C, the base substrate 131 can also include a waste containment region 137 for receiving waste material from the sample processing chip 132. The waste containment region 137 can also function to maintain desired pressures (e.g., vacuum pressures, etc.) within the sample processing chip 132, thereby enabling flow of liquid from the inlet reservoir 133 through the sample processing chip 132 and to the waste containment region 137. The waste containment region 137 can be defined as a volume (e.g., recessed into the base substrate 131, extending from the base substrate 132, coupled to an outlet of the base substrate 131, etc.) for receiving waste or other materials from the sample processing chip 132. In the variation shown in FIGS. 3A-3C, the waste containment region 137 is defined at a side of the base substrate 131 opposing the side to which the sample processing chip 132 is coupled, such that waste from the sample processing chip 132 is pushed or pulled upward into the waste containment region 137 by forces of the pumping subsystem 157 described in more detail below. However, the waste containment region 137 can additionally or alternatively be configured in another suitable position relative to the base substrate 131 and the sample processing chip 132, in order to receive waste.

The waste containment region 137 can have a volumetric capacity of 10-100 mL or another suitable volumetric capacity.

As shown in FIGS. 3A-3C, the waste containment region 137 can include a cover 48 (e.g., a cover that is approximately co-planar with the lid 135), which facilitates containment of waste within the waste containment region 137. Alternatively, the waste containment region 137 may not include a cover. Furthermore, as shown in FIG. 3C, examples of the waste containment region 137 can include a pump outlet 51 distinct from the cover, where the pump outlet 51 can allow the residual air in the waste chamber to be pressurized by an off-cartridge pump (e.g., by pumping mechanisms, etc.); however, variations of the waste containment region 137 can alternatively omit a waste outlet.

In relation to the waste containment region 137, the system 100 can further include a valve 43 configured to allow and/or prevent flow from the sample processing chip 132 to the waste containment region 137. The valve 43 can interface with the outlet opening 36 of the sample processing chip 132 described above, in order to enable and/or block flow out of the outlet opening 36 and into the waste containment region 137. The valve 43 can have a normally open state and transition to a closed state upon interacting with a valve-actuating mechanism. Alternatively, the valve 43 can have a normally closed state and transition to an open state upon interacting with a valve-actuating mechanism.

Figure 5A:
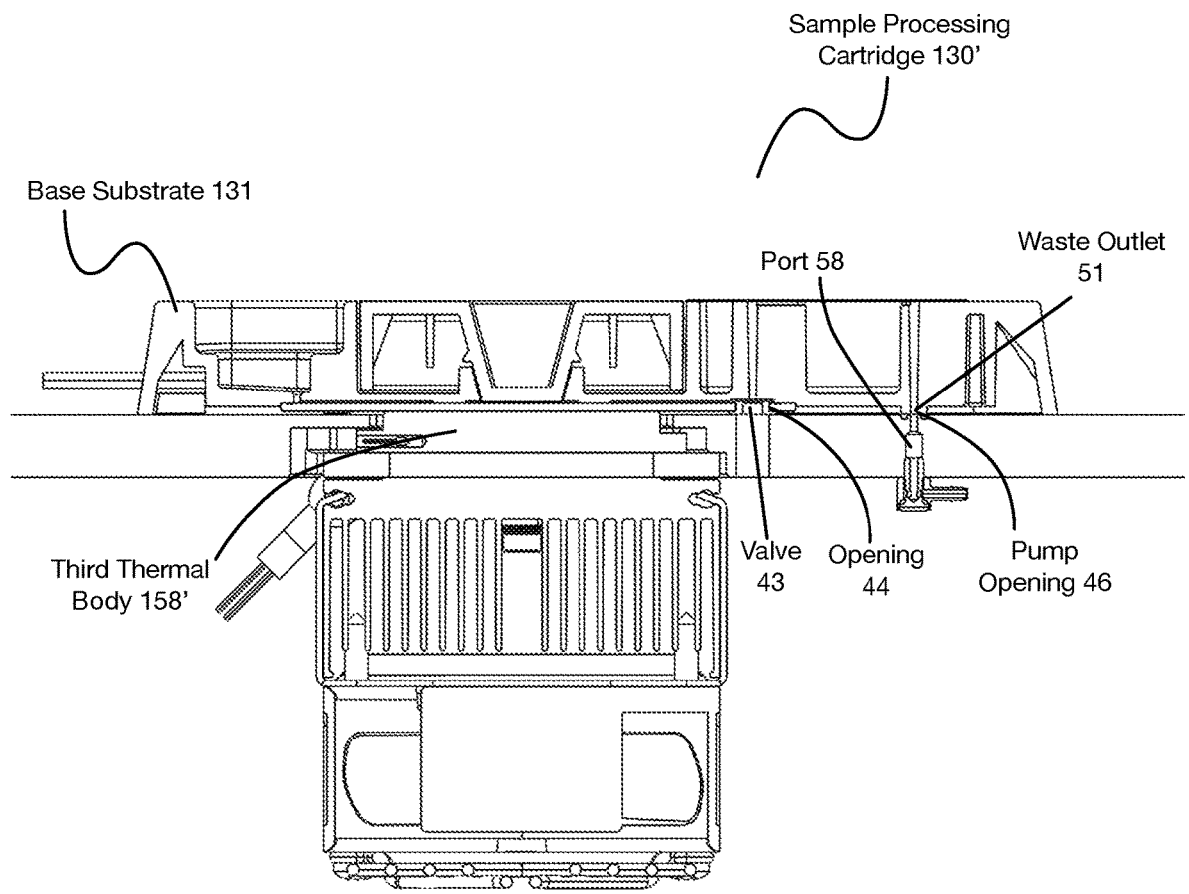
FIGS. 5A-5B depict operation modes of a valve and heating subsystem associated with the sample processing cartridge shown in FIGS. 3A-3E.
Figure 5B:
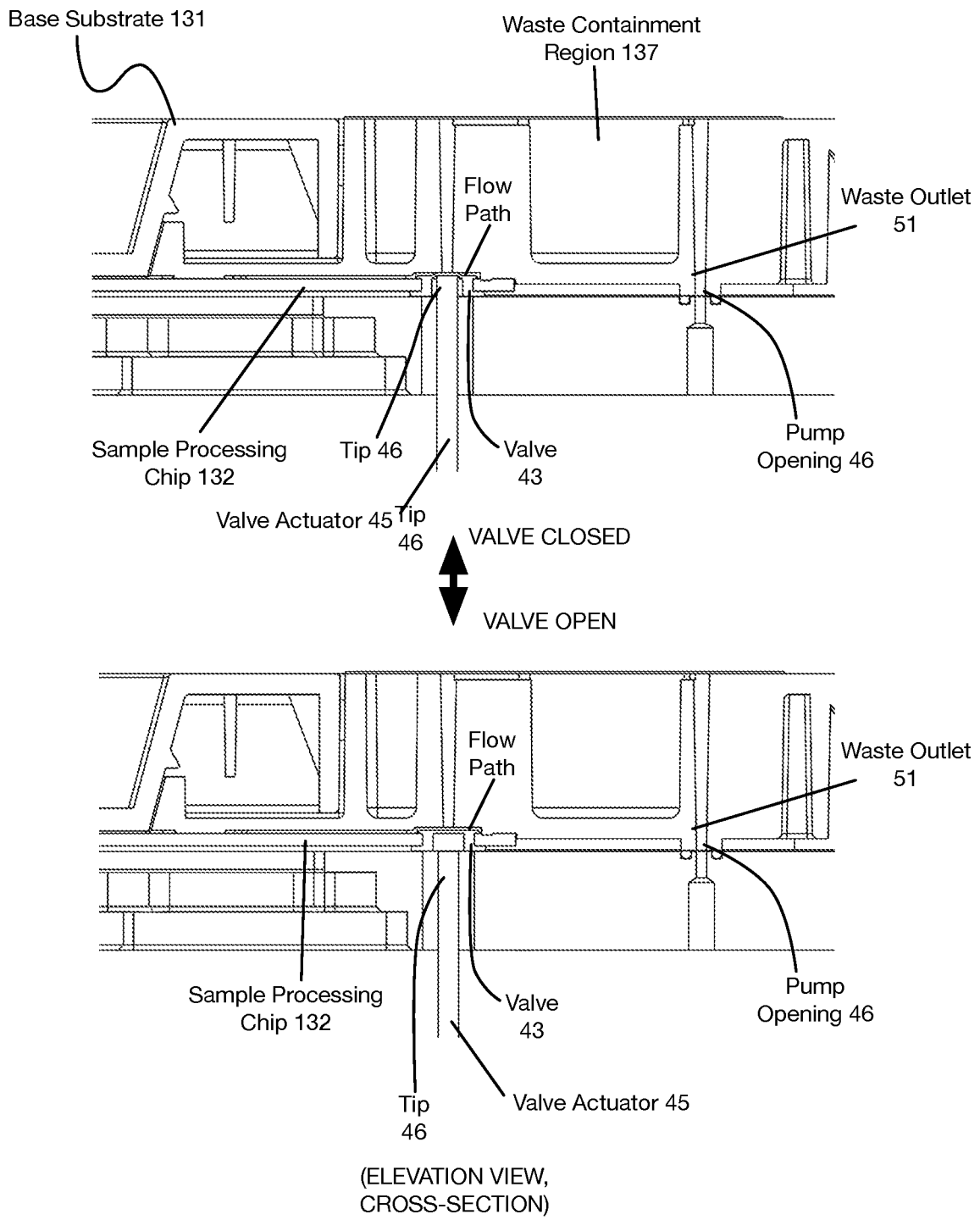

In the variation shown in FIGS. 3A and 5A-5B, the valve 43 comprises an elastomeric body and is configured to couple the sample processing chip 132 to the base substrate 131 through an opening 44 of the sample processing chip 132 that aligns with a corresponding valve-receiving portion of the base substrate 131. In this variation, a transitionable portion of the valve 43 is configured to be positioned along a flow path from the outlet opening 36 of the sample processing chip 132 to the inlet of the waste containment region 137 of the base substrate 132 (e.g., along a flow path from the microwell region to an outlet of the sample processing chip into a waste containment region of the sample processing cartridge). In an example the opening 44 of the sample processing chip 132 is contiguous with the outlet opening 37 of the sample processing chip 132; however, in other variations, the outlet opening 37 and the opening 44 may be displaced from the each other and connected by another microfluidic channel. As such, closure of the valve 43 can block flow from the outlet opening 37 into the waste containment region 137, and the valve 43 can be opened to allow flow from the outlet opening 37 into the waste containment region 137.

In a variation shown in the cross sectional images of the base substrate 131 shown in FIGURES SA-5B, a valve actuator 45 can access the base substrate 131 from below (e.g., from below the deck), and pass through a channel or other recess/opening of the base substrate 132 in order to interact with the valve 43. In particular, when a tip 46 (aligned with the opening into the base substrate) of the valve actuator 45 pushes against the valve (e.g., a elastomeric membrane of the valve 43), as shown in FIG. 5B (top), the valve 43 can transition to a closed state in order to fluidically decouple the outlet opening 37 of the sample processing chip 132 from the waste containment region 137. Additionally or alternatively, as shown in FIG. 5B (bottom), removal of force by the valve actuator 45 can remove pressure from the valve 43 and transition it to an open state to fluidically couple the outlet opening 36 of the sample processing chip 132 from the waste containment region 137. As such, the valve actuation subsystem includes an engaged mode wherein the tip extends into the valve opening to deform the elastomeric valve, thereby closing the flow path, and a disengaged mode wherein the tip is retracted, thereby opening the flow path. However, the valve 43 can additionally or alternatively be configured in another suitable manner.

In other variations, the system can include a similar mechanism for coupling a valve to other flow paths of the sample processing chip 132 and/or to the base substrate 131.

Variations of the base substrate 131 can, however, include other elements. For instance, as described in more detail below, the base substrate 131 can include one or more openings, recesses, and/or protrusions that provide further coupling with the sample processing chip 132, in order to promote or inhibit flow through the sample processing chip 132. For instance, as shown in FIGURE SA, the base substrate 131 can include a pump opening 46 that couples the base substrate 131 to a pumping element of the pumping subsystem 157 (e.g., through deck 110), in order to drive and/or stop fluid flow through the sample processing chip 132.

The base substrate 131 of the sample processing cartridge 130 can, however, include other suitable elements.

2.1.3 Deck-Supported Element: Tool Container

Figure 2A:
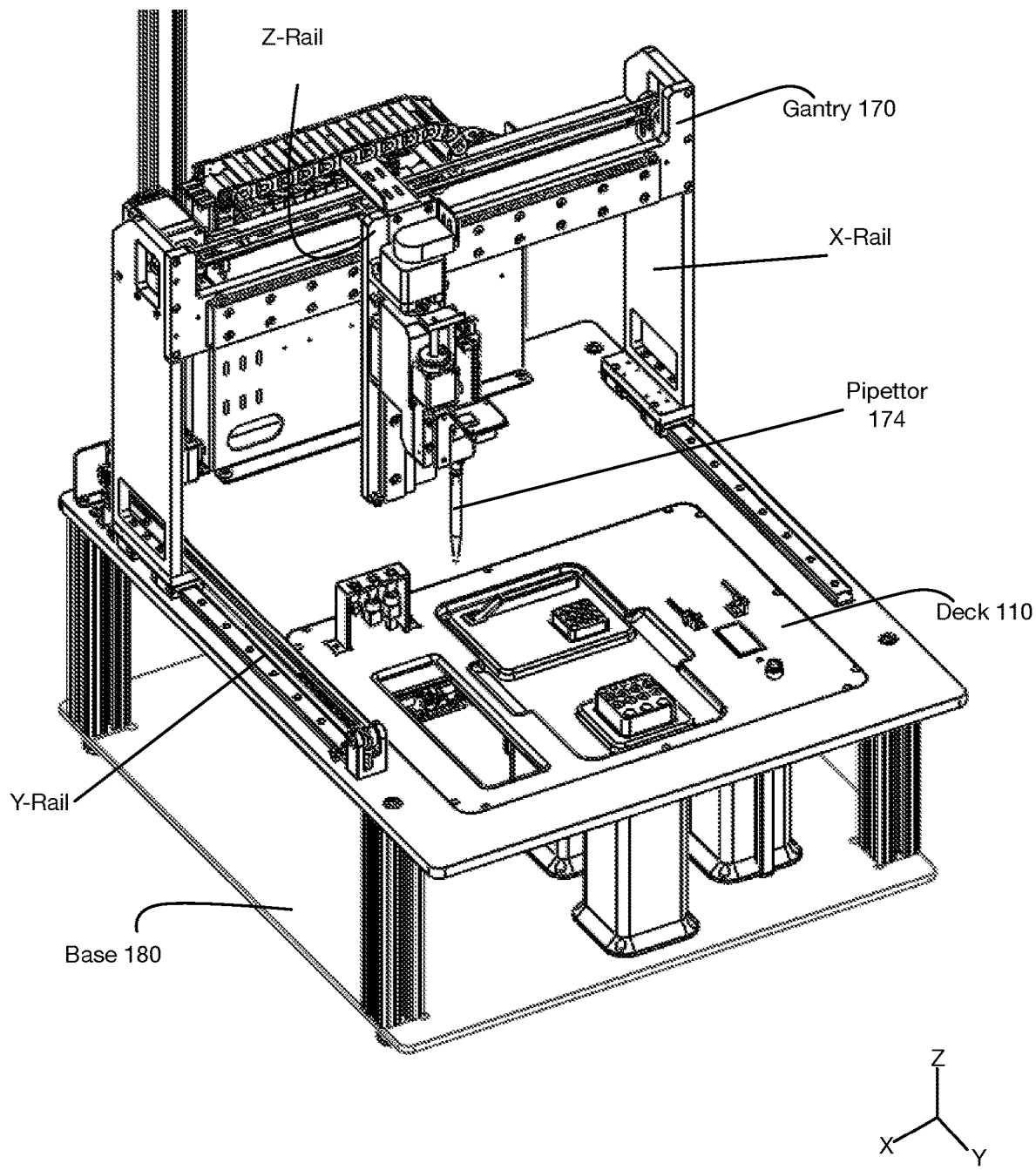
FIGS. 2A-2D depict views of a variation of the system shown in FIGS. 1A-1D.
Figure 2B:
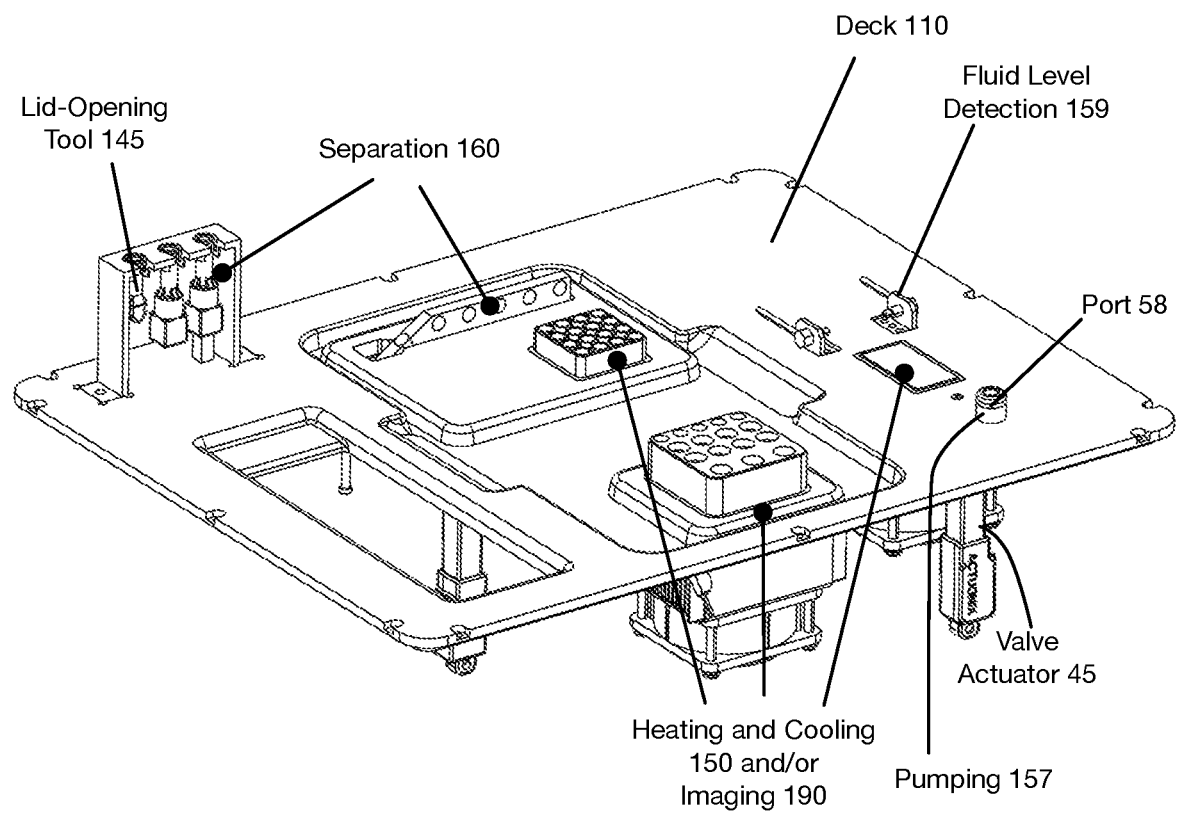
Figure 2C:
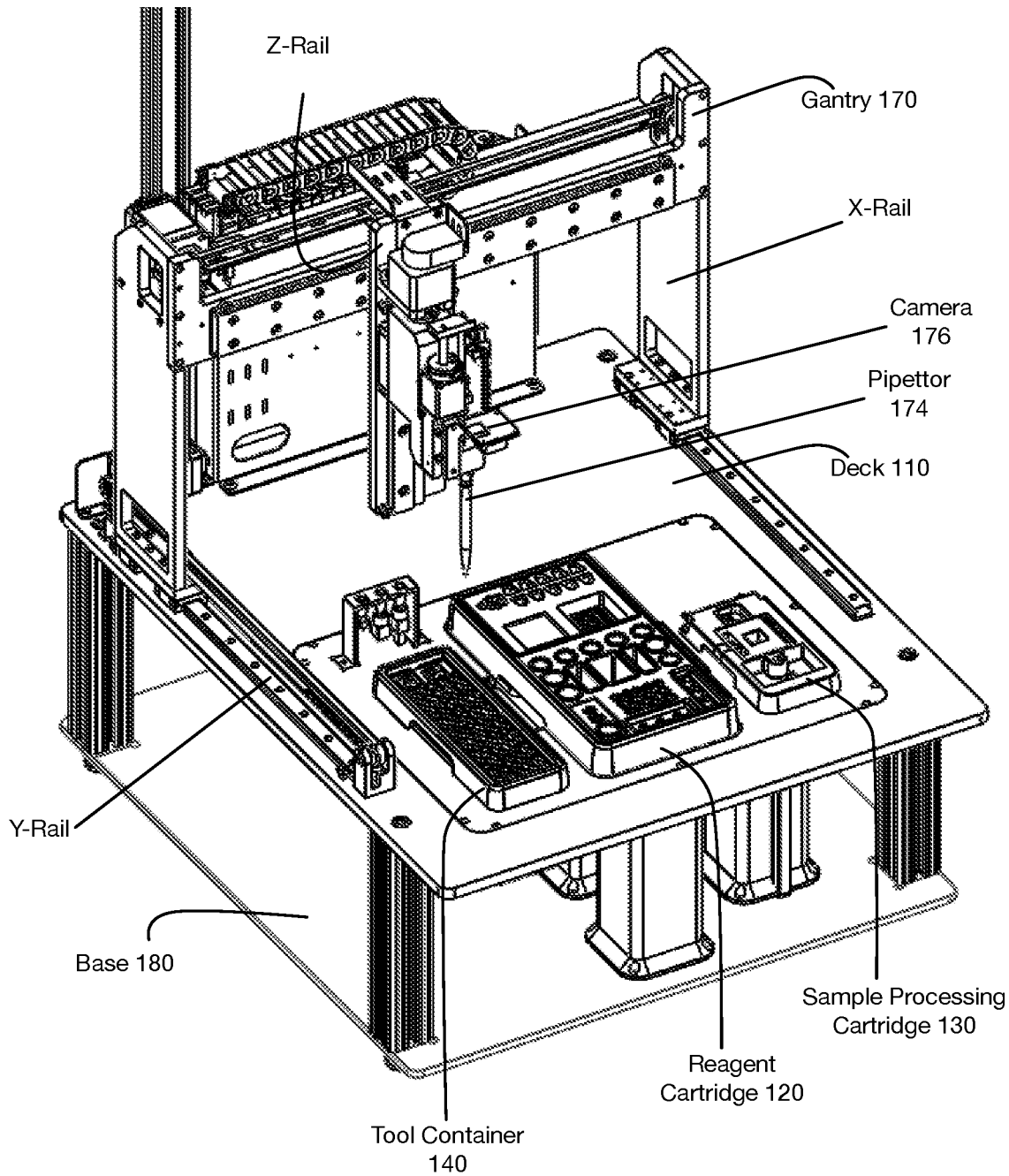
Figure 2D:
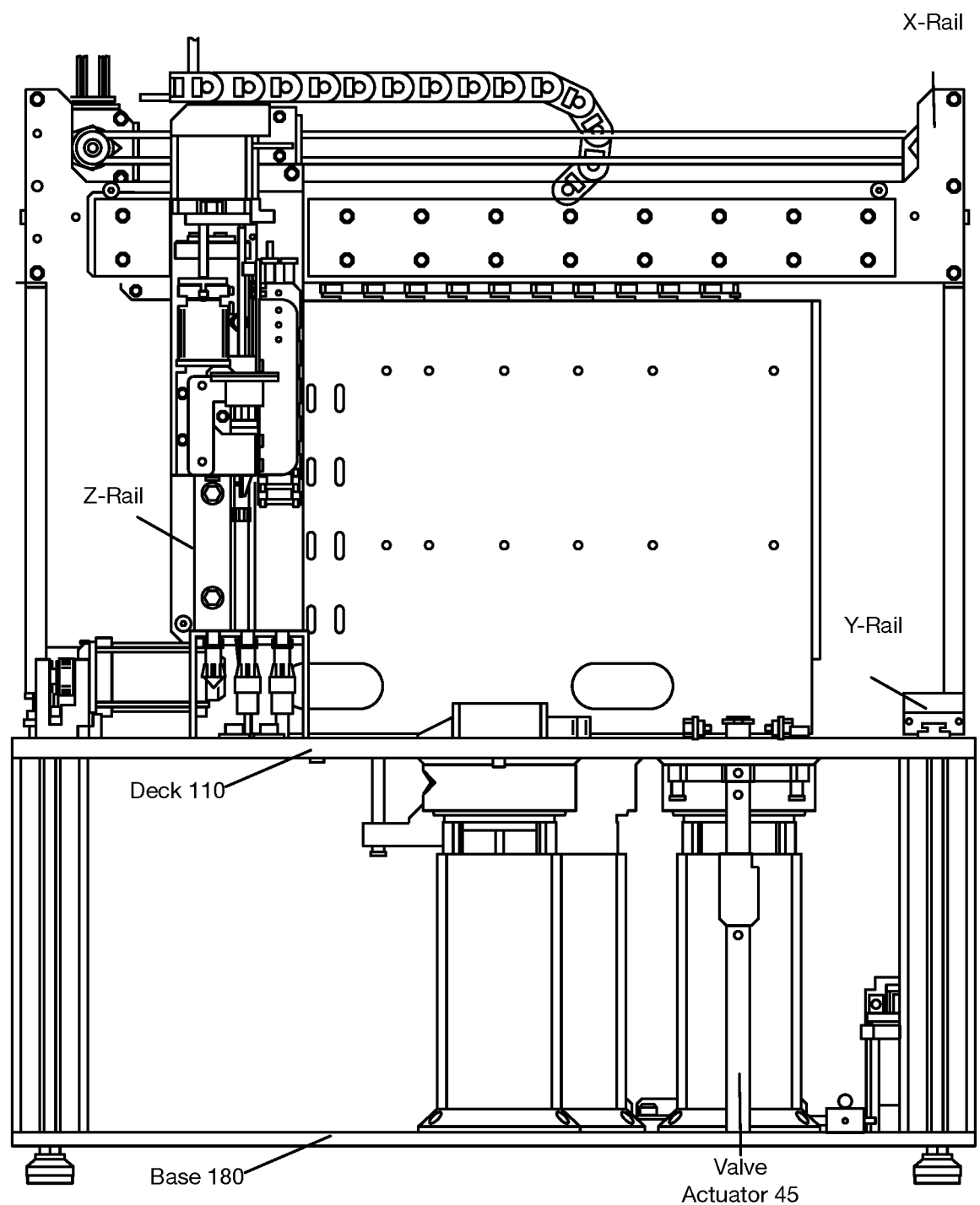

As shown in FIGS. 2A and 2B, the deck 110 includes at least one region for supporting a unit of the tool container 140, where the region functions to position the tool container 140 relative to fluid handling apparatus of the gantry 170 described below.

The tool container 140 functions to contain, in one or more compartments, one or more units of various tools for fluid aspiration, fluid delivery, separation of target material from non-target material of a sample and/or other tools, according to one or more workflows for various applications. As such, the tool container 140 can facilitate transfer and/or mixing of reagents with sample, fluidically couple and/or decouple elements at various regions of the deck 110, or otherwise interact with one or more components of the system 100.

While the tool container 140 is described as being supported by the deck 110, variations of the tool container 140 can alternatively be configured to operate independently of the deck 110.

The tool container 140 can further additionally or alternatively include aspects described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

2.1.4 Deck-Supported Element—Imaging Subsystem

Figure 6:
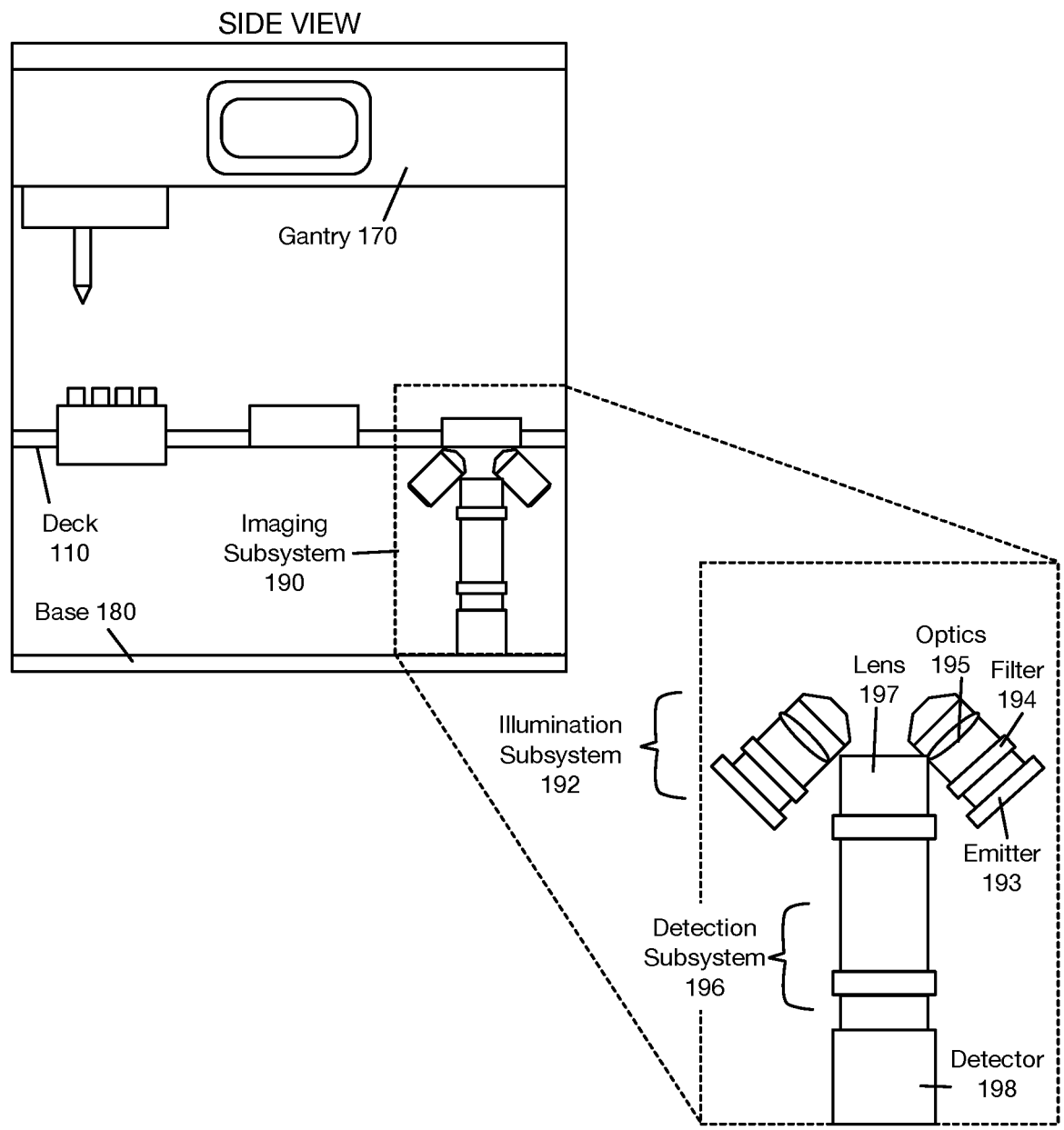
FIG. 6 depicts an embodiment of an imaging subsystem.

As shown in FIGS. 1A and 6, the system 100 can include an imaging subsystem 190, which functions to enable performance of real-time detection of contents of the sample processing chip 132 (e.g., from all microwells of the sample processing chip 132 simultaneously). As such, the imaging subsystem 190 can provide the ability to detect 100-fold or 1000-fold or more cells than the current state of the art systems in real-time. Additionally, the imaging subsystem 190 functions to provide a low-cost, integrated solution (e.g., with a small footprint size (<½ cubic foot) so that it can be easily integrated into a benchtop system for sample preparation. In more detail, the imaging subsystem 190 can provide a solid-state, fully integrated detection system capable of looking at the entire region(s) of interest of the sample processing chip 132, to allow for rapid, real-time detection (e.g., fluorescence-based detection) of events happening in the cells as different reagents are pumped past the cells and/or processed with specific thermal reactions (e.g., temperature incubations).

In embodiments, the imaging subsystem 190 comprises an illumination subsystem 192 and a detection subsystem 196, where the illumination subsystem 192 functions to illuminate the sample processing chip 132 and/or its contents (e.g., with excitation of contents associated with various processing steps and reactions). The detection subsystem 196 functions to provide real-time scanning of the entire region(s) of interest of the sample processing chip 132, in order to enable detection in real time. In variations, the imaging subsystem 190 can further include an imaging controller 199, which functions to synchronize or otherwise coordinate illumination and detection functions of the imaging subsystem 190. As shown in FIGS. 1A and 6, the imaging subsystem 190 can be at least partially supported by the base 180 and configured to interface with the deck 110 in relation to illumination and/or detection of a target object at a sample processing cartridge 130 at the deck 110; however, the imaging subsystem 190 can be otherwise configured.

In a specific example, as shown in FIG. 6, the illumination subsystem 192 includes: a set of emitters 193 (e.g., light emitting diodes, LEDs) coupled with a set of filters 194 (e.g., band pass interference filters), and a set of optical elements 195 to uniformly illuminate the entire surface area of sample processing chip (e.g., a 1 cm$^2$ target region, a target region less than 1 cm$^2$, a target region greater than or equal to 1 cm$^2$). In the specific example, light from an emitter of a specific color is collimated by way of the set of optical elements, and transmitted at an angle to illuminate the target area. In the specific example, the emitters (e.g., LEDs) are selected to have on the order of one watt of optical power to provide adequate system sensitivity; however, in other variations, the emitters can have another suitable power output. In the specific example, the illumination subsystem 192 includes custom concentric holders coupled to subunits (e.g., LED, band pass filter, excitation filter, and lens(es)) of the illumination subsystem 192, thereby configuring each subunit, corresponding to each emitter color, separately. In the specific example, the dyes selected for the 4-color fluorescence detection system are DAPI (Ex-365 nm), FITC (Ex-475 nm), Alexa Fluor 568 (Ex-568 nm) and Alexa Fluor 647 (Ex-635 nm); however, other emitter wavelengths, filters, and dyes can be selected depending upon application (e.g., more than 4 (e.g., 6) or less than 4 (e.g., 3) wavelength ranges can be used). Filters can be selected with blocking OD>6, with rapid transitions from the pass band to blocking and precise tolerances of the pass and blocking band edges, in order to improve illumination subsystem 192 performance. In the specific example, the performance of the illumination subsystem is strongly dependent on total power delivered for each of the 4 excitation wavelengths, uniformity of illumination between the center and periphery, and achieving minimal background fluorescence. As such, variations of the example can include an increased number of LEDs used for excitation (i.e., thereby increasing power), brighter LEDs (i.e., thereby increasing power), and/or use of different dyes with higher quantum efficiency; configurations for producing increased uniformity of light illumination (e.g., by changing the angle of excitation, by use of LEDs placed in multiple location or using reflectors); and implementation of a desired surface finish and black coating in optical elements and/or support tubes used in the optical path (e.g., thereby mitigating background fluorescence).

In a specific example, the detection subsystem 196 includes: a set of lenses 197 (e.g., two 0.1 NA, apochromatic objective lenses, TL2X-SAP) which exhibit diffraction limited performance from 400-700 nm for shaping (e.g., collimation and focusing) of the light (e.g., fluorescence) emanating from the region(s) of interest of the sample processing chip 132, onto a detector 198 (e.g., 25 Megapixel camera). The detection subsystem 196 also includes a filter 96 (e.g., multiband pass filter) that allows the transmission of light emanating from dyed contents of the sample processing chip 132. The detector 198 of the specific example include CMOS components (e.g., with 5472×3648 pixels that are 2.4×2.4 microns each, with ~4 pixels available for each functionalized microparticle). The quantum efficiency of the detector 198 of the specific example is ~80% from 400 nm to 525 nm, with a decrease to ~45% at 700 nm. The detector 198 of the specific example has a dark noise level of 3.26 electrons per pixel per second at room temperature, which can be improved by positioning cooling elements in proximity to the detector 198. However, variations of the specific example can include any other configuration of detectors, optics, and/or filtering elements. For instance, variations of the detector 198 can be configured with a greater number of pixels available for imaging each of a distribution of functionalized microparticles and/or in combination with image processing, the detection subsystem 196 can be configured to resolve signals from individual microparticles with mitigation of emissions from neighboring particles.

In the specific example, the successful performance of the detection subsystem 196 is determined by one or more of: (1) sensitivity, in relation to an ability to detect fluorescence emanating from at least 1,000 fluorescent molecules attached to a silica microparticle; (2) resolution, in relation to an ability to resolve two 5-micron diameter microparticles, or down to 1 micron diameter resolution, or down to sub micron diameter resolution; and (3) minimal spectral crosstalk between the fluorophores used. In relation to performance, the specific example implements configurations for increasing sensitivity by reducing background noise, and/or by reducing dark current of the detector 198 by active cooling or increasing the number of fluorescent molecules tagged to silica particles. In relation to increasing resolution, the detector 198 can be configured to take multiple images while making small local movements (e.g., micron sized displacements) in any of the 3 axes (e.g., x, y or z axes) and also by performing advanced signal processing, in coordination with control 199 described below, to suppress contributions from neighboring particles. In relation to minimization of spectral crosstalk the detection subsystem 196 implements improved matching of the excitation/emission filters with the dye(s) used. Other embodiments to increase resolution of imaging can implement confocal imaging elements by bringing in multiple pin-hole array between the microwell chip and the lens 197 such that only light emanating from a certain plane can be focused onto the imager.

In the specific example, the imaging controller 199 functions to coordinate emitter activation and image capture. In more detail, the controller 199 includes architecture for transitioning emitters between various states of activation (e.g., in relation to power attenuation to within 1% or less of maximum power, in relation to activation for between 2 milliseconds to 20 minutes, etc.); actuation of components of the illumination subsystem 192 (e.g., emitters, optics, filters, etc.) and/or the detection subsystem 196 (e.g., camera components, optics, filters, etc.) with micrometer resolution, thereby allowing focusing of images during image acquisition; and coordination/synchronization of image capture by the detection subsystem 196 in relation to transmission of and integration of light incident on the detector 198 for desired lengths of integration (e.g., 2 milliseconds to 20 minutes)

The imaging subsystem 190 can, however, include other elements and/or configurations, as described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; and U.S. application Ser. No. 14/208,458 filed 13 Mar. 2014, which are each incorporated in their entirety by this reference.

2.1.5 Deck-Supported Element—Heating and Cooling Subsystem

As shown in FIGS. 1A-1C and 2B, the system 100 can include a heating and cooling subsystem 150, which functions to transfer heat to and/or from desired regions of the reagent cartridge 120 and/or the sample processing cartridge 130. The heating and cooling subsystem 150 can additionally or alternatively function to maintain desired temperatures within internal volumes of the system 100. In variations, the heating and cooling subsystem 150 can include one or more units of: heating elements (e.g., Peltier heating elements, resistive heating elements, other heating elements), cooling elements (e.g., Peltier cooling elements, chilled aluminum block, fluidic pathway system to circulate coolant, etc.), thermal contact or non-contact bodies for transferring heat to or from the heating and cooling elements to other objects, heat sinks, fans, temperature sensors, and thermal control circuitry (e.g., with electrical coupling to processing elements of the base 180 described in more detail below). In variations, the cooling element(s) can maintain storage volumes and/or samples between 2 and 8 degrees Celsius, further preferably at 4 degrees Celsius. Additionally or alternatively, the cooling elements can maintain one or more storage volumes/samples at any suitable temperature (e.g. below 2 degrees Celsius, above 8 degrees Celsius, etc.).

One or more portions of the heating and cooling subsystem 150 can pass into openings of the deck 110 to thermally interface with or otherwise couple with desired portions of other system elements (e.g., reagent cartridges, sample processing cartridges, tool container, etc.) supported by the deck 110, in order to provide heat transfer functions for various applications. Alternatively, the deck 110 can be composed of a thermally conductive material at desired regions for heat transfer applications, and portions of the heating and cooling subsystem 150 can be configured to contact the thermally conductive material regions of the deck 110 for heat transfer.

In variations, one or more of the thermal bodies and/or other portions of the heating and cooling subsystem 150 can be coupled to actuators that move the thermal bodies into and out of thermal communication with elements supported by the deck 110. For instance, in relation to the lid 135, the sample processing chip 132, and/or the second substrate 80 of the sample processing cartridge 130, one or more portions of the heating and cooling subsystem 150 can be coupled to actuators (e.g., in communication with base 180, in communication with deck 110, in communication with moving portions of gantry 170, etc.) that position heating and/or control elements at the lid 135, the sample processing chip 132, and/or the second substrate 80 for heating of contents of the sample processing cartridge 130 during processing. In particular, movable heating components (e.g., a heating object configured to couple with the pipette interface of the gantry described below) can be used to heat and/or compress the second substrate 80 against the sample processing chip 132 for partitioning of wells of the sample processing chip 132, as described in more detail below. Additionally or alternatively, components of the heating and cooling subsystem 150 configured to heat the reagent cartridge 120 and/or other elements can be similarly coupled to actuators. However, variations of the system 100 can omit actuators of the heating and cooling subsystem 150.

The heating and cooling subsystem 150 can further additionally or alternatively include aspects described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

2.1.6 Deck-Supported Element: Pumping Subsystem

As shown in FIGS. 1A, 2B, and 5A-5B, the system 100 can include a pumping subsystem 157 (e.g., coupled to the deck 110 and/or base 180), which functions to provide positive pressure and/or negative pressure to desired portions of the sample processing cartridge 130 described above. In more detail, the pumping subsystem 157 can function to drive fluid flow from the inlet reservoir 133 and into the sample processing chip 132 of the sample processing cartridge 130. Additionally or alternatively, the pumping subsystem 157 can function to remove fluid from the waste containment region 137 of the sample processing cartridge 130 and into an external waste receptacle. In variations, the pumping subsystem 157 can include one or more ports 58 (e.g., vacuum ports) configured to interface with the sample processing cartridge 130 through openings in the deck 110, one or more pumps (e.g., vacuum pumps, peristaltic pumps, etc.) coupled to the ports 58, one or more manifolds to provide pressure driving pathways coupled to the pump(s), one or more pressure sensors configured to detect pressure levels along pressure pathways, and/or one or more control circuit elements configured to control operation of the pumping subsystem 157 (e.g., with electrical coupling to processing elements of the base 180 described in more detail below). As such, in variations, portions of the pumping subsystem 157 not directly coupled to the sample processing cartridge 130. can be situated between the deck 110 and the base 180.

The pumping subsystem 157 can further additionally or alternatively include aspects described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

2.1.7 Deck-Supported Element: Fluid Level Detection Subsystem

As shown in FIGS. 1A, 2B, and 9, the system 100 can include a fluid level detection subsystem 159 at least partially supported by the deck 110 and configured to interface with the sample processing cartridge 130. The fluid level detection subsystem 159 functions to detect and/or measure a fluid parameter (e.g. a binary presence of fluid, a volume of fluid, a fluid flow rate, a fluid type etc.) associated with fluid at the sample processing cartridge 130 and/or other fluid processing elements of the system 100. In variations, the fluid level detection subsystem 159 can include a fluid level sensor coupled to fluid level control circuitry (e.g., with electrical coupling to processing elements of the base 180 described in more detail below).

The fluid level detection subsystem 159 can further additionally or alternatively include aspects described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

2.1.8 Deck-Supported Element: Separation Subsystem and Operation Modes

As shown in FIGS. 1A and 2B, the system 100 can include a separation subsystem 160, which functions to facilitate separation of target material from non-target material (e.g., using magnetic forces, using other forces). For example, T-cells could be separated from other cells in blood using magnetic particles containing antibodies to bind only to T-cells. Unwanted cells can also be bound using antibody particles, by using negative selection techniques. Another example of separation could involve separation of fetal cells from maternal blood. Another example could be separation could involve rare circulating tumor cells from whole blood. Another example of separation could involve separation of rare antibody secreting B-cells. In variations, the separation subsystem 160 can include embodiments, variations, and examples of components described in U.S. Application 62/866,726, titled "System and Method for Target Material Retrieval from Microwells" and filed on 26 Jun. 2019, which is herein incorporated in its entirety by this reference. The separation subsystem 160 can further additionally or alternatively include aspects described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No.

15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

2.2 System—Gantry

As shown in FIGS. 1A-1C, 2A, and 2C-2D, the system 100 can include a gantry 170 coupled to the deck 110, which functions to support and/or enable actuation of one or more tools for various interactions with elements of the deck 110, along a set of axes. In variations, the gantry 170 provides one or more rails/tracks for moving tools, such as pipettor 174 with pipette interface described below, in three dimensional space (e.g., a three dimensional volume bound by the first side of the deck). In variations, tools actuated using the gantry 170 can be moved relative to the sample processing cartridge 130, reagent cartridge 120, tool container 140, or other elements, for transfer of materials (e.g. cells, reagents, particles, etc.) across different components supported by the deck 110. Additionally or alternatively, tools supported by the gantry 170 can be used for reading of barcodes associated with various disposables supported by the deck 110 (e.g., in relation to identifying proper setup of a run, in relation to inventory management, etc.). The gantry 170 preferably enables movement of one or more tools along one or more axes (e.g., X and Y axes shown in FIG. 2A) parallel to broad surfaces of the reagent cartridge 120, sample processing cartridge 130, and tool container 140, and additionally along an axis (e.g., Z axis shown in FIG. 2A) perpendicular to the broad surfaces. The gantry 170 can additionally or alternatively enable movement along a subset of these directions or along any other suitable direction. In order to enable movement, the gantry 170 includes or is otherwise coupled to one or more motors (e.g., motors for each axis or direction of movement), one or more encoders for position identification in each axis or direction of movement, and/or one or more switches (e.g., optical switches for each axis) for control of the gantry 170 (e.g., where the switches are electrically coupled with control circuitry described in relation to the base 180 below).

As shown in FIG. 2A, the gantry 170 can include and/or or be configured to interact with a pipettor 174, which functions to hold, move, and/or otherwise interact with any number of tips or other tools, such as those of the tool container 140 described above. In variations, the pipettor 174 assembly can include one or more of: a pump (e.g., displacement pump) for providing pressure differentials for delivery and aspiration of fluids, a pressure sensor for sensing pipetting pressure, a level sensor for sensing fluid level within the pipettor 174, a tip detector (e.g., to enable determination of presence or absence of a tip coupled to the pipettor 174), and a tip ejection motor coupled to a tip ejector for removing tips from the pipettor 174. As shown in FIG. 2A, the pipettor 174 can be coupled to the Z-rail 173 of the gantry 170; however, in other variations, the pipettor 174 can additionally or alternatively be coupled to other portions of the gantry 170.

The pipettor 174 is preferably operable in an automated fashion (e.g., motorized, mechanized, self-operating, etc.) and can be configured to control any or all of the following predetermined parameters: volume (e.g. dispensing exact volumes, aspirating exact volumes), a height above the well at which each material is dispensed (e.g. priming buffer is dispensed between 0.25 and 0.3 millimeters above the top of each well, cell suspension is dispensed at a height of 0.25 millimeters above the top of each well, etc.), or can control any other suitable property according to any suitable parameter. Additionally or alternatively, the pipettor 174 can be configured to operate in a manual fashion (e.g., according to a user, with user intervention, held and used by a user, etc.) or in any suitable way. In yet another embodiment, the pipettor 174 may be used to pick up one or more tools associated with the tool container, such as any or all of: a mechanical tool, magnetic tool, an optical tool, and any other suitable tool. The tools can be moved by the pipettor 174 to the reagent cartridge and/or the microwell cartridge such that the tool(s) can perform specific mechanical/magnetic and/or optical functions with respect to specific contents of the reagent cartridge or microwell cartridge.

The gantry 170 can additionally or alternatively include aspects described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

2.3 System—Base

As shown in FIG. 1A, the system 100 can include a base 180, which functions to support control and processing architecture associated with elements of the deck 110 and gantry 170 described above. In variations, the base 180 can support control and processing architecture for one or more system functions including: pressure modification for fluid delivery throughout the sample processing cartridge 130 and/or pipettor 174; fluid level sensing (e.g., at the sample processing cartridge 130, at the pipettor 174, at various storage volumes of the reagent cartridge 120, etc.); actuation of lid opening mechanisms of the sample processing cartridge 130; thermocycling and/or other heating functions for the reagent cartridge 120 and/or sample processing cartridge 130; cooling functions for the reagent cartridge 120 and/or sample processing cartridge 130; separation functions (e.g., elution, magnetic separation, other separation, etc.); functions for control of the gantry 170; functions involving receiving sensor signals and returning outputs; functions involving receiving sensor signals and executing various actions; functions for transitioning system doors between various states (e.g., open states, closed states, locked states, unlocked states, etc.); functions associated with system power management; functions associated with system status indication elements (e.g., lights, audio output devices, visual output devices, etc.); functions associated with system input devices (e.g., buttons, keyboards, keypads, mice, joysticks, switches, touch screens, etc.); functions associated with display devices; functions associated with system data storage devices; functions associated with system transmission devices (e.g., wired transmission devices, wireless transmission devices, etc.); and other suitable functions.

In variations, the base 180 can thus support an electronics subsystem (e.g. PCB, power source, communication module, encoder, etc.) associated with a processing architecture (e.g. onboard the system, separate from the system, etc.), or any other suitable component, where the processing architecture can include any or all of: processors (e.g. microprocessors), controllers (e.g. microcontrollers), memory, storage, software, firmware, or any other suitable component. Additionally, the processing subsystem can include a machine vision module, which functions to read tags, verify protocols, perform error detection (e.g. detect that reagents do not match an assigned protocol), or perform any other function.

For instance, in an example operation flow, an operator can initiate the performance of the protocol (e.g., by pushing a button of the system, by interacting a touch-sensitive display of the system to make a selection, etc.). A barcode reader performs an error detection protocol by scanning tags of the deck elements (e.g, reagent cartridge, sample processing cartridge, tool container, etc.) and comparing with the protocol selected by the user; if the tags do not match the selected protocol, a notification can be transmitted to the user, and if the tags are correct, the protocol can begin. At this point, the operator may no longer needed. According to one or more workflows, some of which are described in Section 3 below, the correct types and volumes of materials (e.g., reagents/samples) are added to or removed from the sample processing cartridge at the correct times in an automated fashion. Once the protocol is complete, the operator can proceed with collecting and/or processing the contents of the microwell cartridge as desired, and/or setting up a new run. Variations of methods and workflows enabled by the system 100 are further described below.

Embodiments, variations, and examples of control and processing architecture are further described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

3. Method

Figure 7:
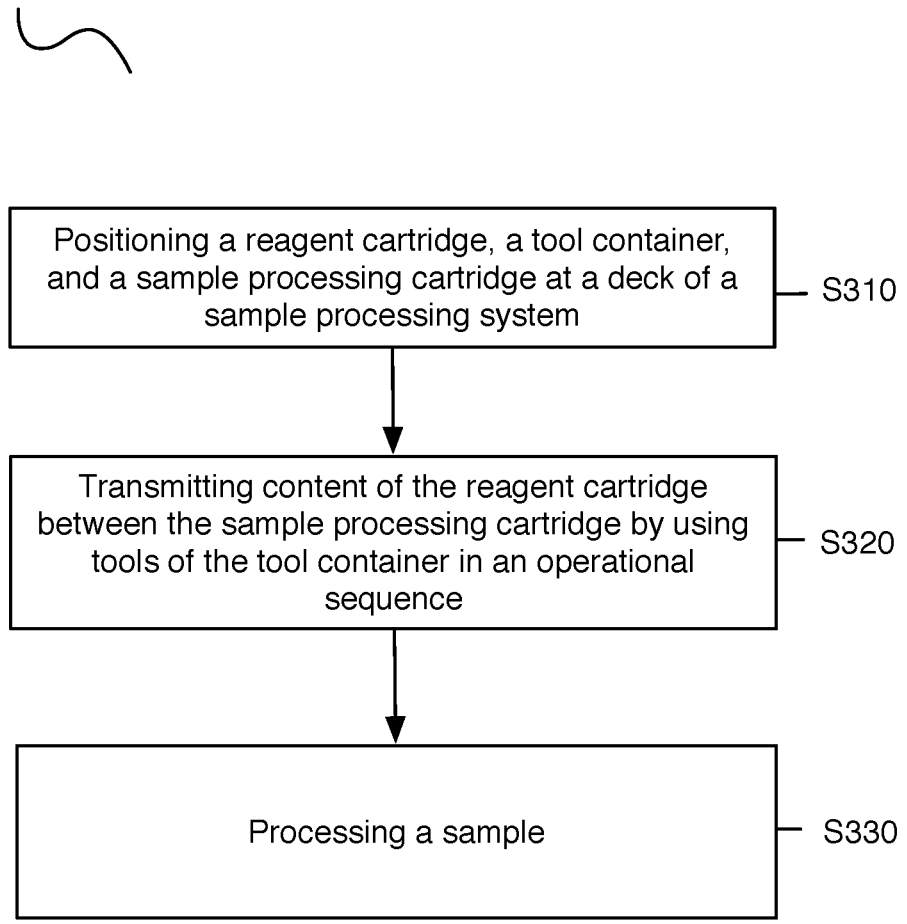
FIG. 7 depicts a flow chart of an embodiment of a method for automated single cell sample processing.

As shown in FIG. 7, an embodiment of a method 300 for sample processing includes: positioning one or more components (e.g., reagent cartridge, a tool container, and a sample processing cartridge) at a deck of a sample processing system S310; transmitting content of the reagent cartridge between the sample processing cartridge by using tools of the tool container in an operational sequence S320; processing a sample at the sample processing cartridge and/or reagent cartridge S330; and, in coordination with transmitting content and processing the sample, illuminating content derived from the sample and detecting signals emitted from content derived from the sample S340.

The method 300 functions to automate sample processing and analyses of mRNAs, proteins, and/or other biological markers, derived from cells (or other target particles) in single cell/particle format. The method 300 can include steps for automating generation of quantitative measurements (e.g., of large numbers of proteins, mRNAs, and/or other biomarkers per cell). The method 300 is preferably implemented using an embodiment, variation, or example of the system 100 described above, with integration of hardware platform subsystems, disposables, and reagents to automate sample processing from initial sample reception to generation of results. In more detail, method processing steps, in association with system aspects described above, can include optimization of fluid pumping pressures for all reagents used, such that cells or particles captured at the set of wells of the sample processing chip do not egress during fluid pumping; optimization of heating/incubation parameters for both for probe hybridizations and probe denaturation; and development of fluorescence detection parameters, such as emitter power and image acquisition timing relative to excitation. The method is further preferably at least partially automated (e.g., requires user to load reagents and select a protocol, requires no user intervention, etc.), but one or more portions can additionally or alternatively be manually performed (e.g., for quality control steps, for all protocols, for rare protocols, etc.).

In variations, examples of which are described in more detail below, the method 300 can be used for detection and quantification of cell-derived proteins (e.g., surface proteins expressed in immune cells), with development of oligonucleotide tag systems (e.g., tag-antibody complexes) for real-time detection of large numbers (e.g., hundreds, thousands) of biomarkers from a single cell captured in single-cell format within a microwell. Variations of such methods implement sequential probe hybridization and detection to rapidly enable detection on the order of hours. Additionally or alternatively, in variations, examples of which are described in more detail below, the method 300 can be used to detect multiple mRNA targets (e.g., of a panel of 100 or more mRNA targets) from multiple single cells, with quantitation of mRNA molecules (e.g., based on fluorescent detection using an embodiment of the imaging subsystem 190 described above), on the order of hours.

Additionally or alternatively, the method 300 can include any or all of the processes described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

Specific workflows associated with the method 300 and system elements described above are described in further detail below in Sections 3.2 and 3.3, where samples (e.g., samples including cell-derived material, proteins, mRNAs, proteins and mRNA; samples that include multiple samples each tagged with multiplexing barcodes; samples that include encapsulated particles from either cell or non-cell derived biomarkers, etc.) can be processed according to the workflows. Biochemical compositions enabling such workflows are described in Section 3.1.

3.1 Method—Biochemical Compositions

As described above, in relation to enablement of capture and detection of targets, the method 300 can implement compositions that tag targets and allow for sequential probe hybridizations and detections, thereby allowing detection and quantitative measurements of large numbers of biomarkers.

Figure 8:
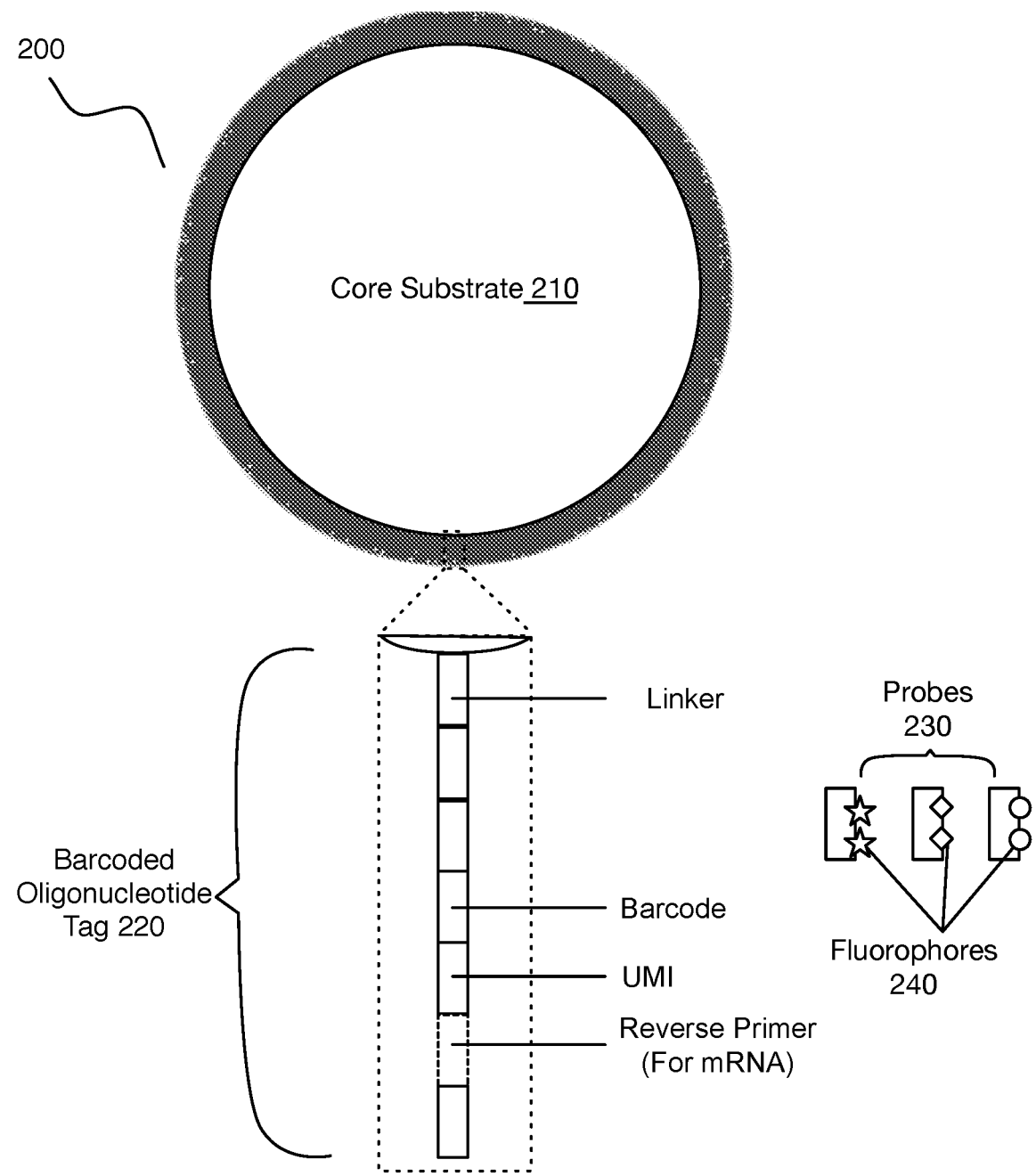
FIG. 8 depicts an embodiment of a composition used for automated single cell sample processing.

In variations, as shown in FIG. 8, the composition 200 can include a core substrate 210 (e.g., microsphere, other microparticle) composed of silica (which provides a non-fluorescing and transparent material enabling ease of fluorescence imaging) or another suitable material. In specific examples, units of the core substrate 210 can include streptavidin coated silica particles (e.g., 2 micron diameter, 5 micron diameter, etc.). The core substrate 210 is coupled to one or more units of a barcoded oligonucleotide tag 220 (e.g., with multiple barcode segments) for different targets (e.g., antibodies, mRNAs, etc.), and where the oligonucleotide tag 220 can be hybridized to multiple sets of short oligonucleotide probes 230. Each of the set of probes 230 can be coupled with a fluorophore of a set of fluorophores 240, which enables detection of different targets on the order of $F^P$, where F is the number of fluorophores, and P is the number of probes. Such a configuration can allow for serial sequential probe hybridizations and detections (e.g., for an immune panel, for another panel associated with other biomarkers). The multiplexing applications of the composition 200 can be expanded by having more barcode sections, more fluorophore-associated colors, other signal emitting sections (e.g., non-fluorescent signal emitting sections), and/or more melt point designs per fluorophore color. Tags 220 are coupled to the core substrates 210 (e.g., >$10^6$ tags per microparticle), with appropriate washing steps to remove unbound tags. Furthermore, during use, dilution of concentration of probes can be performed, in order to facilitate detection (e.g., in relation to optimizing for appropriate signal output associated with fluorophores, for detection by the imaging subsystem).

In a specific example related to antibody tagging and detection, the composition 200 can include a single stranded oligonucleotide tag 220 for each of a set of different antibodies, where each oligonucleotide tag 220 is hybridized specifically to 3 sets of short oligonucleotide (~30 bases, with other suitable numbers of bases in variations) probes 230'. Each of the probes is coupled with one of four fluorophores (e.g., fluorophores corresponding to dyes described above), which enables detection of up to 64 (i.e., 4×4×4) different antibodies using sequential hybridization and detection, according to methods described below. By configuring probes with different melt points (e.g., 2 per color, more than 2 per color, etc.), variations of the example composition 200 can be used to multiplex up to 128 (i.e., 64×2, or $F^P$*M, where F is the number of fluorophores, P is the number of probes, and M is the number of melt points) different antibodies (or other targets). In order to not confound the detection of different tags from the same microwell, sets of tags (e.g., 4-8 sets) can be specifically bound to sets of silica microspheres and distributed accordingly during use. For instance, in relation to sample processing chip described above, a set of functionalized microspheres can be stochastically distributed across the set of wells of the sample processing chip and/or the second substrate (e.g., at the base of a well of either the sample processing chip or the second substrate), thereby ensuring at least one unit of the composition 200 for each combination of antibodies is present in every well.

In another specific example related to mRNA capture, the composition 200 can include a single-stranded oligonucleotide tag 210 for each of a set of different target mRNAs where each oligonucleotide tag 210 is hybridized specifically to 3 sets of short oligonucleotide probes 230" (~15 bases, with other suitable numbers of bases in variations) followed by an mRNA gene specific reverse primer (~20 bases, with other suitable numbers of bases in variations). Each of the probes is coupled with one of four fluorophores (e.g., fluorophores corresponding to dyes described above), which enables detection of up to 64 (i.e., 4×4×4) different target mRNA using sequential hybridization and detection (e.g., to detect a first mRNA, a first tag can have a first probe with fluorophore 1, a second probe with fluorophore 1, and a third probe with fluorophore 2; to detect a second mRNA, a second tag can have a first probe with a fluorophore 1, a second probe with fluorophore 2, and third probe with fluorophore 2; to detect a third mRNA, a third tag can have a first probe with a fluorophore 2, a second probe with fluorophore 1, and a third probe with fluorophore 2; etc.)

By configuring probes with different melt points (e.g., 2 per color, more than 2 per color, e.), variations of the example composition 200" can be used to multiplex up to 128 (i.e., 64×2, or $F^P$*M, where F is the number of fluorophores, P is the number of probes, and M is the number of melt points) different mRNAs or other targets. In order to not confound the detection of different tags from the same microwell, sets of tags (e.g., 4-8 sets) can be specifically bound to sets of silica microspheres and distributed accordingly during use. For instance, in relation to sample processing chip described above, a set of functionalized microspheres can be stochastically distributed across the set of wells of the sample processing chip and/or the second substrate (e.g., at the base of a well of either the sample processing chip or the second substrate), thereby ensuring at least one unit of the composition 200 for each combination of antibodies is present in every well. For instance, to enable 100 mRNA detections, units of the composition 200 can be configured with oligonucleotide tags 210 for binding to 34 different sets of silica microparticles with unique 3 sets of tags per silica sets (i.e., 34 silica particles×3 tags/silica particle set=102 combinations). Then, during manufacturing of the sample processing chip and/or second substrate, these silica particles can be randomly embedded within wells. Alternatively, to enable 100 panel mRNA detections, units of the composition 200" can be configured as 33 silica particles containing 3 sets of mRNA primers and 1 silica particle containing only one mRNA primer.

TABLE 1 presents example numbers of combinations of specifically detectable targets possible under various configurations of compositions (e.g., in relation to numbers of barcodes, numbers of fluorophores, and numbers of melting point designs.

TABLE 1

| Number of Barcodes | Number of colors/ fluorophores | Additional Melts per color | Total Number of Combinations possible |
|---|---|---|---|
| 1 | 4 | 3 | =3*4 = 12 |
| 2 | 4 | 3 | =3*$4^2$ = 48 |
| 3 | 4 | 3 | =3*$4^3$ = 192 |
| 4 | 4 | 3 | =3*$4^4$ = 768 |
| 5 | 4 | 3 | =3*$4^5$ = 3072 |
| 6 | 4 | 3 | =3*$4^6$ = 12,288 |
| 1 | 5 | 3 | =3*5 = 15 |
| 2 | 5 | 3 | =3*$5^2$ = 75 |
| 3 | 5 | 3 | =3*$5^3$ = 375 |
| 4 | 5 | 3 | =3*$5^4$ = 1875 |
| 5 | 5 | 3 | =3*$5^5$ = 9375 |
| 6 | 5 | 3 | =3*$5^6$ = 46875 |
| ... | ... | ... | ... |
| P | F | M | =M*$F^P$ |

Additionally or alternatively, embodiments, variations, and examples of the compositions 200, 200', 200" can include aspects described in U.S. Application No. 62/945,006 filed 6 Dec. 2019, which is herein incorporated in its entirety by this reference.

3.2 Method—Example Workflow for Antibody/Protein Detection

Figure 9A:
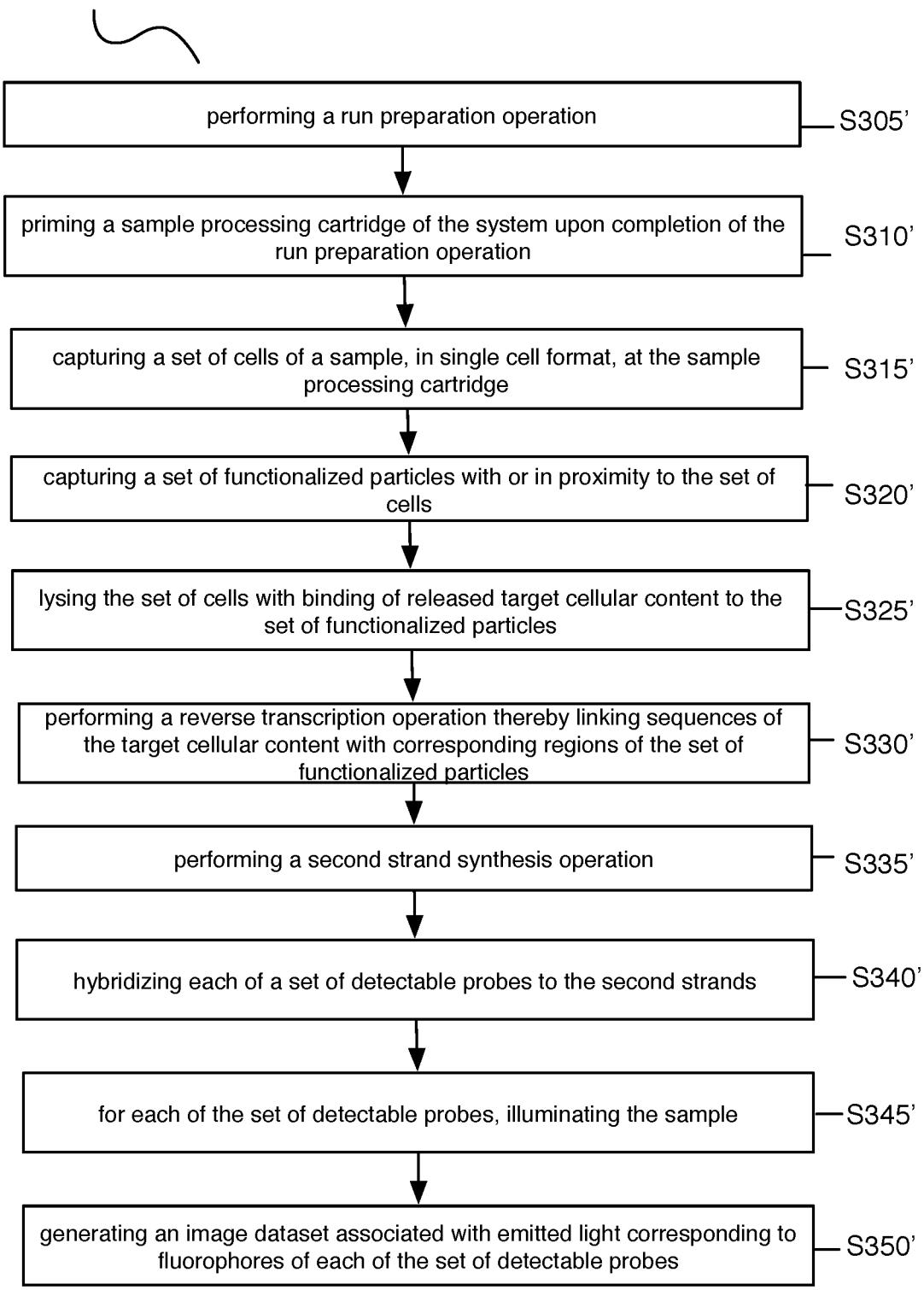
FIGS. 9A-9B depict a first variation of a method for automated single cell sample processing.
Figure 9B:
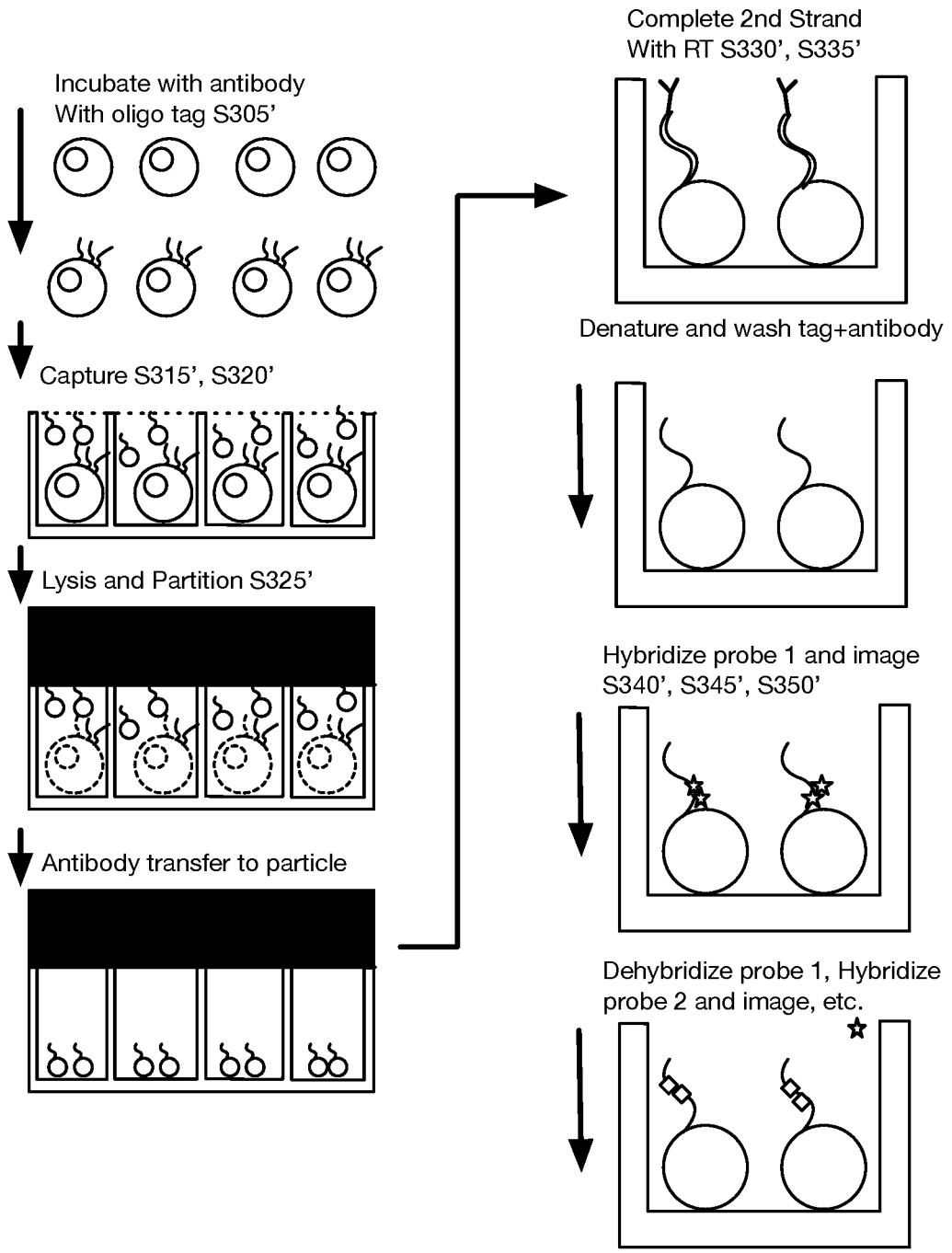

As shown in FIGS. 9A and 9B, a variation of the method configured for antibody/protein detection 300' can include: performing a run preparation operation, wherein the run preparation operation configures a system for performing an antibody/protein detection protocol S305'; priming a sample processing cartridge of the system upon completion of the run preparation operation S310'; capturing a set of cells of a sample, in single cell format, at the sample processing cartridge (e.g., with tagging of antibodies/proteins of the cells) S315'; capturing a set of functionalized particles (e.g., of the compositions 200, 200', 200" described above) with or in proximity to the set of cells, at the sample processing cartridge and/or a second substrate for the retaining the set of functionalized particles S320'; lysing the set of cells with binding of released target cellular content (e.g., tagged antibodies, other target proteins) to the set of functionalized particles S325' (e.g., with associated washing of functionalized particles of any unbound and/or non-target content, and partitioning of individual capture wells by an isolation material); performing a reverse transcription operation S330', thereby linking sequences of the target cellular content (e.g., antibodies, other target proteins) with corresponding regions (e.g., short tags) of the set of functionalized particles; performing a second strand synthesis operation S335'; hybridizing each of a set of detectable probes (e.g., of variations of compositions 200 above) to the second strands at the set of functionalized particles S340' (e.g., within wells of the sample processing cartridge and/or second substrate); for each of the set of detectable probes, illuminating the sample processing cartridge and/or second substrate S345' and generating an image dataset associated with emitted light corresponding to fluorophores of each of the set of detectable probes S350' (e.g., with de-hybridization and washing of previous detectable probes), thereby enabling detection of the antibodies/target proteins. Blocks of the method 300' are performed in coordination with control and processing elements of the system embodiments described above.

The method 300' can be used for rapid detection of a large number of antibodies or other proteins (e.g., in relation to characterizing immune responses of subjects providing the sample(s) being analyzed). In variations, the method 300' can be adapted for immune response testing (e.g., in relation to COVID-19, with detection of antibodies for severe acute respiratory syndrome coronavirus-2 (SARS-CoV-2), in relation to other antibodies, etc.). In variations, antibodies detected can include IgM antibodies, IgG antibodies, IgD antibodies, IgA antibodies, IgE antibodies, or other antibodies (e.g., non-human antibodies).

In more detail, performing a run preparation operation S305' can include sub-steps associated with one or more of: preparing a cell suspension (e.g., with incubation of the cells with oligonucleotide tags for antibody tagging); initializing and performing operational checks of system subsystems (e.g., associated with the deck, associated with the gantry, associated with the base, etc.); returning the gantry to a home position; removing one or more seals from the reagent cartridge and/or loading reagents onto the reagent cartridge; positioning a sample processing cartridge unit; removing one or more seals from the tool container positioned at the deck; dispensing the cell suspension into a storage container prior to use; verifying proper positioning and states (e.g., in relation to expiration dates) of disposables for the protocol, upon scanning tags of disposables with a camera (e.g., machine vision camera); receiving sample identification information (e.g., from an operator); and initiating run of the sample. Steps of S305" can be implemented by the system automatically and/or by an operator. Furthermore, various sub-steps can be performed once, or repeated as recommended.

In more detail, priming a sample processing cartridge of the system upon completion of the run preparation operation S310' and capturing a set of cells of a sample in single cell format, at the sample processing cartridge S315' can include one or more of: dispensing a priming solution (e.g., in a manner that prevents bubbles from being trapped within the sample processing cartridge) into the inlet reservoir of a sample processing cartridge; incubating the priming solution within the sample processing cartridge; dispensing one or more wash solutions into the inlet reservoir of the sample processing cartridge; transmitting solutions to a waste containment region of the sample processing cartridge; dispensing a cell suspension into the inlet reservoir of the sample processing cartridge and capturing cells, in single-cell format, within wells of the sample processing cartridge; tagging antibodies of the captured cells (e.g., with antibody tagging materials); and performing other suitable steps associated with priming and cell capture. Pumping pressures are optimized for all reagents used in the protocol such that cells or particles captured in wells do not egress during fluid pumping. Steps S310' and S315' are preferably performed automatically by the system but can alternatively be performed in another suitable manner. Furthermore, various sub-steps can be performed once, or repeated as recommended.

In more detail, capturing a set of functionalized particles (e.g., of the compositions 200, 200', 200" described above) with the set of cells, at the sample processing cartridge and/or a second substrate for the retaining the set of functionalized particles S320' can include one or more of: dispensing a set of functionalized particles into the inlet reservoir of the sample processing cartridge and co-capturing the set of functionalized particles with the set of cells; incubating content of the wells of the sample processing cartridge; and picking up/releasing various tools (e.g., by a gantry coupled to a pipette interface) involved with the substep(s); positioning a second substrate, with the set of functionalized particles into alignment with wells of the sample processing cartridge containing cells in single-cell format (e.g., through a lid and/or an access region of the sample processing cartridge); retaining the set of functionalized particles in position (e.g., with a hydrogel or other material, etc.); and performing other suitable steps in relation to capture and positioning of functionalized particles. Pumping pressures are optimized for all reagents used in the protocol such that cells or particles captured in wells do not egress during fluid pumping. Step S320' is preferably performed automatically by the system but can alternatively be performed in another suitable manner. Furthermore, various sub-steps can be performed once, or repeated as recommended.

In more detail, lysing the set of cells with binding of released target cellular content (e.g., antibodies, other target proteins) to the set of functionalized particles S325' (e.g., with associated washing of functionalized particles of any unbound and/or non-target content, and partitioning of individual capture wells by an isolation material) can include one or more of: dispensing one or more wash solutions into the inlet reservoir of the sample processing cartridge; transmitting solutions to a waste containment region of the sample processing cartridge; dispensing a particle-binding buffer into the inlet reservoir of the sample processing cartridge; dispensing a lysis solution (e.g., at room temperature, at below room temperature, at above room temperature) into the inlet reservoir of the sample processing cartridge (e.g., for less than 1 minute, for one minute, for more than one minute, etc.); performing incubation with the lysis buffer (e.g., at room temperature, at below room temperature, at above room temperature); displacing fluid above wells of the sample processing cartridge with an oil, thereby isolating contents of wells and preventing undesired material transfer across wells (e.g., as in U.S. application Ser. No. 16/564,375 filed 9 Sep. 2019, which is herein incorporated in its entirety by this reference); displacing the oil with air from the inlet reservoir; dispensing a particle-binding wash buffer into the inlet reservoir of the sample processing cartridge; compressing the second substrate against wells of the sample processing chip, thereby partitioning wells of the set of wells containing captured cells; and performing other suitable steps associated with cell lysis. Pumping pressures are optimized for all reagents used in the protocol such that cells or particles captured in wells do not egress during fluid pumping. Step S325' is preferably performed automatically by the system but can alternatively be performed in another suitable manner. Furthermore, various sub-steps can be performed once, or repeated as recommended.

In more detail, performing a reverse transcription operation with lysate of the set of cells S330', thereby linking sequences of the target cellular content (e.g., antibodies, other target proteins) with corresponding regions (e.g., short tags) of the set of functionalized particles, can include one or more of: dispensing one or more wash solutions into the inlet reservoir of the sample processing cartridge (e.g., thereby washing away undesired lysate); transmitting solutions to a waste containment region of the sample processing cartridge; dispensing a particle-binding buffer into the inlet reservoir of the sample processing cartridge; dispensing a DTT solution into the inlet reservoir of the sample processing cartridge; dispensing a lysis solution into the inlet reservoir of the sample processing cartridge; displacing fluid above wells of the sample processing cartridge with an oil, thereby isolating contents of wells and preventing undesired material transfer across wells (e.g., as in U.S. application Ser. No. 16/564,375 filed 9 Sep. 2019, which is herein incorporated in its entirety by this reference); displacing the oil with air from the inlet reservoir; dispensing a particle-binding wash buffer into the inlet reservoir of the sample processing cartridge; dispensing a pre-RT reaction wash buffer into the inlet reservoir of the sample processing cartridge; dispensing an RT cocktail into the inlet reservoir of the sample processing cartridge; incubating contents of the sample processing cartridge; performing incubation steps; displacing a second substrate toward and/or away from the sample processing chip, thereby partitioning contents and/or allowing fluid flow across capture wells; and picking up/releasing various tools involved with the substep(s). Pumping pressures are optimized for all reagents used in the protocol such that cells or particles captured in wells do not egress during fluid pumping. Step S330' is preferably performed automatically by the system but can alternatively be performed in another suitable manner. Furthermore, various sub-steps can be performed once, or repeated as recommended.

In more detail, performing a second strand synthesis operation S335' with performance of one or more wash steps to remove content (e.g., undesired material, lysate, etc.) can include one or more of: mixing target captured content with a hydroxide solution (e.g., sodium hydroxide solution) within a container (e.g., of the reagent cartridge, of the sample processing cartridge); separating functionalized magnetic particles from other content (e.g., by way of the magnetic separation subsystem described); discarding waste material; washing target content; mixing a second strand synthesis primer enzyme with washed target content; thermocycling target content with separation and washing steps (e.g., by way of subsystems described above); and picking up/releasing various tools involved with the substep(s). Step S335' is preferably performed automatically by the system but can alternatively be performed in another suitable manner. Furthermore, various sub-steps can be performed once, or repeated as recommended.

In more detail, hybridizing each of a set of detectable probes (e.g., of variations of compositions 200, 200', and 200" above) to the second strands at the set of functionalized particles S340' (e.g., within wells of the sample processing cartridge and/or second substrate) can include one or more of: transmitting solutions of the oligonucleotide probes, with fluorescently detectable portions (e.g., as described in relation to composition above) to the sample processing cartridge (e.g., within wells of the microwell chip), second substrate, and/or reagent cartridge, for hybridization with corresponding regions of material at the set of functionalized particles; performing one or more incubation steps (e.g., with suitable heating profiles in terms of temperatures, ramps, and cycles); performing one or more wash steps; and picking up/releasing various tools involved with the substep(s). Step S340' is preferably performed automatically by the system but can alternatively be performed in another suitable manner. Furthermore, various sub-steps can be performed once, or repeated as recommended.

In more detail, for each of the set of detectable probes, illuminating the sample processing cartridge and/or second substrate S345' can include transmitting light, with suitable power settings, through optics components toward captured sample (e.g., containing target components hybridized to probes); performing one or more focusing operations in relation to light transmission (e.g., with actuation of the light emitting and/or sample supporting components into position); coordinating timing of illumination with image capture with performed in Block S350'; performing operations as described in U.S. application Ser. No. 14/208,458 filed 13 Mar. 2014 as incorporated by reference above; and performing any other suitable illumination steps. Step S345' is preferably performed automatically by the system (e.g., imaging subsystem/illumination subsystem described above), but can alternatively be performed in another suitable manner. Furthermore, various sub-steps can be performed once, or repeated as recommended.

In more detail, generating an image dataset associated with emitted light corresponding to fluorophores of each of the set of detectable probes S350' can include one or more of: transmitting light through optics components from captured sample (e.g., containing target components hybridized to probes) toward a detection subsystem; performing one or more focusing operations in relation to light transmission (e.g., with actuation of the light detecting and/or sample supporting components into position); performing one or more focusing operations in relation to fiducials of sample containing containers; stitching multiple images together in order to create assembled images of capture substrates (e.g., sample processing chip and/or second substrate described above); coordinating timing of image capture with illumination performed in Block S345'; performing operations as described in U.S. application Ser. No. 14/208,458 filed 13 Mar. 2014 as incorporated by reference above; and performing any other suitable detections steps. Step S350' is preferably performed automatically by the system (e.g., imaging subsystem/illumination subsystem described above), but can alternatively be performed in another suitable manner. Furthermore, various sub-steps can be performed once, or repeated as recommended.

In relation to hybridization and detection of multiple sets of probes (e.g., sets of fluorescent probes corresponding to various fluorophores described above), steps S340', S345', and S350' can include steps for de-hybridization (e.g., with heat, by chemical reaction, by photocleaving, etc.) and washing of de-hybridized probes, thereby enabling detection of the antibodies/target proteins in a desired sequence. As such, a first set of barcoded and fluorescent probes can be hybridized onto targets captured at the set of functionalized particles, and then imaged with detection of a first fluorescent profile. Then, the first set of barcoded and fluorescent probes can be de-hybridized. These processes can then be repeated for each of the set of probes, with image analysis performed based on pre-set thresholds to create a map of cells to antibody (or other protein) profiles. Such operations can thus allow for accurate detection of target antibodies/proteins, with minimization of signal crosstalk (e.g., in relation to scenarios were multiple types of probes are hybridized to target components simultaneously).

Embodiments, variations, and examples of the method 300' can additionally or alternatively include steps described in U.S. application Ser. No. 16/867,235, filed 5 May 2020; U.S. application Ser. No. 16/867,256, filed 5 May 2020, as incorporated by reference above.

3.3 Method—Example Workflow for mRNA detection and Quantitation

Figure 10A:
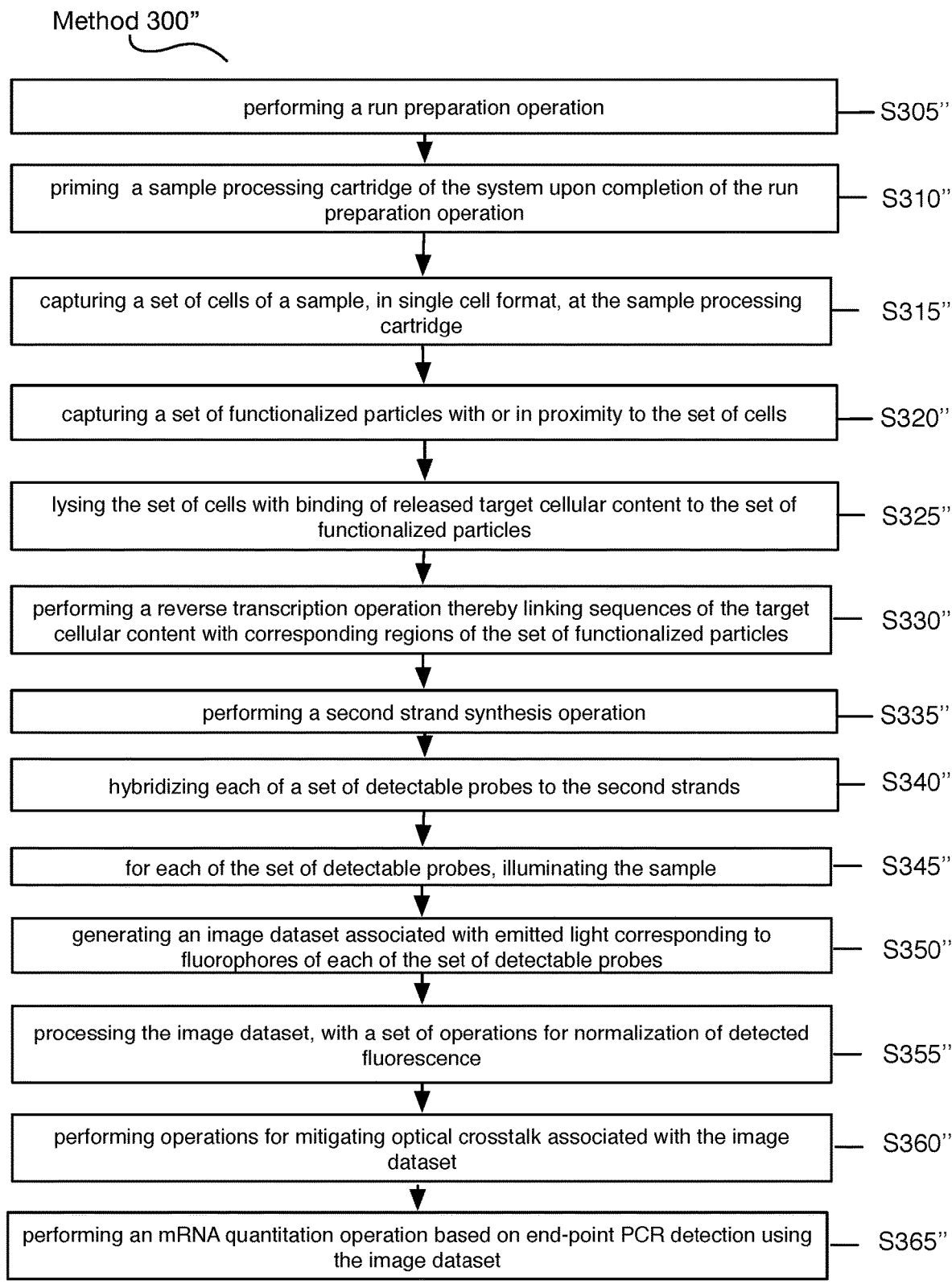
FIGS. 10A-10B depict a second variation of a method for automated single cell sample processing.
Figure 10B:
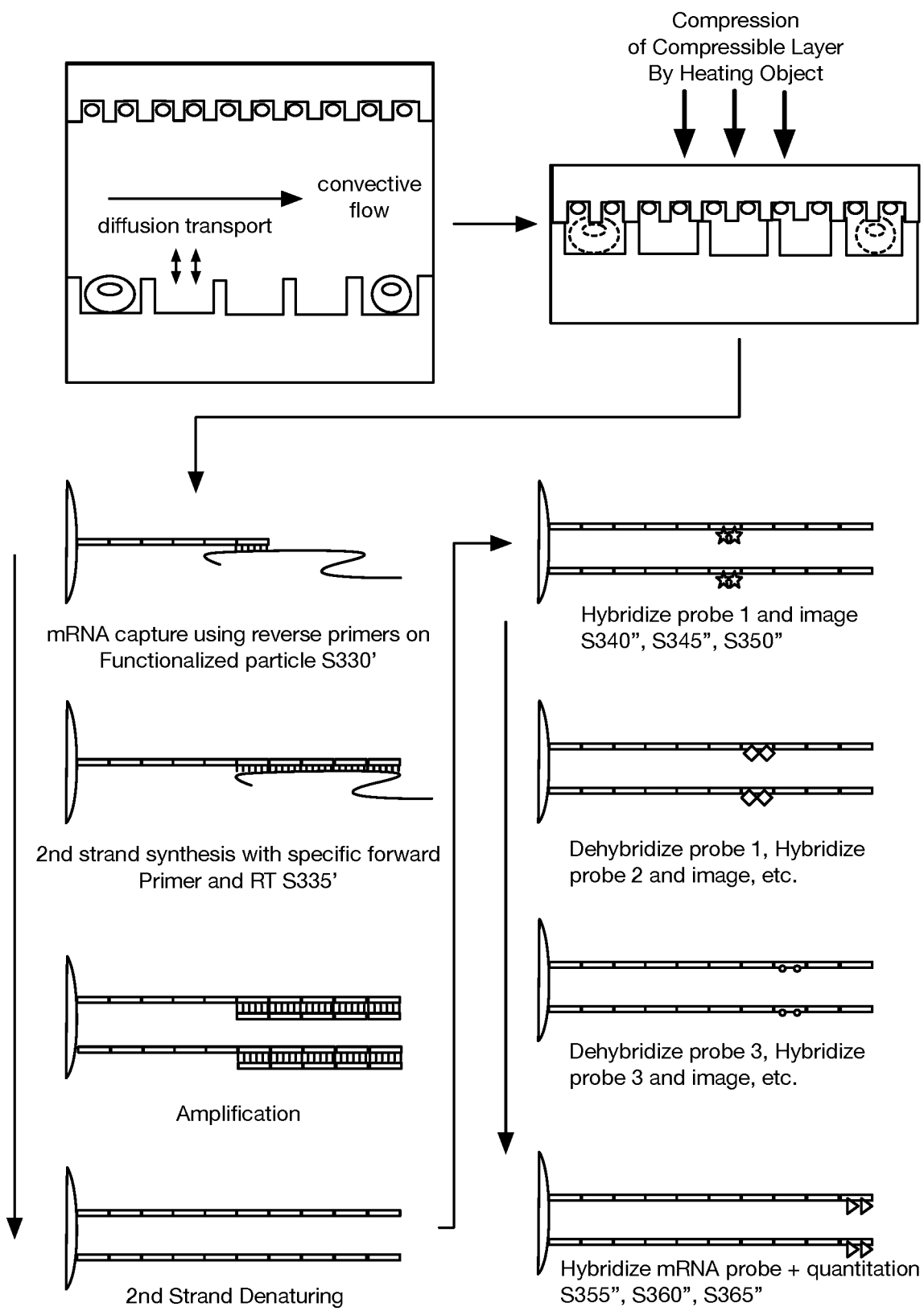

As shown in FIGS. 10A and 10B, a variation of the method configured for mRNA detection 300" can include: performing a run preparation operation, wherein the run preparation operation configures a system for performing an mRNA detection protocol S305"; priming a sample processing cartridge of the system upon completion of the run preparation operation S310"; capturing a set of cells of a sample, in single cell format, at the sample processing cartridge S315"; capturing a set of functionalized particles (e.g., of the compositions 200 described above) with the set of cells, at the sample processing cartridge and/or a second substrate for the retaining the set of functionalized particles S320"; lysing the set of cells with binding of released target cellular content (e.g., mRNAs) to the set of functionalized particles S325" (e.g., with associated washing of functionalized particles of any unbound and/or non-target content, and partitioning of individual capture wells by an isolation material); performing a reverse transcription operation S330", thereby linking sequences of the target content (e.g., mRNAs) with corresponding regions (e.g., short tags) of the set of functionalized particles; performing a second strand synthesis operation S335"; hybridizing each of a set of detectable probes (e.g., of variations of compositions 200, 200', and 200" above) to the second strands at the set of functionalized particles S340" (e.g., within wells of the sample processing cartridge and/or second substrate); for each of the set of detectable probes, illuminating the sample processing cartridge and/or second substrate S345" and generating an image dataset associated with emitted light corresponding to fluorophores of each of the set of detectable probes S350" (e.g., with de-hybridization and washing of previous detectable probes), thereby enabling detection of the mRNAs. Variations of the method 300" can further include steps for processing the image dataset, with a set of operations for normalization of detected fluorescence S355"; performing operations for mitigating optical crosstalk associated with the image dataset S360"; and performing an mRNA quantitation operation based on end-point PCR detection using the image dataset S365".

The method 300" can function to rapidly (e.g., within hours) detect hundreds of transcripts on every single cell to be performed within 3 hours in an automated manner. For instance, implementation of the method 300", using an embodiment of the system described above, can provide an end-to-end solution for single cell analyses, whether the analyses are in discovery, translational, or clinical phases. Extensions of the method 300" can be used for spatial transcriptomics, with analyses of mRNAs of biological material (e.g., cells, tissues), distributed in space (e.g., across a set of microwells, within a tissue, within a 2D structure, within a 3D structure, etc.).

In more detail, performing a run preparation operation S305" can include sub-steps associated with one or more of: preparing a cell suspension; initializing and performing operational checks of system subsystems (e.g., associated with the deck, associated with the gantry, associated with the base, etc.); returning the gantry to a home position; removing one or more seals from the reagent cartridge and/or loading reagents onto the reagent cartridge; positioning a sample processing cartridge unit; removing one or more seals from the tool container positioned at the deck; dispensing the cell suspension into a storage container prior to use; verifying proper positioning and states (e.g., in relation to expiration dates) of disposables for the protocol, upon scanning tags of disposables with a camera (e.g., machine vision camera); receiving sample identification information (e.g., from an operator); and initiating run of the sample. Steps of S305" can be implemented by the system automatically and/or by an operator. Furthermore, various sub-steps can be performed once, or repeated as recommended.

In more detail, priming a sample processing cartridge of the system upon completion of the run preparation operation S310" and capturing a set of cells of a sample in single cell format, at the sample processing cartridge S315" can include one or more of: dispensing a priming solution (e.g., in a manner that prevents bubbles from being trapped within the sample processing cartridge) into the inlet reservoir of a sample processing cartridge; incubating the priming solution within the sample processing cartridge; dispensing one or more wash solutions into the inlet reservoir of the sample processing cartridge; transmitting solutions to a waste containment region of the sample processing cartridge; dispensing a cell suspension into the inlet reservoir of the sample processing cartridge and capturing cells, in single-cell format, within wells of the sample processing cartridge; tagging antibodies of the captured cells (e.g., with antibody tagging materials); and performing other suitable steps associated with priming and cell capture. Pumping pressures are optimized for all reagents used in the protocol such that cells or particles captured in wells do not egress during fluid pumping. Steps S310" and S315" are preferably performed automatically by the system but can alternatively be performed in another suitable manner. Furthermore, various sub-steps can be performed once, or repeated as recommended.

In more detail, capturing a set of functionalized particles (e.g., of the compositions 200 described above) with the set of cells, at the sample processing cartridge and/or a second substrate for the retaining the set of functionalized particles S320" can include one or more of: dispensing a set of functionalized particles into the inlet reservoir of the sample processing cartridge and co-capturing the set of functionalized particles with the set of cells; incubating content of the wells of the sample processing cartridge; and picking up/releasing various tools (e.g., by a gantry coupled to a pipette interface) involved with the substep(s); positioning a second substrate, with the set of functionalized particles into alignment with wells of the sample processing cartridge containing cells in single-cell format (e.g., through a lid and/or an access region of the sample processing cartridge); retaining the set of functionalized particles in position (e.g., with a hydrogel or other material, etc.); and performing other suitable steps in relation to capture and positioning of functionalized particles. Pumping pressures are optimized for all reagents used in the protocol such that cells or particles captured in wells do not egress during fluid pumping. Step S320" is preferably performed automatically by the system but can alternatively be performed in another suitable manner. Furthermore, various sub-steps can be performed once, or repeated as recommended.

In more detail, lysing the set of cells with binding of released target cellular content (e.g., mRNAs) to the set of functionalized particles S325" (e.g., with associated washing of functionalized particles of any unbound and/or non-target content, and partitioning of individual capture wells by an isolation material) can include one or more of: dispensing one or more wash solutions into the inlet reservoir of the sample processing cartridge; transmitting solutions to a waste containment region of the sample processing cartridge; dispensing a particle-binding buffer into the inlet reservoir of the sample processing cartridge; dispensing a lysis solution (e.g., at room temperature, at below room temperature, at above room temperature) into the inlet reservoir of the sample processing cartridge (e.g., for less than 1 minute, for one minute, for more than one minute, etc.); performing incubation with the lysis buffer (e.g., at room temperature, at below room temperature, at above room temperature); displacing fluid above wells of the sample processing cartridge with an oil, thereby isolating contents of wells and preventing undesired material transfer across wells (e.g., as in U.S. application Ser. No. 16/564,375 filed 9 Sep. 2019, which is herein incorporated in its entirety by this reference); displacing the oil with air from the inlet reservoir; dispensing a particle-binding wash buffer into the inlet reservoir of the sample processing cartridge; compressing the second substrate against wells of the sample processing chip, thereby partitioning wells of the set of wells containing captured cells; and performing other suitable steps associated with cell lysis. Pumping pressures are optimized for all reagents used in the protocol such that cells or particles captured in wells do not egress during fluid pumping. Step S325" is preferably performed automatically by the system but can alternatively be performed in another suitable manner. Furthermore, various sub-steps can be performed once, or repeated as recommended.

In more detail, performing a reverse transcription operation with lysate of the set of cells S330", thereby linking sequences of the target cellular content (e.g., mRNAs) with corresponding regions (e.g., gene-specific or mRNA-specific reverse primers) of the set of functionalized particles, can include one or more of: dispensing one or more wash solutions into the inlet reservoir of the sample processing cartridge (e.g., thereby washing away undesired lysate), where washing can involve displacing the second substrate away from the sample processing chip and allowing wash buffer to flow between the wells of the sample processing chip and the second substrate; transmitting solutions to a waste containment region of the sample processing cartridge; dispensing a particle-binding buffer into the inlet reservoir of the sample processing cartridge; dispensing a DTT solution into the inlet reservoir of the sample processing cartridge; dispensing a lysis solution into the inlet reservoir of the sample processing cartridge; displacing fluid above wells of the sample processing cartridge with an oil, thereby isolating contents of wells and preventing undesired material transfer across wells (e.g., as in U.S. application Ser. No. 16/564,375 filed 9 Sep. 2019, which is herein incorporated in its entirety by this reference); displacing the oil with air from the inlet reservoir; dispensing a particle-binding wash buffer into the inlet reservoir of the sample processing cartridge; dispensing a pre-RT reaction wash buffer into the inlet reservoir of the sample processing cartridge; dispensing an RT cocktail into the inlet reservoir of the sample processing cartridge; dispensing forward primers; dispensing nucleotides; incubating contents of the sample processing cartridge; performing incubation steps; displacing a second substrate toward and/or away from the sample processing chip, thereby partitioning contents and/or allowing fluid flow across capture wells; and picking up/releasing various tools involved with the substep(s). Pumping pressures are optimized for all reagents used in the protocol such that cells or particles captured in wells do not egress during fluid pumping. Step S330' is preferably performed automatically by the system but can alternatively be performed in another suitable manner. Furthermore, various sub-steps can be performed once, or repeated as recommended.

In more detail, performing a second strand synthesis operation S335" with performance of one or more wash steps to remove content (e.g., undesired material, lysate, etc.) can include one or more of: mixing target captured content with a hydroxide solution (e.g., sodium hydroxide solution) within the microwell cartridge; discarding waste material; washing target content; mixing a second strand synthesis primer enzyme with washed target content; thermocycling target content with separation and washing steps (e.g., by way of subsystems described above); and picking up/releasing various tools involved with the substep(s). Step S335" is preferably performed automatically by the system but can alternatively be performed in another suitable manner. Furthermore, various sub-steps can be performed once, or repeated as recommended.

Prior to hybridization and analysis in subsequent steps, Block S335" can further include performance of PCR operation steps with double stranded results of Block S335", including one or more of: delivery of one or more solutions (e.g., containing polymerase, forward primers, nucleotides, etc.) to wells containing the double stranded results of Block S335"; performing one or more PCR cycles, such that multiple copies of mRNA templates are created on the same silica microsphere that had the original mRNA captured; denaturing the DNA; and washing away denatured DNA, thereby leaving only single stranded target oligonucleotides at the set of functionalized particles.

In more detail, hybridizing each of a set of detectable probes (e.g., of variations of compositions 200 above) to the second strands at the set of functionalized particles S340" (e.g., within wells of the sample processing cartridge and/or second substrate) can include one or more of: transmitting solutions of the oligonucleotide probes, with fluorescently detectable portions (e.g., as described in relation to composition above) to the sample processing cartridge (e.g., within wells of the microwell chip), second substrate, and/or reagent cartridge, for hybridization with corresponding regions of material at the set of functionalized particles; performing one or more incubation steps (e.g., with suitable heating profiles in terms of temperatures, ramps, and cycles); performing one or more wash steps; and picking up/releasing various tools involved with the substep(s). Block S340" can additionally or alternatively include hybridization of gene specific probes onto the captured target oligonucleotides, in order to facilitate estimation of the number of template products for each mRNA for each functionalized particle, as further described in relation to mRNA quantitation steps below. Step S340" is preferably performed automatically by the system but can alternatively be performed in another suitable manner. Furthermore, various sub-steps can be performed once, or repeated as recommended.

In more detail, for each of the set of detectable probes, illuminating the sample processing cartridge and/or second substrate S345" can include transmitting light, with suitable power settings, through optics components toward captured sample (e.g., containing target components hybridized to probes); performing one or more focusing operations in relation to light transmission (e.g., with actuation of the light emitting and/or sample supporting components into position); coordinating timing of illumination with image capture with performed in Block S350"; performing operations as described in U.S. application Ser. No. 14/208,458 filed 13 Mar. 2014 as incorporated by reference above; and performing any other suitable illumination steps. Step S345" is preferably performed automatically by the system (e.g., imaging subsystem/illumination subsystem described above), but can alternatively be performed in another suitable manner. Furthermore, various sub-steps can be performed once, or repeated as recommended.

In more detail, generating an image dataset associated with emitted light corresponding to fluorophores of each of the set of detectable probes S350" can include one or more of: transmitting light through optics components from captured sample (e.g., containing target components hybridized to probes) toward a detection subsystem; performing one or more focusing operations in relation to light transmission (e.g., with actuation of the light detecting and/or sample supporting components into position); performing one or more focusing operations in relation to fiducials of sample containing containers; stitching multiple images together in order to create assembled images of capture substrates (e.g., sample processing chip and/or second substrate described above); coordinating timing of image capture with illumination performed in Block S345"; performing operations as described in U.S. application Ser. No. 14/208,458 filed 13 Mar. 2014 as incorporated by reference above; and performing any other suitable detections steps. Step S350' is preferably performed automatically by the system (e.g., imaging subsystem/illumination subsystem described above), but can alternatively be performed in another suitable manner. Furthermore, various sub-steps can be performed once, or repeated as recommended.

In relation to hybridization and detection of multiple sets of probes (e.g., sets of fluorescent probes corresponding to various fluorophores described above), steps S340", S345", and S350" can include steps for de-hybridization (e.g., with heat, by chemical reaction, by photocleaving, etc.) and washing of de-hybridized probes, thereby enabling detection of the antibodies/target proteins in a desired sequence. As such, a first set of barcoded and fluorescent probes can be hybridized onto targets captured at the set of functionalized particles, and then imaged with detection of a first fluorescent profile. Then, the first set of barcoded and fluorescent probes can be de-hybridized. These processes can then be repeated for each of the set of probes, with image analysis performed based on pre-set thresholds to create a map of cells to antibody (or other protein) profiles. Such operations can thus allow for accurate detection of target antibodies/proteins, with minimization of signal crosstalk (e.g., in relation to scenarios were multiple types of probes are hybridized to target components simultaneously).

As described above, the method 300" can include one or more of: processing the image dataset, with a set of operations for normalization of detected fluorescence S355"; performing operations for mitigating optical crosstalk associated with the image dataset S360"; and performing an mRNA quantitation operation based on end-point PCR detection using the image dataset S365".

In more detail, processing the image dataset, with a set of operations for normalization of detected fluorescence S355", can function normalize detection of targets (e.g., mRNA content, etc.) distributed spatially (e.g., across a microwell array). For instance, the absolute fluorescence emitted by the mRNA probes associated with one functionalized particle at a first location in space may be different from the absolute fluorescence emitted by the mRNA probes associated with another functionalized particle at a second location in space, even though they may have the same number of mRNA probes captured. As such, in variations, Block S355" can include implementing an average color specific fluorescence associated with the barcode probe for each functionalized particle, to normalize the fluorescence value of the respective mRNA probe. Since all the functionalized particles used in a run can be selected to be within the same fabrication lot, it can be assumed that each functionalized particle will have a similar number of oligonucleotide tags. Since all functionalized particles will be treated as having the same concentration of probe molecules during barcode decoding, it can also be assumed that each functionalized particle will attach a similar number of barcode tags. In the event a functionalized particle does not have a particular color in its barcode section, Block S355" can implement the value from a neighboring functionalized particle for normalization. Normalization can, however, be implemented in another suitable manner.

In more detail, performing operations for mitigating optical crosstalk associated with the image dataset S360" can include one or more of: implementing physical barriers between individual capture regions (e.g., wells) of various substrates (e.g., sample processing chips, other substrates) being imaged; performing image processing with filtering operations; controlling timing of imaging and illumination operations; and performing other suitable crosstalk mitigating operations.

In more detail, performing an mRNA quantitation operation based on end-point PCR detection using the image dataset S365" can function to take advantage of a relatively "pure" sample processing configuration where only template mRNA molecules are present at the functionalized particles prior to amplification steps. In particular, in relation to processing steps described above, most PCR inhibitors (e.g., cell lysates proteins, lipids, etc.) are washed away in multiple steps and ultimately, any amplified templates will be concentrated at a respective functionalized particle. This concentration effect thus allows detection of the presence of PCR products even when there are only a relatively small number (e.g., ~1000, less than 1000, more than 1000, etc.)

template molecules on the bead. Thus, in relation to Block S365", assuming a PCR efficiency (e.g., a PCR efficiency of 90%) can guide a threshold number of PCR cycles required to produce desired amplification of template molecules for quantitation (e.g., 11 cycles for 1000-fold amplification). Thus, a quantitative model can be used to estimate initial concentrations of template mRNA (or other targets) from an end-point (or other point associated with a PCR cycle) fluorescence value derived from captured image data. The quantitative model can be applied to target material (e.g., mRNAs) of all cells captured at a captured substrate, with single cell resolution.

Embodiments, variations, and examples of the method 300" can, however, additionally or alternatively include steps described in U.S. application Ser. No. 16/867,235, filed 5 May 2020; U.S. application Ser. No. 16/867,256, filed 5 May 2020, as incorporated by reference above.

3.4 Method—Extensions

In variations, the methods described and/or associated system components can be adapted for other applications.

Figure 11:
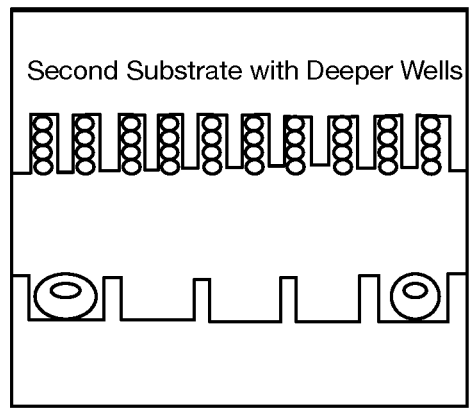
FIG. 11 depicts a first extension of a portion of a system and/or method for automated single cell sample processing.

For instance, in a first extension of the method 300", the number of transcriptomes detected per cell can be increased (e.g., from ~100 to over 500), by allowing stacking of functionalized particles within capture wells. In variations, the set of wells can be configured to be deeper, as shown in FIG. 11, such that multiple functionalized particles can be stacked within each well. Furthermore, to increase the number of unique barcodes, the number of oligonucleotide tags for detections can be increased from (e.g., from 3 to more than 3), thereby increasing the total number of multiplexed combinations as described above. To detect and resolve fluorescence from stacked functionalized particles, embodiments of the imaging system described above can be modified to perform confocal detection or other detection methods configured for imaging different planes of a sample.

Figure 12:
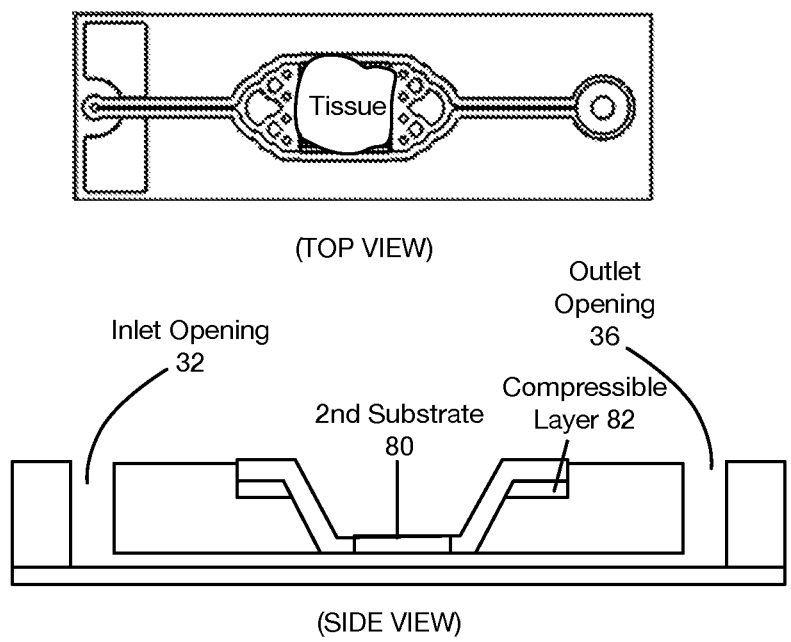
FIG. 12 depicts a second extension of a portion of a system and/or method for automated single cell sample processing.

In another extension, the methods can be adapted for spatial transcriptomic analysis of a tissue or other structure. In an example, as shown in FIG. 12, a fluidic manifold containing a second substrate can be positioned into alignment with a slide containing a mounted tissue slide (e.g., instead of the embodiment of the sample processing chip described above). This configuration can thus perform immunophenotyping of the tissue slide followed by transfer of lysed mRNA to functionalized particles in a manner analogous to that described above. Then, mRNA captured at functionalized particles can be amplified by PCR, followed by multiplexed detection and quantitation. As such, in relation to embodiments of method steps described above, a method can include one or more of: capturing a tissue sample in proximity to a set of functionalized particles, in single array format, at a set of microwells of a sample processing substrate; performing lysis of the tissue sample, at the sample processing substrate, thereby allowing binding of released biomarkers from the tissue section to the set of functionalized particles; performing a reverse transcription operation, at the set of microwells of the sample processing substrate, with content bound to the set of functionalized particles; with products of the reverse transcription operation, performing a second strand synthesis operation with content bound to the set of functionalized particles; with products of the second strand synthesis operation, performing an amplification operation at the set of functionalized particles; hybridizing each of a set of probes, corresponding to a set of fluorophores, to products of the amplification operation; and generating an image dataset of light emitted by the set of probes, thereby enabling detection of the set of targets of the sample.

In another extension, the method(s) can be adapted for phenotyping of single cells followed by single cell transcriptomic library preparation for next generation sequencing (e.g., as described in U.S. application Ser. No. 16/867,235, filed 5 May 2020; U.S. application Ser. No. 16/867,256, filed 5 May 2020, as incorporated by reference above). By multiplexed barcode detection of the oligonucleotide particles, the method can be extended with processes for linking the phenotypic information to the transcriptome information generated during sequencing.

Figure 13:
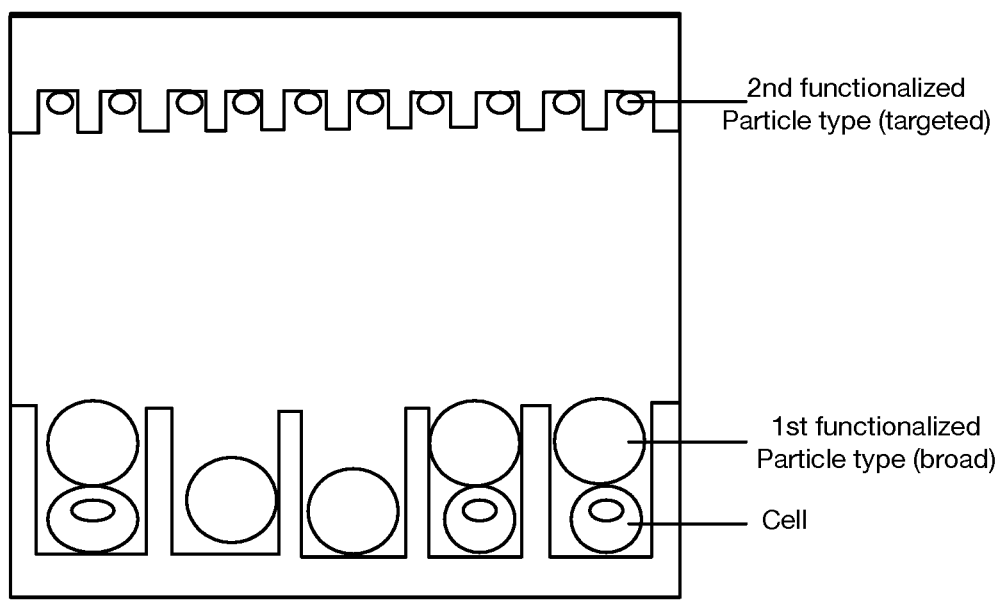
FIG. 13 depicts a third extension of a portion of a system and/or method for automated single cell sample processing.

In another extension, the method(s) can be adapted for sequential processing of single cells to capture broad unspecific biomarkers at a first functionalized particle type, followed by targeted capture and detection at second particle type (e.g., as shown in FIG. 13).

Figure 14:
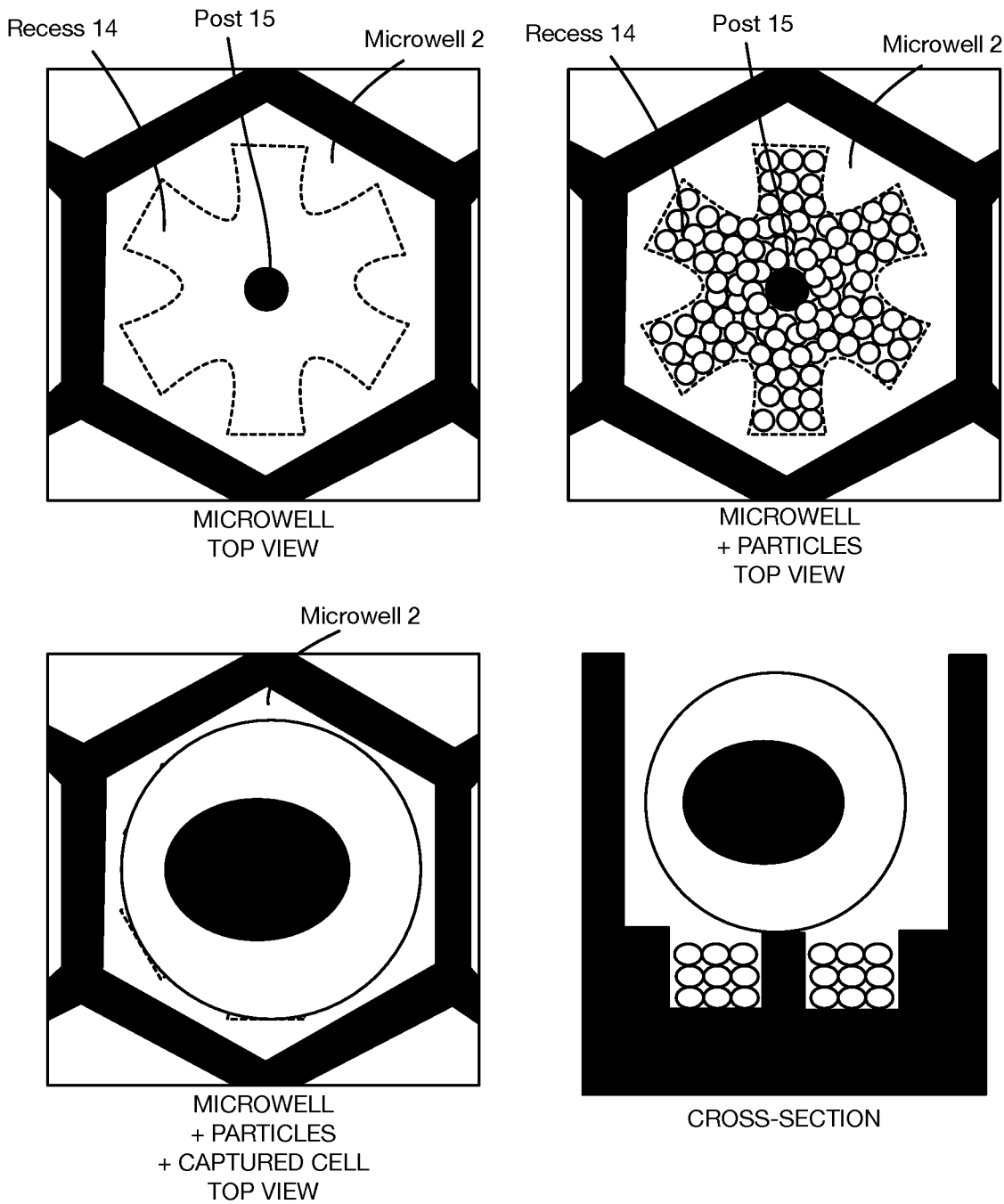
FIG. 14 depicts a fourth extension of a portion of a system and/or method for automated single cell sample processing.

In another extension, the system(s) and/or method(s) can implement microwell designs, whereby the microwell includes a recess 14 (e.g., star-shaped recess, ellipsoidal recess, polygonal recess, etc.) at the base of the microwell 2, with a post 15 (e.g., centrally-located post or multiple posts), where the recess 14 is configured to hold functionalized particles (e.g., embodiments of composition 200 described above), and the post 15 is configured to position a captured cell relative to the functionalized particles, within the microwell 2. FIG. 14 depicts top views of an example of the microwell 2 with recess 14 (FIG. 14, top left), the microwell 2 with functionalized particles within the recess (FIG. 14, top right and bottom right), and the microwell 2 with a captured cell (FIG. 14, bottom left and bottom right).

Figure 15:
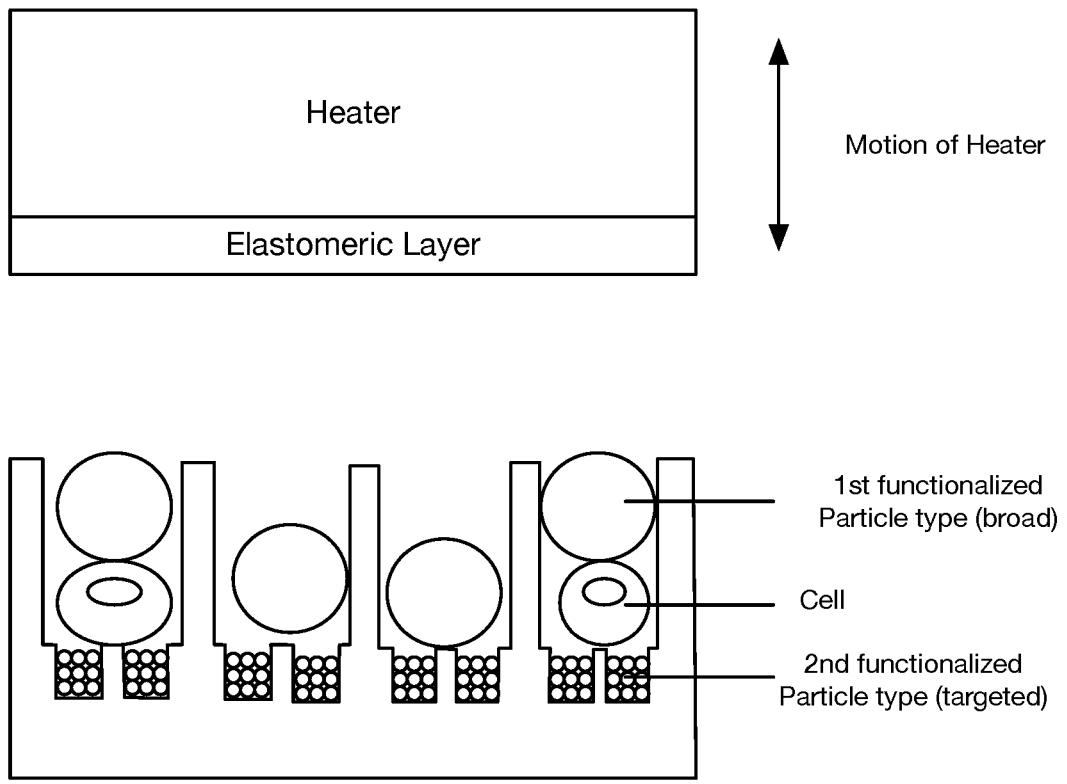
FIG. 15 depicts a fifth extension of a portion of a system and/or method for automated single cell sample processing.

Furthermore, extensions can be combined in any suitable manner. For instance, as shown in FIG. 15, an embodiment of the system show in FIG. 14 can be used for applications involving sequential processing of single cells to capture broad unspecific biomarkers at a first functionalized particle type, followed by targeted capture and detection at second particle type.

The method(s) described can, however, be extended to other applications of use.

4. Conclusion

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A method for detecting a set of targets comprising biomarkers of a sample, the method comprising:
    capturing a set of cells of the sample in proximity to a set of functionalized particles, in single cell format, at a first set of microwells of a sample processing substrate;
    performing lysis of the set of cells, at the sample processing substrate, thereby allowing binding of released biomarkers from the set of cells to the set of functionalized particles;
    performing a reverse transcription operation, at the first set of microwells of the sample processing substrate, with said biomarkers bound to the set of functionalized particles;
    with products of the reverse transcription operation, performing a second strand synthesis operation with the set of functionalized particles;
    with products of the second strand synthesis operation, performing an amplification operation at the set of functionalized particles;
    hybridizing each of a set of probes, corresponding to a set of fluorophores, to products of the amplification operation; and
    generating an image dataset of light emitted by the set of probes, thereby enabling detection of the set of targets of the sample.

2. The method of claim 1, wherein the set of targets comprises a panel of antibodies for assessment of immune responses from a subject, the panel of antibodies comprising one or more of: IgM antibodies, IgG antibodies, IgD antibodies, IgA antibodies, and IgE antibodies.

3. The method of claim 2, wherein the panel of antibodies comprises antibodies for severe acute respiratory syndrome coronavirus-2 (SARS-CoV-2).

4. The method of claim 1, wherein the set of targets comprises a panel of mRNA molecules.

5. The method of claim 4, further comprising performing a spatial transcriptomics analysis of the panel of mRNA molecules, with the sample distributed across the sample processing substrate.

6. The method of claim 1, wherein capturing the set of cells of the sample in proximity to the set of functionalized particles comprises delivering the set of cells to the first set of microwells of the sample processing substrate, and aligning the sample processing substrate with a second substrate comprising a second set of microwells having the set of functionalized particles retained within the second set of microwells, thereby exposing the set of cells to the set of functionalized particles at the second set of microwells.

7. The method of claim 6, further comprising compressing the second substrate, with the set of functionalized particles retained within the second set of microwells, against the first set of microwells, thereby partitioning individual wells of the sample processing substrate and allowing content derived from the set of cells to diffuse toward the set of functionalized particles at the second substrate.

8. The method of claim 7, wherein compressing the second substrate, with the second set of microwells, against the first set of microwells, comprises actuating a heating object against the second substrate, thereby providing compression and heating contents of at least one of the sample processing substrate and the second substrate.

9. The method of claim 1, wherein hybridizing each of the set of probes comprises hybridizing a first subset of the set of probes, corresponding to a first fluorophore, and performing a first detection operation; de-hybridizing and washing the first subset of probes; and hybridizing a second subset of the set of probes, corresponding to a second fluorophore, and performing a second detection operation.

10. The method of claim 1, wherein the set of probes (P) is configured for multiplexed detection of the set of targets, where the set of fluorophores (F) has a set of melting points (M), thereby enabling multiplexing of $M*F^P$ targets at the sample processing substrate.

11. The method of claim 1, further comprising performing an mRNA quantitation operation with estimation of initial concentrations of mRNAs captured at the set of functionalized particles, based upon a set of fluorescence values from the image data set and a number of amplification cycles performed.

12. A method for detecting a set of targets comprising biomarkers of a sample, the method comprising:
    capturing a tissue sample in proximity to a set of functionalized particles, in single array format, at a set of microwells of a sample processing substrate;
    performing lysis of the tissue sample, at the sample processing substrate, thereby allowing binding of released biomarkers from the tissue section to the set of functionalized particles;
    performing a reverse transcription operation, at the set of microwells of the sample processing substrate, with said biomarkers bound to the set of functionalized particles;
    with products of the reverse transcription operation, performing a second strand synthesis operation with the set of functionalized particles;
    with products of the second strand synthesis operation, performing an amplification operation at the set of functionalized particles;
    hybridizing each of a set of probes, corresponding to a set of fluorophores, to products of the amplification operation; and
    generating an image dataset of light emitted by the set of probes, thereby enabling detection of the set of targets of the sample.

13. The method of claim 12, wherein the set of targets comprises a panel of antibodies for assessment of immune responses from a subject, the panel of antibodies comprising one or more of: IgM antibodies, IgG antibodies, IgD antibodies, IgA antibodies, and IgE antibodies.

14. The method of claim 13, wherein the panel of antibodies comprises antibodies for severe acute respiratory syndrome coronavirus-2 (SARS-CoV-2).

15. The method of claim 12, wherein the set of targets comprises a panel of mRNA molecules.

16. The method of claim 15, further comprising performing a spatial transcriptomics analysis of the panel of mRNA molecules, with the sample distributed across the sample processing substrate.

* * * * *

UNITED STATES PATENT AND TRADEMARK OFFICE
CERTIFICATE OF CORRECTION

| | |
|---|---|
| PATENT NO. | : 11,724,256 B2 |
| APPLICATION NO. | : 16/890417 |
| DATED | : August 15, 2023 |
| INVENTOR(S) | : Kalyan Handique |

It is certified that error appears in the above-identified patent and that said Letters Patent is hereby corrected as shown below:

On the Title Page

Item (71) Applicant, Line 1, Delete "Inc," and insert --Inc.,-- therefor

Signed and Sealed this
Third Day of October, 2023

*Katherine Kelly Vidal*

Katherine Kelly Vidal
*Director of the United States Patent and Trademark Office*